US009409955B2

(12) United States Patent
Reguera et al.

(10) Patent No.: US 9,409,955 B2
(45) Date of Patent: *Aug. 9, 2016

(54) MICROBIAL NANOWIRES

(71) Applicant: BOARD OF TRUSTEES OF MICHIGAN STATE UNIVERSITY, East Lansing, MI (US)

(72) Inventors: Gemma Reguera, Lansing, MI (US); Rebecca Steidl, Williamson, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/448,843

(22) Filed: Jul. 31, 2014

(65) Prior Publication Data

US 2014/0336357 A1 Nov. 13, 2014

Related U.S. Application Data

(62) Division of application No. 13/221,495, filed on Aug. 30, 2011, now Pat. No. 8,846,890.

(60) Provisional application No. 61/378,240, filed on Aug. 30, 2010, provisional application No. 61/378,188, filed on Aug. 30, 2010.

(51) Int. Cl.
C07K 1/00 (2006.01)
C07K 14/195 (2006.01)
B82Y 5/00 (2011.01)

(52) U.S. Cl.
CPC ....... *C07K 14/195* (2013.01); *B82Y 5/00* (2013.01)

(58) Field of Classification Search
None
See application file for complete search history.

(56) References Cited

U.S. PATENT DOCUMENTS

| | | | |
|---|---|---|---|
| 5,418,140 A | 5/1995 | Chang et al. |
| 5,834,247 A | 11/1998 | Comb et al. |
| 5,968,769 A | 10/1999 | Green et al. |
| 6,897,285 B2 | 5/2005 | Xu et al. |
| 6,984,505 B2 | 1/2006 | Xu et al. |
| 6,987,007 B2 | 1/2006 | Xu et al. |
| 7,001,745 B1 | 2/2006 | Xu et al. |
| 7,060,465 B2 | 6/2006 | Xu et al. |
| 7,271,256 B2 | 9/2007 | Evans et al. |
| 7,498,155 B2 | 3/2009 | Lovley et al. |
| 7,517,671 B2 | 4/2009 | Taron et al. |
| 7,732,565 B2 | 6/2010 | Taron et al. |
| 8,729,233 B2 | 5/2014 | Reguera et al. |
| 8,846,890 B2 | 9/2014 | Reguera et al. |
| 2003/0216550 A1 | 11/2003 | Xu et al. |
| 2005/0196804 A1 | 9/2005 | Xu et al. |
| 2005/0196841 A1 | 9/2005 | Xu et al. |
| 2006/0030008 A1 | 2/2006 | Xu et al. |
| 2006/0035333 A1 | 2/2006 | Taron et al. |
| 2006/0199225 A1 | 9/2006 | Colussi et al. |
| 2007/0065880 A1 | 3/2007 | Taron et al. |
| 2007/0099234 A1 | 5/2007 | Zhang et al. |
| 2010/0167942 A1 | 7/2010 | Zheng et al. |
| 2011/0071280 A1 | 3/2011 | Taron et al. |
| 2011/0097737 A1 | 4/2011 | Samuelson et al. |
| 2012/0053319 A1 | 3/2012 | Reguera et al. |
| 2012/0053320 A1 | 3/2012 | Reguera et al. |
| 2014/0239237 A1 | 8/2014 | Reguera et al. |

FOREIGN PATENT DOCUMENTS

| | | |
|---|---|---|
| EP | 0036776 A2 | 9/1981 |
| JP | 2010-33344 A | 2/2010 |
| WO | 01/57183 A2 | 8/2001 |
| WO | 03/074660 A2 | 9/2003 |
| WO | 2006/041849 A2 | 4/2006 |
| WO | 2006/096821 A1 | 9/2006 |
| WO | 2009/026089 A1 | 2/2009 |
| WO | 2013/033456 A2 | 3/2013 |
| WO | 2013/033456 A3 | 4/2013 |

OTHER PUBLICATIONS

Non Final Office Action received for U.S. Appl. No. 13/221,459, mailed on Jan. 8, 2013, 11 pages.
Final Office Action received for U.S. Appl. No. 13/221,459, mailed on Jun. 26, 2013, 14 pages.
Notice of Allowance received for U.S. Appl. No. 13/221,459, mailed on Jan. 2, 2014, 8 pages.
Non Final Office Action received for U.S. Appl. No. 13/221,495, mailed on Jul. 12, 2013, 19 pages.
Final Office Action received for U.S. Appl. No. 13/221,495, mailed on Nov. 7, 2013, 22 pages.
Advisory Action received for U.S. Appl. No. 13/221,495, mailed on Jan. 27, 2014, 2 pages.
International Search Report and Written Opinion received for PCT Patent Application No. PCT/US2012/053221, mailed on Mar. 8, 2013, 15 pages.
Aklujkar et al., "Geopilin [*Geobacter bemidjiensis Bern*]", Accession No, YP_002139394.1, 2010, 1 page.
Aklujkar et al "Then Genome Sequenc of *Geobacter metallireducens*: Features of Metabolism, Physiology and Regulation Common and Dissmilar to *Geobacter sulfurreducens*" BMC Microbiology, vol. 9, May 27, 2009, 22 pages.
Altschul et al., "Gapped BLAST and PSI-BLAST: A New Generation of Protein Database Search Programs", Nucleic Acids Research, vol. 25, No. 17, Sep. 1997, pp. 3389-3402.
Ausubel et al., "Current Protocols in Molecular Biolocy", John Wiley and Sons, Inc., © 2003, Section II, Supplement 41 and Section III and Supplement 44, 1998, 517 pages.
Ausubel et al., "Current Protocols in Molecular Biology—Informatics for Molecular Biologists", John Wiley and Sons, Inc., © 2003, Chapter 19, Supplement 70, 2005, 137 pages.
Ausubel et al., "Current Protocols in Molecular Biology—Preparation and Analysis of DNA", John Wiley and Sons, Inc., © 2003, Chapter 2, Supplement 58, 2002, 161 pages.

(Continued)

*Primary Examiner* — Jennifer Graser

(57) ABSTRACT

The application describes electrically conductive nanowires, as well as genetically and/or chemically modified nanowires with modified conductive, adhesive and/or coupling properties.

23 Claims, 20 Drawing Sheets
(8 of 20 Drawing Sheet(s) Filed in Color)

(56) References Cited

OTHER PUBLICATIONS

Balch et al., "Methanogens: Reevaluation of a Unique Biological Group", Microbiological Reviews, vol. 43, No. 2, Jun. 1979, pp. 260-296.
Bernard et al., "Tight Attachment of Chitin-Binding-Domain-Tagged Proteins to Surfaces Coated with Acetylated Chitosan", Analytical Biochemistry, vol. 327, No. 2, Apr. 2004, pp. 278-283.
Bolivar et al., "Construction and Characterization of New Cloning Vehicles—II. A Multipurpose Cloning System", Gene, vol. 2, No. 2, Nov. 1977, pp. 95-113.
Chang et al., "Phenotypic Expression in E. coil of a DNA Sequence Coding for Mouse Dihydrofolate Reductase", Nature, vol. 275, Oct. 1978, pp. 617-624.
Chothia et al., "The Relation between the Divergence of Sequence and Structure in Proteins", The EMBO Journal, vol. 5, No. 4, Apr. 1986, pp. 823-826.
Claverie et al., "Information Enhancement Methods for Large Scale Sequence Analysis", Computers Chemistry, vol. 17, No. 2, Jun. 1993, pp. 191-201.
Collinson et al., "Purification and Characterization of Thin, Aggregative Fimbriae from *Salmonella enteritidis*", Journal of Bacteriology, vol. 173, No. 15, Aug. 1991, pp. 4773-4781.
Cologgi et al., "Extracellular Reduction of Uranium via *Geobacter* Conductve Pili as a Protecive Cellular Mechanism", PNAS, vol. 108, No. 37, 2011, pp. 15248-15252.
Copeland et al., "N-terminal Methylation [*Geobacter metallireducens GS-15*]", Accession No. YP_384358.1, 2005, 1 page.
Copeland et al., "Pilin Domain-Containing Protein [*Pelobacter propionicus DSM 2379*]", Accession No. YP_901328.1, 2006, 1 page.
Coppi et al., "Development of a Genetic System for *Geobacter sultioreducens*", Applied and Environmental Microbiology, vol. 67, No. 7, Jul. 2001, pp. 3180-3187.
Corpet, Florence, "Multiple Sequence Alignment with Hierarchical Clustering", Nucleic Acids Research, vol. 16, No. 22, Nov. 1988, pp. 10881-10890.
Cory et al., "Fluorescence Spectroscopy Reveals Ubiquitous Presence of Oxidized and Reduced Quinones in Dissolved Organic Matter", Environmental Science and Technology, vol. 39, No. 21, Nov. 2005, pp. 8142-8149.
Craig et al., "Type IV Pilus Structure by Cryo-Electron Microscopy and Crystallography: Implications for Pilus Assembly and Functions", Molecular Cell, vol. 23, No. 5, Sep. 2006, pp. 651-662.
De Boer et al., "The *tac* Promoter: A Functional Hybrid Derived from the *trp* and *iac* Promoters", PNAS, vol. 80, No. 1, Jan. 1983, pp. 21-25.
Fasman, Gerald D., "Practical Handbook of Biochemistry and Molecular Biology", CRC Press, © 1989, 7 pages.
Feliciano et al., "Molecular and Electronic Structure of the Peptide Subunit of *Geobacter sulfurroducens* Conductive Pili from First Principles", The Journal of Physical Chemistry A, vol. 116, No. 30, Jul. 2012, pp. 8023-8030.
Feng et al., "Progressive Sequence Alignment as a Prerequisite to Correct Phylogenetic Trees", Journal of Molecular Evolution, vol. 25, No. 4, Aug. 1987, pp. 351-360.
Ferrandon et al., "A Single Surface Ttryptophan in the Chitin-Binding Domain From *Bacillus circulans* Chitinase A1 Plays a Pivotal Role in Binding Chitin and can be Modified to Create an Elutable Affinity Tag", Biochimica et Biophysica Acta, vol. 1621, Apr. 2003, pp. 31-40.
Fong et al., "The Potential Role of Self-Cleaving Purification Tags in Commercial-Scale Processes", Trends in Biotechnology, vol. 28, No. 5, 2010, pp. 272-279.
Forero, Angelines A. Castro, "Properties and Applications of Self-Assembled Biomolecules in Nanostructured Biomimetic Interfaces", A Dissertation Submitted to Michigan State University, 2011, 54 pages.
Genbank Accession No. ZP05310612.1, "Pilin Domain-containing Protein [*Geobacter* sp. *M18*]", available online at <http://www.ncbi.nlm.nih.gov/protein/ZP_05310612.1?report=genpept>, Nov. 9, 2010, 1 page.

Goeddel e al "Direct Expression in *Escherichia coli* of a DNA Sequence Coding for Human Growth Hormone", Nature, vol. 281, Oct. 1979, pp. 544-548.
Goeddel et al., "Synthesis of Human Fibroblast Interferon by *E. coil*", Nucleic Acids Research, vol. 8, No. 18, Sep. 1980, pp. 4057-4074.
Greenfield, Norma J. "Using Circular Dichroism Spectra to Estimate Protein Secondary Structure", Nature Protocols, vol. 1, No. 6, 2006, pp. 2876-2890.
Guzman et al., "FTSL, An Essential Cytoplasmic Membrane Protein Involved in Cell Division in *Escherichia coli*", Journal of Bacteriology, vol. 174, No. 23, Dec. 1992, pp. 7716-7728.
Guzman et al., "Tight Regulation, Moduiation, and High-Level Expression by Vectors Containinc the Arabinose Pbad Promoter", Journal of Bacteriology, vol. 177, No. 14, Jul. 1995, pp. 4121-4130.
Haldimann et al., "Use of Now Methods for Construction of Tightly Regulated Arabinose and Rhamnose Promoter Fusions in Studies of the *Escherichia coil* Phosphate Regulon", Journal of Bacteriology, vol. 180, No. 5, Mar. 1998, pp. 1277-1286.
Hay et al., "Protein Engineering of Cytochrome b562 for Quinone Binding and Light-Induced Electron Transfer", PNAS, vol. 101, No. 51, Dec. 2004, pp. 17675-17680.
Henikoff et 81., "Amino Acid Substitution Matrices from Protein Blocks", PNAS, vol. 89, No. 22, Nov. 1992, pp. 10915-10919.
Higgins et al., "CLUSTAL: A Package for Performing Multiple Sequence Alignment on a Microcomputer", Gene, vol. 73, No. 1, Dec. 1988, pp. 237-244.
Higgins et al., "Fast and Sensitive Multiple Sequence Alignments on a Microcomputer", Computer Applications in the Biosciences, vol. 5, No. 1, Feb. 1989, pp. 151-153.
Huang et al., "Parallelization of a Local Similarity Agorithm", Computer Applications in the Biosciences, vol. 8, No. 1, Feb. 1992, pp. 155-165.
Kyte et al., "A Simple Method for Displaying the Hydropathic Character of a Protein", Journal of Molecular Biology, vol. 157, No. 1, May 1982, pp. 105-132.
Leang et al., "Alignment of the c-Type Cytochrome OmcS Along Pili of *Geobacter sulferreducens*", Applied and Environmental Microbiology, vol. 76, No. 12, Jun. 2010, pp. 4080-4084.
Leang et al., "Genome-Wide Analysis of the RpoN Regulon in *Geobacter sulfurreducens*", BMG Genomics, vol. 10, Jul. 2009, pp. 1-19.
Li et al., "Fed-Batch Fermentor Synthesis of 3-Dehydroshikimic Acid using Recombinant *Escherichia coil*", Biotechnology and Bioengineering, vol. 64, No. 1, Jul. 1999, pp. 61-73.
Lovley et al., "Novel Mode of Microbial Energy Metabolism: Organic Carbon Oxidation Coupled to Dissimilatory Reduction of Iron or Manganese", Applied and Environmental Microbiology, vol. 54, No. 6, Jun. 1988, pp. 1472-1480.
Lovley et al., "Rapidly Growing Rumen Methangenic Organism that Synthesizes Coenzyme M and has a High Affinity for Formate", Applied and Environmental Microbiology, vol. 48, No. 1, Jul. 1984, pp. 81-87.
Lucas et al., "Pilin [*Geobacter* sp. *M21*]", Accession No. YP_003021449.1, 2009, 1 page.
Lucas et al., "Pilin Domain-Containing Protein [*Geobacter lovleyi SZ*]", Accession No. YP_001952332.1, 2008, 1 page.
Lutz et al., "Independent and Tight Regulation of Transcriptional Units in *Escherichia Coli* via the LacR/O, the TetR/O and AraC/I1-I2 Regulatory Elements", Nucleic Acids Research, vol. 25, No. 6, Mar. 1997, pp. 1203-1210.
Malhotra, Arun, "Tagging for Protein Expression", Chapter 16, Methods in Enzymology, vol. 463, © 2009, pp. 239-258.
Means et al., "Chemical Modifications of Proteins", Holden-Day Inc., San Francisco, © 1971, 7 pages.
Meinkoth et al., "Hybridization of Nucleic Acids immoblized on Solid Supports", Anaytical Biochemistry, vol. 138, No. 2, May 1984, pp. 267-284.
Menzella et al., "Novel *Escherichia coli* Strain Aliows Efficient Recombinant Protein Production using Lactose as Inducer", Biotechnoiogy and Bioengineering, vol. 82, No. 7, Jun. 2003, pp. 809-817.

(56) References Cited

OTHER PUBLICATIONS

Methe et al., "Genome of *Geobacter sulfurreducens*: Metal Reduction in Subsurface Environments", Science, vol. 302, Dec. 12, 2003, pp. 1967-1969.
Methe et al., "Hypothetical Protein GSU1496 [*Geobacter sulfurreducens PCA*]", Accession No. NP_952547.1, 2003, 1 page.
Mihalyi, Elemer "Numerical Values of the Absorbances of the Aromatic Amino Acids in Acid, Neutral, and Alkaline Solutions", Journal of Chemical and Engineering Data, vol. 13, No. 2, Apr. 1968, pp. 179-182.
Mikayama et al., "Molecular Cloning and Functional Expression of a cDNA Encoding Glycosylation-Inhibiting Factor", PNAS, vol. 90, No. 21, Immunology, Nov. 1993, pp. 10056-10060.
Nagarajan et al., "De Novo Assembly of the Complete Genome of an Enhanced Electricity-Producing Variant of *Geobacter sulfurreducens*, Using Only Short Reads", PLoS ONE, vol. 5, No. 6, Jun. 2010, 9 pages.
Nagarajan et al., "Type IV Pilin PilA [*Geobacter sulfurreducens KN400*]", Accession No. ADI84335, 2010, 1 page.
Needleman et al., "A General Method Applicable to the Search for Similarities in the Amino Acid Sequence of Two Proteins", Journal of Molecular Biology, vol. 48, No. 3, Mar. 1970, pp. 443-453.
Pearson et al., "Improved Tools for Biological Sequence Comparison", PNAS, vol. 85, No. 8, Biochemistry, 1988, pp. 2444-2448.
Provencher et al., "Estimation of Globular Protein Secondary Structure from Circular Dichroism", Biochemistry, vol. 20, No. 1, Jan. 1981, pp. 33-37.
Reguera et al., "Extracellular Electron Transfer via Microbial Nanowires", Letters, Nature, vol. 435, Jun. 2005, pp. 1098-1101.
Reguera et al., "Possible Nonconductive Role of *Geobacter sulfurreducens* Pilus Nanowires in Biofilm Formation", Journal of Bacteriology, vol. 189, No. 5, Mar. 2007, pp. 2125-2127.
Rudinger, J., "Characteristics of the Amino Acids as Components of a Peptide Hormone Sequence", National Institute for Medical Research, Jun. 1976, 8 pages.
Sambrook et al., "Molecular Cloning—A Laboratory Manual", 3rd Edition, Chapter 2, Cold Spring Harbor Laboratory Press, © 2001, 138 pages.
Siegele et al., "Gene Expression from Plasmids Containing the *araBAD*Promoter at Subsaturating Inducer Concentrations Represents Mixed Populations", PNAS, vol. 94, No. 15, Jul. 1997, pp. 8168-8172.
Smith et al., "Comparison of Biosequences", Advances in Applied Mathematics, vol. 2, No. 4, 1981, pp. 482-489.
Sreerama et al., "Estimation of Protein Secondary Structure from Circular Dichroism Spectra: Comparison of CONTIN, SELCON, and CDSSTR Methods with an Expanded Reference Set", Analytical Biochemistry, vol. 287, No. 2, Dec. 2000, pp. 252-260.
Tijssen, P., "Overview of Principles of Hybridization and the Strategy of Nucleic Acid Probe Assays", Chapter 2, Laboratory Techniques in Biochemistry and Molecular Biology—Hybridization with Nucleic Acid Probes, Part 1, © 1993, 11 pages.
Van Stokkum et al., "Estimation of Protein Secondary Structure and Error Analysis from Circular Dichroism Spectra", Analytical Biochemistry, vol. 191, No. 1, Nov. 1990, pp. 110-118.
Veazey et al., "Electronic Properties of Conductve Pili of the Metal-Reducing Bacterium *Geobacter sulfureducens*Probed by Scanning Tunneling Microscopy", Physical Review E, vol. 84, Dec. 2011, pp. 060901-1-060901-4.
Veazey et al., "Microbial Nanowire Electronic Structure Probed by Scanning Tunneling Microscopy", Biophysical Journal, vol. 98, No. 3, 2010, 1 page.
Walker, John M., "The Protein Protocols Handbook", Parts II and III, Second Edition, Humana Press Inc., 2002, 400 pages.
Wallace et al., "Modern Techniques for Circular Dichroism and Synchrotron Radiation Circular Dichroism Spectroscopy", Advances in Biomedical Spectroscopy, vol. 1, 2009, 245 pages.
Whitmore et al., "DICHROWEB, An Online Server for Protein Secondary Structure Analyses from Circular Dichroism Spectroscopic Data", Nucleic Acids Research, vol. 32, Suppl. 2, Jul. 2004, pp. W668-W673.
Whitmore et al., "Protein Secondary Structure Analyses from Circular Dichroism Spectroscopy: Methods and Reference Databases", Biopolymers, vol. 89, No. 5, May 2008, pp. 392-400.
Wootton et al., "Statistics of Local Complexity in Amino Acid Sequences and Sequence Databases", Computers and Chemistry, vol. 17, No. 2, Jun. 1993, pp. 149-163.
Yang et al., "Metabolic Response of *Geobacier sulfurreducens* towards Electron Donor/Acceptor Variation", Microbial Cell Factories 2010, vol. 9, No. 90, Nov. 2010, 15 pages.

Fig. 1

1........10........20........30........40........50........60
FTLIELLIVVAIIGILAAIAIPQFSAV V AVNSAASSDL NL TALESAFADDQTVPPES

Fig. 2A

MICROBIAL NANOWIRES

This application is a divisional of U.S. patent application Ser. No. 13/221,945, filed on, Aug. 30, 2011, which application claims benefit under 35 U.S.C. 119 (e) of U.S. Patent Application Ser. No. 61/378,240, filed Aug. 30, 2010, and U.S. Patent Application Ser. No. 61/378,188, filed Aug. 30, 2010, which applications are each hereby incorporated by reference herein in its entirety.

This application is related to U.S. application Ser. No. 13/221,459, filed on Aug. 30, 2011, which application issued as U.S. Pat. No. 8,729,233 on May 20, 2014, which application and patent are each incorporated by reference herein in its entirety.

STATEMENT OF GOVERNMENT RIGHTS

This invention was made with support under MCB1021948 awarded by the National Science Foundation and under ES017052 awarded by the National Institutes of Health. The government has certain rights in this invention.

BACKGROUND OF THE INVENTION

Semiconductor electronics have exhibited a sustained exponential decrease in size and cost with a similar increase in performance over the last thirty years. While such progress is expected to continue for several years, the economics and/or physical barriers of continued use of silicon for increasingly small and more powerful devices will ultimately pose a challenge. For example, if only currently available technologies are employed, the costs of building the necessary manufacturing facilities will likely become prohibitive due to the shrinking size of devices, heat dissipation problems due to closely packed structures, non-uniformity in dopant and conductive materials, and high electric fields that may lead to a cascade of breakdown events within closely packed components.

Moreover, increases in pollution have been tied with increased energy consumption for at least the last several hundred years. Accelerated global warming and environmental degradation make the development of alternative energy sources an urgent priority.

The world therefore needs new sources of energy and new materials for use in fuel cells and nanoelectronic devices.

SUMMARY OF THE INVENTION

Microbes have the potential to address the problems of pollution, the need for clean affordable energy and the need for new nanoelectronic materials. The invention described herein relates to microbial nanowires that conduct electricity. Such nanowires are made from microbial pilins (or pili). The invention also relates to expression cassettes, expression vectors and host cells (e.g., bacteria) that produce such pilins and nanowires. In some embodiments, the nucleic acids encoding the nanowire polypeptides are recombinantly modified so that nanowire polypeptides with modified conductive properties can be produced.

Thus, one aspect of the invention is a nanowire polypeptide comprising an amino acid sequence selected from the group consisting of SEQ ID NO:1-10. In some embodiments the amino acid sequence of the nanowire polypeptide is genetically or chemically modified so that the nanowire polypeptide has electrical conductivity activity that is different from the wild type nanowire polypeptide having any of SEQ ID NO: 1-10. For example, the electrical conductivity activity of the modified nanowire polypeptide can be less than 90% or greater than 120% of the electrical conductivity activity of a wild type nanowire polypeptide comprising SEQ ID NO:1-10. In other embodiments, the modified nanowire polypeptides have modified adhesive or coupling properties relative to wild-type nanowire polypeptides. In some embodiments, the nanowire polypeptide is an isolated polypeptide, meaning that it has been separated from its natural environment.

Another aspect of the invention is a pilus that includes such a modified nanowire polypeptide. Further aspects of the invention include nucleic acids encoding such a genetically modified nanowire polypeptide, expression cassettes, expression vectors and host cells for expressing the modified nanowire polypeptides.

DESCRIPTION OF THE FIGURES

The patent or application file contains at least one drawing executed in color. Copies of this patent or patent application publication with color drawing(s) will be provided by the Office upon request and payment of the necessary fee.

FIG. 1 shows an alignment of the pilin nanowire sequences (SEQ ID NO:1-8) from the genomes of different Geobacteraceae species (top) and a profile reflecting the residue conservation (bottom). Amino acids conserved in all the sequences are marked with a star on top, those sharing similar physicochemical characteristics are marked with a colon (':'), while those with somewhat different chemical or physical characteristics are identified with a period or dot ('.').

FIG. 2A-C illustrates the primary and secondary structures of pili from *Geobacter sulfurreducens*. FIG. 2A shows the SEQ ID NO:9 amino acid sequence of a nanowires pilin from *Geobacter sulfurreducens*. The locations of the conserved tyrosine residues (Y) are identified with black shading while the negatively charged amino acids aspartic acid and glutamic acid (D and E, respectively) are identified with underlining and the positively charged amino acids lysine, arginine and histidine (K, R, and H, respectively) are identified with grey shading. FIG. 2B shows the predominantly helical secondary structure of the *Geobacter* pilin nanowire (GEO) compared to that of the pilin of *P. aeruginosa* strain K (PAK), which serves as a structural model for other bacterial pili. FIG. 2C shows the location of certain amino acids and their side chains within the structure of the *Geobacter* pilin nanowires.

As shown in FIG. 3A, the coulombic efficiencies, which depend on the cell's ability to metabolize the electron donor and convert it into electricity, were undisturbed. However, FIG. 3B shows that the amino acid replacements resulted in nanowires with reduced conductivity, as indicated by the observed defects in the electron transfer rates to electrodes in microbial fuel cells.

FIGS. 6A and 6B show distal conductivity measurements of purified pili by scanning tunnel microscopy (STM). FIG. 6C shows axial conductivity along the purified pili of nanowires by Conductive Probe-Atomic Force Microscopy (CP-AFM) according to an embodiment.

FIG. 7A is a STM topographical image of *G. sulfurreducens* pilus acquired using 0.5 V and 100 pA, while FIG. 7B is a STM topographical image of PAK pili acquired at 3.0 V and 45 pA. FIG. 7C shows STM I-V curves acquired at pili locations indicated by dots in FIG. 7A (black "A") and FIG. 7B (gray "B").

FIG. 8A shows a TEM micrograph of negatively stained *G. sulfurreducens* pili purified as thick bundles at pH 7 according to methods described in the Examples. FIG. 8B shows a TEM micrograph of negatively stained *G. sulfurreducens* pili deaggregated into individual pilus filaments at pH 9.5. FIG. 8C shows a silver-stained gel (left panel) after SDS-PAGE of octyl-glucoside-depolymerized *G. sulfurreducens* pili, illustrating the 6.5 kDa PilA protein band. The right panel of FIG. 8C illustrates the binding of anti-PilA polyclonal antibodies with the *G. sulfurreducens* pili peptide.

FIG. 11A shows an absorption spectrum of purified *G. sulfurreducens* pili and, in the inset, the spectrum is shown in comparison to a standard. FIG. 11B shows a fluorescence spectrum of purified *G. sulfurreducens* pili, and in the inset, the fluorescent spectra of L-tyrosine (solid line) and menaquinone (dashed line). Note that tyrosines yield two fluorescence peaks corresponding to the tyrosine (Tyr) and tyrosinate (Tyr•) forms. FIG. 11C shows a fluorescence spectrum of a riboflavin standard solution in isopropanol.

FIG. 12A is an AFM image of pili deposited onto a 25-nm thick gold electrode nanofabricated onto an insulating $SiO_2$ surface according to an embodiment. FIG. 12B is a schematic of a two-point transport measurement between the gold electrode and a CP-AFM tip through a pilus filament according to an embodiment. FIG. 12C show I-V (current-voltage) curves obtained with CP-AFM according to various embodiments.

DETAILED DESCRIPTION OF THE INVENTION

Figure 2B:
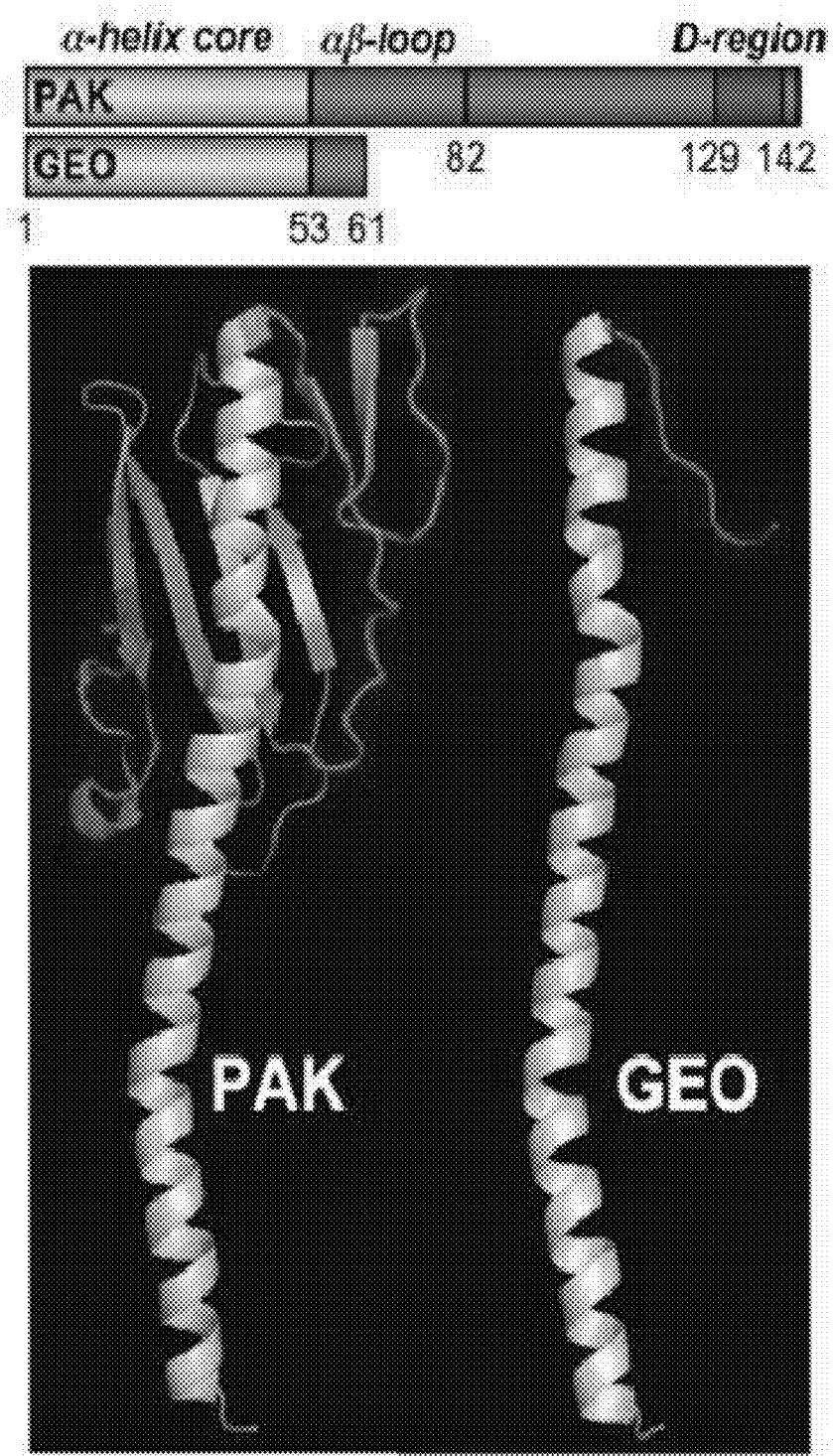

The invention described herein relates to microbial nanowires with sequences modified to modulate their conductive, adhesive, coupling and/or other properties. Such nanowires are useful for development of nanoelectronic devices and microbial fuel cells.

Microbial Nanowires

Geobacteraceae bacteria naturally produce protein filaments known as pili that are electrically conductive. For this reason, they are generally referred to as microbial or pilus nanowires. The pilus nanowires are protein filaments assembled on the cell envelope through the polymerization via hydrophobic interactions of a single peptide subunit, the pilin or PilA. The purified pili are electrically conductive. As the pili protrude outside the cell, other proteins, such as metalloproteins known as c-cytochromes, can bind the pili and may contribute to their conductivity and adhesive properties. However, biochemical analyses of the purified pilin subunits have demonstrated that they were not directly associated with metals or metalloenzymes even when they assemble into nanowires. Furthermore, they lack any biological redox cofactors such as flavins and quinones. Thus, the conductivity of the pilin subunits is intrinsic to the nanowire protein filament and is not due to any redox-active component that may associate with the nanowire polypeptide, such as metals, ions, contaminants, metalloenzymes, flavins or quinones.

The peptide subunit (or pilin) in the electrically conductive pili is encoded by the pilA gene of Geobacteraceae bacteria. The product of the pilA gene generates a peptide or PilA or pilin that polymerizes via hydrophobic interactions to form the pilus. The Geobacteraceae pilus nanowire electrically connects the cell with electron acceptors in its environment. This electronic connection enables the cell to gain energy through the transfer of metabolically-generated electrons across electron transport proteins, such as c-cytochromes and other metalloproteins of the cell envelope, and through the pilus. The pilus serves as the main electrical connection between the cell and extracellular acceptors such as Fe(III) oxides. *Geobacter sulfurreducens* is naturally found in underground sediment where anaerobic conditions may require that an electron acceptor other than oxygen be employed and where minerals or other electron acceptors are commonly available. Thus, although *Geobacter sulfurreducens* can utilize oxygen as an electron acceptor, these bacteria can also transfer electrons from their pili to extracellular electron acceptors such as Fe(III) oxides, resulting in insoluble Fe(III) in the environment to be reduced to soluble Fe(II).

The pilus nanowires are dynamic filaments that protrude and retract by polymerizing and depolymerizing the pilin subunits at the cell envelope. Thus, several pilin peptides are assembled to make a pilus that can function as a nanowire. Extension and retraction events are powered, respectively, by the PilB (pilin polymerase) and PilT (pilin depolymerase) proteins, which belong to the secretion NTPase superfamily. The pilus nanowires are predominantly helical (FIG. 2) in structure. In particular, they are composed of an α-helical core spanning the hydrophobic N-terminus region that promotes pilin polymerization, and a short αβ-loop in the C-terminal region. Thus, they lack the long αβ-loop and extensive C-terminal globular head that other bacterial pili possess.

Pilin assembly occurs via hydrophobic interactions proceeding in a helical fashion that may help position electroactive amino acids by merging or bonding their atomic orbitals optimally so as to favor charge transport along and across the nanowire.

Examples of several amino acid sequences of nanowires pilins (or PilA subunits) from different Geobacteraceae are shown in FIG. 1 (i.e., SEQ ID NO: 1-9).

Amino acids 20-90 of the *Geobacter sulfurreducens* PCA nanowire PilA with sequence accession number NP_952547.1 (gi: 39996596) has the following sequence (SEQ ID NO:1).

```
  1   MIQKLRNRKG FTLIELLIVV AIIGILAAIA IPQFSAYRVK
 41   AYNSAASSDL RNLKTALESA FADDQTYPPE S
```

The Type IV pilin PilA from *Geobacter sulfurreducens* KN400 having sequence accession number AD184335.1 (gi: 298505612) has the following sequence (SEQ ID NO:2).

```
  1   MLQKLRNRKG FTLIELLIVV AIIGILAAIA IPQFSAYRVK
 41   AYNSAASSDL RNLKTALESA FADDQTYPPE S
```

The pilin domain-containing protein *Geobacter lovleyi* SZ having sequence accession number YP_001952332.1 (gi: 189425155) has the following sequence (SEQ ID NO:3).

```
  1   MLNKIRNRKG FTLIELLIVV AIIGILAAVA IPQFTTYRIK
 41   GYNSNATSDL RNLKTVLESV FADRQGYPGS
```

The pilin domain-containing protein of *Pelobacter propionicus* DSM 2379 having sequence accession number YP_901328.1 (gi: 118580078) has the following sequence (SEQ ID NO:4).

```
  1   MLNKLRNRKG FTLIELLIVV AIIGILAAIA IPQFSAYRAK
 41   AYNSAANSDL KNIKTGMEAF MADNQQYPGD VDYR
```

The domain from *Geobacter metallireducens* GS-15 having sequence homology to *Geobacter* pilins and having accession number YP_384358.1 (gi:78222611) has the following sequence (SEQ ID NO:5).

```
  1   MLQKLRNKKG FTLIELLIVV AIIGILAAIA IPQFAAYRQK
 41   AFNSAAESDL KNTKTNLESY YSEHQFYPN
```

The pilin from *Geobacter* sp. M21 having accession number YP_003021449.1 (gi:253700260) has the following sequence (SEQ ID NO:6).

```
  1   MLNKLRSNKG FTLIELLIVV AIIGILAAIA IPQFSAYRAK
 41   AYNAANSDL KNMKTGMEAY MADRQAYPAL LDQR
```

The pilin from *Geobacter bemidjiensis* Bem having accession number YP_002139394.1 (gi:197118967) has the following sequence (SEQ ID NO:7).

```
  1   MLNKLRSNKG FTLIELLIVV AIIGILAAIA IPQFSAYREK
 41   AYNAASNSDL KNFKTGLEAF NADFQTYPAA YVASTN
```

The pilin domain-containing protein from *Geobacter* sp. M18 having accession number ZP_05310612.1 (gi: 255058444) has the following sequence (SEQ ID NO:8).

```
  1   MLNKIRSNKG FTLIELLIVV AIIGILAAIA IPQFSAYRAK
 41   AYNAAANSDL KNIKTGMEAY MADRQAYPVS LDER
```

Figure 2C:
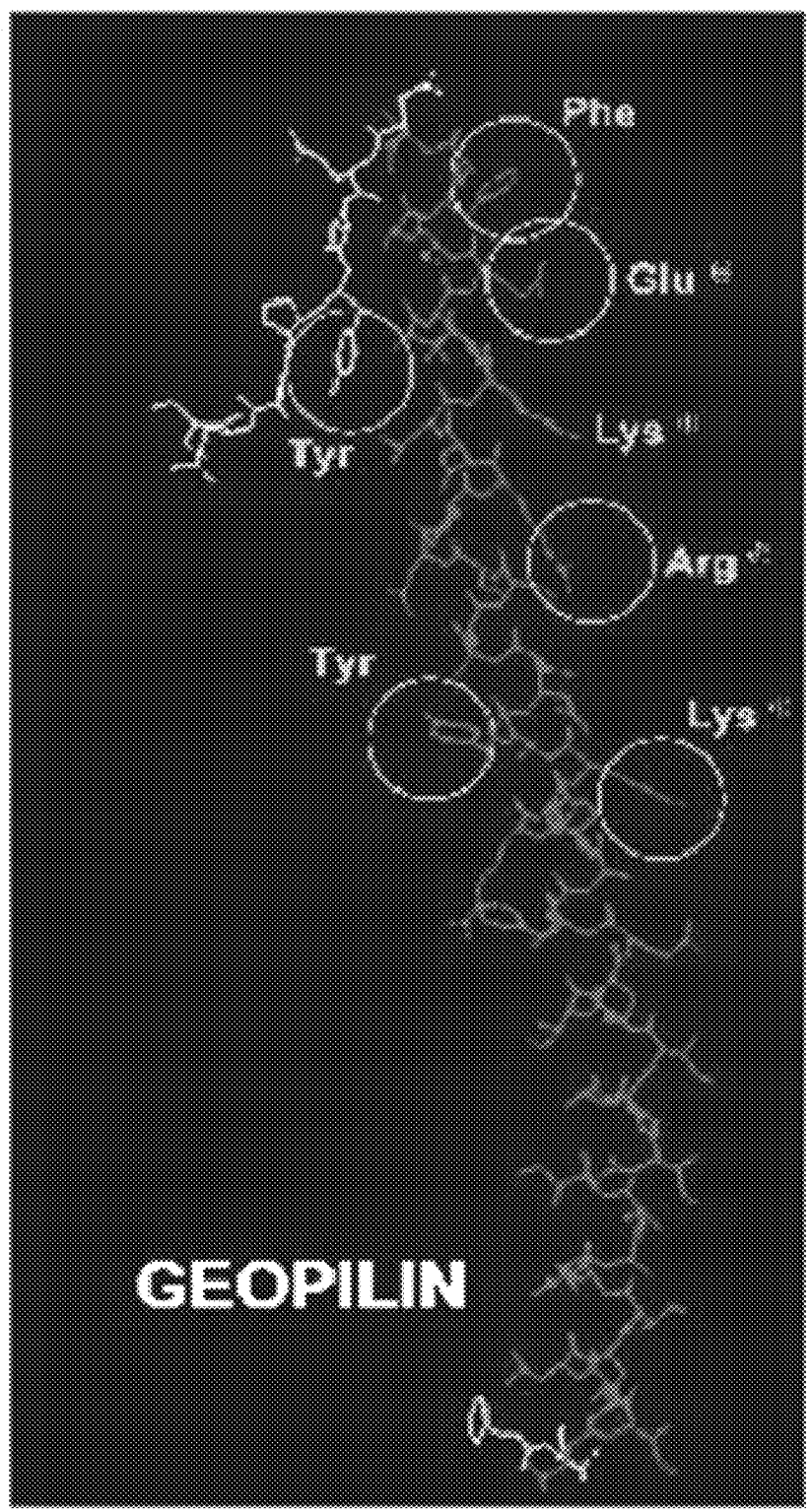

FIG. 2 shows the SEQ ID NO:9 amino acid sequence of the pilin nanowire subunit of *Geobacter sulfurreducens*. This SEQ ID NO:9 sequence is reproduced below.

```
  1   FTLIELLIVV AIIGILAAIA IPQFSAYRVK AYNSAASSDL
 41   RNLKTALESA FADDQTYPPE S
```

The amino acid sequence of the pilin PilA from *Geobacter sulfurreducens* is shown below as SEQ ID NO:10.

```
  1   MLQKLRNRKG FTLIELLIVV AIIGILAAIA IPQFSAYRVK
 41   AYNSAASSDL RNLKTALESA FADDQTYPPE S
```

The processing site for the SEQ ID NO: 10 signal peptide is between the glycine at position 10 and the phenylalanine at position 11. Removal of this signal peptide yields the SEQ ID NO:9 nanowire sequence shown in FIG. 2A. The N-terminal phenylalanine is also methylated during processing of the signal peptide (not shown in FIG. 2A).

The SEQ ID NO:9 and 10 nanowire polypeptides are encoded by the following pilA nucleic acid sequence (SEQ ID NO: 11).

```
  1   ATG CTT CAG AAA CTC AGA AAC AGG AAA GGT
 31   TTC ACC CTT ATC GAG CTG CTG ATC GTC GTT
 61   GCG ATC ATC GGT ATT CTC GCT GCA ATT GCG
 91   ATT CCG CAG TTC TCG GCG TAT CGT GTC AAG
121   GCG TAC AAC AGC GCG GCG TCA AGC GAC TTG
151   AGA AAC CTG AAG ACT GCT CTT GAG TCC GCA
181   TTT GCT GAT GAT CAA ACC TAT CCG CCC GAA
211   AGT TAA
```

According to the invention microbial pilin subunits can be genetically engineered for controlled and/or customized electronic, microbial fuel and other utilities. In one embodiment, the genetically engineered microbial nanowire polypeptide is a modified *Geobacter sulfurreducens* nanowires polypeptide. In other embodiments, the genetically engineered microbial nanowire polypeptide is a modification of any of the SEQ ID NO: 1-10 amino acid sequences. Such nanowire polypeptides can be modified using available recombinant technology procedures to generate mutant nanowire polypeptides with modified conductive, adhesive, coupling and/or other properties.

The nanowires can include one or more subunits with various molecular weights (MW). The subunits can have a variety of molecular weights ranging from, for example, at least about 3-kDa, or higher, or between about 3-kDa and about 25-kDa or between about 3-kDa and 20-kDa or between about 3-kDa and about 10-kDa or between about 4-kDa and about 9-kDa, or between about 5.5-kDa and about 7.5-kDa, including any range there between. In one embodiment, the subunit molecular weight is about 6.5-kDa or at least about 6.5-kDa. In one embodiment, nanowires formed by such subunits do not contain metals, ions, contaminants, metalloenzymes, flavins or quinones.

Thus, for example, any of the SEQ ID NO:1-10 amino acid sequences can be modified using available recombinant technology procedures to generate mutant nanowire polypeptides with modified conductive, adhesive, coupling and/or other properties.

As illustrated herein, the tyrosine and charged amino acids are largely responsible for the conductive function of the nanowires. In some embodiments, tryptophan may also contribute to the conductive function of the nanowires. Thus, to modulate the conductive function of the nanowires, their amino acid sequences can be modified to include a greater or lesser proportion of the tyrosine, tryptophan and/or charged amino acids.

Amino acid residues of the nanowires can be genetically encoded L-amino acids, naturally occurring non-genetically encoded L-amino acids, synthetic L-amino acids, D-enantiomers of any of the above and combinations of any of these amino acids. The amino acid notations used herein for the twenty genetically encoded L-amino acids and common non-encoded amino acids are conventional and are as shown in Table 1.

TABLE 1

| Amino Acid | One-Letter Symbol | Abbreviation |
|---|---|---|
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |
| β-Alanine | | bAla |
| 2,3-Diaminopropionic acid | | Dpr |
| α-Aminoisobutyric acid | | Aib |
| N-Methylglycine (sarcosine) | | MeGly |
| Ornithine | | Orn |
| Citrulline | | Cit |
| t-Butylalanine | | t-BuA |
| t-Butylglycine | | t-BuG |
| N-methylisoleucine | | MeIle |
| Phenylglycine | | Phg |
| Cyclohexylalanine | | Cha |
| Norleucine | | Nle |
| Naphthylalanine | | Nal |
| Pyridylalanine | | |
| 3-Benzothienyl alanine | | |
| 4-Chlorophenylalanine | | Phe(4-Cl) |
| 2-Fluorophenylalanine | | Phe(2-F) |
| 3-Fluorophenylalanine | | Phe(3-F) |

TABLE 1-continued

| Amino Acid | One-Letter Symbol | Abbreviation |
|---|---|---|
| 4-Fluorophenylalanine | | Phe(4-F) |
| Penicillamine | | Pen |
| 1,2,3,4-Tetrahydro-isoquinoline-3-carboxylic acid | | Tic |
| β-2-thienylalanine | | Thi |
| Methionine sulfoxide | | MSO |
| Homoarginine | | hArg |
| N-acetyl lysine | | AcLys |
| 2,4-Diamino butyric acid | | Dbu |
| P-Aminophenylalanine | | Phe(pNH$_2$) |
| N-methylvaline | | MeVal |
| Homocysteine | | hCys |
| Homoserine | | hSer |
| E-Amino hexanoic acid | | Aha |
| δ-Amino valeric acid | | Ava |
| 2,3-Diaminobutyric acid | | Dab |

Nanowire polypeptides that are encompassed within the scope of the invention include any of these amino acids and include mutant nanowire polypeptides having one or more of the amino acids within the SEQ ID NO: 1-10 sequences substituted with other, different amino acids.

While the substituted or replaced amino acid may have similar physical and chemical characteristics, it may also have different physical or chemical characteristics. For example, an amino acid from any of the SEQ ID NO:1-10 nanowire sequences that has no direct role in electrical conductivity may be replaced by an amino acid that has a direct role in electrically conducting electrons along the pilus nanowire (e.g., a tyrosine and/or a charged amino acid). Alternatively, an amino acid from any of the SEQ ID NO: 1-10 nanowire sequences that has a direct role in electrical conductivity may be replaced by an amino acid that has an indirect role in electrically conducting electrons along the pilus nanowires, or some other role such as adhesion, secondary or tertiary structure formation, and the like.

In general, amino acids can be placed into three main classes: hydrophilic amino acids, hydrophobic amino acids and cysteine-like amino acids, depending primarily on the characteristics of the amino acid side chain. These main classes may be further divided into subclasses. For example, some types of hydrophobic amino acids have aromatic side chains while other types of hydrophobic amino acids do not have aromatic side chains. Moreover, aromatic amino acids can have functional groups that provide a more hydrophilic character and that permit acceptance and transport of electrons (e.g., tyrosine). In general, the hydrophilic and/or aromatic amino acids have a more direct role in the electrical conductivity functions of the pilus nanowires.

Hydrophilic amino acids include amino acids having acidic, basic or uncharged polar side chains and hydrophobic amino acids include amino acids having apolar side chains. Apolar amino acids may be further subdivided to include, among others, aliphatic amino acids. The definitions of the classes of amino acids as used herein are as follows:

"Hydrophobic amino acid" refers to an amino acid having a side chain that is uncharged at physiological pH and that is repelled by aqueous solution. Examples of genetically encoded hydrophobic amino acids include Ala, Ile, Leu and Val. Examples of non-genetically encoded hydrophobic amino acids include t-BuA.

"Aromatic amino acid" refers to a hydrophobic or hydrophilic amino acid having a side chain containing at least one ring having a conjugated π-electron system (aromatic group). The aromatic group may be further substituted with substituent groups such as alkyl, alkenyl, alkynyl, hydroxyl, sulfonyl, nitro and amino groups, as well as others. Examples of genetically encoded aromatic amino acids include phenylalanine, tyrosine and tryptophan. Commonly encountered non-genetically encoded aromatic amino acids include phenylglycine, 2-naphthylalanine, β-2-thienylalanine, 1,2,3,4-tetrahydroisoquinoline-3-carboxylic acid, 4-chlorophenylalanine, 2-fluorophenylalanine, 3-fluorophenylalanine and 4-fluorophenylalanine.

"Apolar amino acid" refers to a hydrophobic amino acid having a side chain that is generally uncharged at physiological pH and that is not polar. Examples of genetically encoded apolar amino acids include proline and methionine. Examples of non-encoded apolar amino acids include Cha.

"Aliphatic amino acid" refers to an apolar amino acid having a saturated or unsaturated straight chain, branched or cyclic hydrocarbon side chain. Examples of genetically encoded aliphatic amino acids include Ala, Leu, Val and Ile. Examples of non-encoded aliphatic amino acids include Nle.

"Hydrophilic amino acid" refers to an amino acid having a side chain that is attracted by aqueous solution. Examples of genetically encoded hydrophilic amino acids include Ser and Lys. Examples of non-encoded hydrophilic amino acids include Cit and hCys.

"Acidic amino acid" or "negatively charged amino acid" refers to a hydrophilic amino acid having a side chain pK value of less than 7. Acidic amino acids typically have negatively charged side chains at physiological pH due to loss of a hydrogen ion. Examples of genetically encoded acidic amino acids include aspartic acid (aspartate) and glutamic acid (glutamate).

"Basic amino acid" refers to a hydrophilic amino acid having a side chain pK value of greater than 7. Basic amino acids typically have positively charged side chains at physiological pH due to association with hydronium ion. Examples of genetically encoded basic amino acids include arginine, lysine and histidine. Examples of non-genetically encoded basic amino acids include the non-cyclic amino acids ornithine, 2,3-diaminopropionic acid, 2,4-diaminobutyric acid and homoarginine.

"Polar amino acid" refers to a hydrophilic amino acid having a side chain that is uncharged at physiological pH, but where a bond in the side chain has a pair of electrons that are held more closely by one of the atoms involved in the bond. Examples of genetically encoded polar amino acids include asparagine and glutamine. Examples of non-genetically encoded polar amino acids include citrulline, N-acetyl lysine and methionine sulfoxide.

"Cysteine-like amino acid" refers to an amino acid having a side chain capable of forming a covalent linkage with a side chain of another amino acid residue, such as a disulfide linkage. Typically, cysteine-like amino acids generally have a side chain containing at least one thiol (SH) group. An example of a genetically encoded cysteine-like amino acid is cysteine. Examples of non-genetically encoded cysteine-like amino acids include homocysteine and penicillamine.

As will be appreciated by those having skill in the art, the above classifications are not absolute. Several amino acids exhibit more than one characteristic property, and can therefore be included in more than one category. For example, tyrosine has both an aromatic ring and a polar hydroxyl group. Thus, tyrosine has dual properties and can be included in both the aromatic and polar categories. Similarly, in addition to being able to form disulfide linkages, cysteine also has an apolar character. Thus, while not strictly classified as a hydrophobic or an apolar amino acid, in many instances cysteine can be used to confer hydrophobicity to a peptide.

Certain commonly encountered amino acids that are not genetically encoded and that can be present, or substituted for an amino acid, in the peptides, peptide variants and peptide derivatives of the invention include, but are not limited to, β-alanine (b-Ala) and other omega-amino acids such as 3-aminopropionic acid (Dap), 2,3-diaminopropionic acid (Dpr), 4-aminobutyric acid and so forth; α-aminoisobutyric acid (Aib); ε-aminohexanoic acid (Aha); δ-aminovaleric acid (Ava); N-methylglycine (MeGly); ornithine (Orn); citrulline (Cit); t-butylalanine (t-BuA); t-butylglycine (t-BuG); N-methylisoleucine (MeIle); phenylglycine (Phg); cyclohexylalanine (Cha); norleucine (Nle); 2-naphthylalanine (2-Nal); 4-chlorophenylalanine (Phe(4-Cl)); 2-fluorophenylalanine (Phe(2-F)); 3-fluorophenylalanine (Phe(3-F)); 4-fluorophenylalanine (Phe(4-F)); penicillamine (Pen); 1,2,3,4-tetrahydroisoquinoline-3-carboxylic acid (Tic); β-2-thienylalanine (Thi); methionine sulfoxide (MSO); homoarginine (hArg); N-acetyl lysine (AcLys); 2,3-diaminobutyric acid (Dab); 2,3-diaminobutyric acid (Dbu); p-aminophenylalanine (Phe (pNH$_2$)); N-methyl valine (MeVal); homocysteine (hCys) and homoserine (hSer). These amino acids also fall into the categories defined above.

The classifications of the above-described genetically encoded and non-encoded amino acids are summarized in Table 2, below. It is to be understood that Table 2 is for illustrative purposes only and does not purport to be an exhaustive list of amino acid residues that may comprise the peptides, variants and derivatives described herein. Other amino acid residues that are useful for making the peptides, peptide variants and peptide derivatives described herein can be found, e.g., in Fasman, 1989, CRC Practical Handbook of Biochemistry and Molecular Biology, CRC Press, Inc., and the references cited therein. Amino acids not specifically mentioned herein can be conveniently classified into the above-described categories on the basis of known behavior and/or their characteristic chemical and/or physical properties as compared with amino acids specifically identified.

TABLE 2

| Classification | Genetically Encoded | Genetically Non-Encoded |
| --- | --- | --- |
| Hydrophobic | | |
| Aromatic | F, Y, W | Phg, Nal, Thi, Tic, Phe(4-Cl), Phe(2-F), Phe(3-F), Phe(4-F), Pyridyl Ala, Benzothienyl Ala |
| Apolar | M, G, P | Cha |
| Aliphatic | A, V, L, I | t-BuA, t-BuG, MeIle, Nle, MeVal, Cha, bAla, MeGly, Aib |
| Hydrophilic | | |
| Acidic | D, E | |
| Basic | H, K, R | Dpr, Orn, hArg, Phe(p-NH$_2$), DBU, A$_2$ BU |
| Polar | Q, N, S, T, Y | Cit, AcLys, MSO, hSer |
| Cysteine-Like | C | Pen, hCys, β-methyl-Cys |

Nanowire peptides of the invention with modified conductive properties can have any amino acid replaced by tyrosine, tryptophan, or a charged amino acid. Alternatively, nanowire peptides of the invention with modified conductive properties can have any tyrosine, tryptophan, or a charged amino acid within the nanowire peptide replaced by another amino acid.

Amino acid modifications that can diminish or abolish conductivity include single, double and triple replacements in tyrosines (e.g., replaced with alanine or the structurally-similar phenylalanine as shown herein) and/or positively and negatively charged amino acids.

Amino acid modifications that can increase conductivity include replacements that introduce additional tyrosines in optimum positions within the nanowire to promote electron transfer. Furthermore, replacements that result in structural changes that permit a more optimal electronic coupling between the electroactive amino acids (e.g., by bringing closer together) can also be used because they may increase the rates of electron hopping. These amino acids can be those directly involved in the electron transfer, such as tyrosines, those serving as protonating or proton-accepting residues, or those that preserve the optimal nanowire structure to promote electron transfer.

In addition, amino acids carrying post-translational modifications such as glycosylation, acylation or phosphorylation can be also introduced or replaced to manipulate the binding and adhesive properties of the nanowires, the charge of the nanowires and the electronic behavior of the nanowires. Amino acids that are post-translationally modified can be replaced, added, or used instead of an existing amino acid within any of the SEQ ID NO:1-10 peptides. For example, an amino acid subject to posttranslational modification, such as phosphorylation, glycosylation or acylation, can be used instead of an existing amino acid within any of SEQ ID NO: 1-10. Alternatively, an amino acid that is not post-translationally modified can be replaced with another amino acid that is post-translationally modified. In some embodiments, the amino acid is replaced with a similarly classified amino acid to minimize changes in the secondary or tertiary structure of the nanowire peptide.

In some embodiments, a cysteine or cysteine-like amino acid is added to a nanowire peptide having a sequence like any of SEQ ID NO: 1-10. Alternatively, the cysteine or cysteine-like amino acid is used instead of an amino acid present in a nanowire peptide having a sequence like any of SEQ ID NO:1-10. Such a cysteine or cysteine-like amino acid is useful for enhancing the binding or adhesion properties of the nanowire peptide. For example, preliminary results indicate that placement or addition of cysteine in nanowire peptides facilitates electrical coupling of the nanowire peptide to substrates containing gold. In some embodiments, the cysteine or cysteine-like amino acid is placed within or near the C-terminal region of the nanowire sequence.

In some embodiments, the nanowire polypeptides have a signal sequence; in other embodiments, the nanowire polypeptides do not have a signal sequence. As used herein, "signal sequence" or "signal peptide" refers to a peptide that can be used to secrete the heterologous polypeptide into the periplasm of the bacteria. The signal for the heterologous polypeptide may be homologous to the bacteria, or they may be heterologous, including signals native to the polypeptide being produced in the bacteria.

In some embodiments of the invention, the nanowire polypeptide is selected from the following group: (1) a polypeptide having an amino acid sequence as shown in any of SEQ NO: 1-10; or (2) a polypeptide having an amino acid sequence with at least 70% identity to that of any of SEQ ID NO: 1-10, the polypeptide having conductive function or activity compared to that of the polypeptide of (1); or (3) a functional fragment, variant, analog or derivative of the polypeptide of (1) or (2), having substantially the same biological function or activity comparing to that of the polypeptide of (1) or (2). In some embodiments, the nanowire polypeptides contain an amino acid sequence with identity of at least 75%, or at least 80%, preferably at least 85%, preferably at least 90%, preferably at least 95%, more preferably at least 96%, at least 97%, at least 98% and/or at least 99% relative to any of SEQ NO: 1-10.

As used herein, the term "polypeptide" refers to at least two amino acid residues connected as a chain via covalent bonds such as peptide bonds, and can be recombinant polypeptides, natural polypeptides or synthetic polypeptides. The terms "polypeptide," "peptide" and "protein" are used interchangeably herein.

The pilus nanowires are described further in the Examples. As described herein, the purified pilus nanowire polypeptides, when stripped of associated proteins (such as c-cytochromes), metalloproteins, metals, ions, contaminants and redox cofactors such as flavins and quinones are electrically conductive and behave as molecular rectifiers (asymmetric conductivity).

Manipulation of Nucleic Acids Encoding Nanowire Polypeptides

Nucleic acids encoding modified nanowire polypeptides are useful for recombinant expression of the modified nanowire polypeptides. Nucleic acids encoding modified nanowire polypeptides can be generated from nucleic acids encoding the naturally-occurring nanowire (e.g., pilA) nucleic acids using methods known to those of skilled in the art.

Any available nanowire nucleic acid can form the basis for generating mutant nucleic acids that encode nanowires with modified properties. For example, Geobacteraceae bacteria naturally produce nanowire protein filaments that are electrically conductive. Hence, Geobacteraceae bacteria are one source of nanowire nucleic acids. Natural nucleic acid sequences, such those encoding the SEQ ID NO:1-10 nanowire polypeptides, can act as a basis for generating modified nanowire polypeptides. Naturally-occurring nanowire nucleic acid and amino acid sequences are also available in public sequence databases such as those provided by the National Center for Biotechnology Information (NCBI) database (see, e.g., the website at www.ncbi.nlm.nih.gov).

For example, the SEQ ID NO:9 and 10 nanowire polypeptides are encoded by the following pilA nucleic acid sequence (SEQ ID NO: 11), which can be used to generate mutant nanowire nucleic acids.

```
  1    ATG CTT CAG AAA CTC AGA AAC AGG AAA GGT
 31    TTC ACC CTT ATC GAG CTG CTG ATC GTC GTT
 61    GCG ATC ATC GGT ATT CTC GCT GCA ATT GCG
 91    ATT CCG CAG TTC TCG GCG TAT CGT GTC AAG
121    GCG TAC AAC AGC GCG GCG TCA AGC GAC TTG
151    AGA AAC CTG AAG ACT GCT CTT GAG TCC GCA
181    TTT GCT GAT GAT CAA ACC TAT CCG CCC GAA
211    AGT TAA
```

In some of the embodiments, the nucleic acids that encode nanowire polypeptides have sequence identity with the SEQ ID NO: 11 nucleic acid sequence of at least 70%, at least 75%, at least 80%, at least 85%, at least 90%, at least 95%, at least 96%, at least 97%, at least 98% and/or at least 99%.

For example, nucleic acids can readily be generated that encode mutant nanowire polypeptides, where in some embodiments, the mutant nucleic acids encode nanowire polypeptides that include less than the three tyrosine amino acids at positions 27, 32 and 57 of the SEQ ID NO:9 nanowire polypeptide. Such 'tyrosine-deficient' nanowire polypeptides have reduced conductivity, as illustrated herein. In other embodiments, the mutant nucleic acids encode nanowire polypeptides that include more than the three tyrosine amino acid residues at amino acid positions 27, 32 or 57. Such 'tyrosine-rich' nanowire polypeptides can have increased conductivity. In some embodiments, the mutant nanowire polypeptides have 2, 3, 4, 5, 6, 7, 8, 9, 10, 11, 12, 13 or 14 tyrosine residues.

In some embodiments, the mutant nucleic acids encode nanowire polypeptides that include fewer negatively charged amino acids than are typically present at positions 5, 39, 48, 53, 54 and 60 of the SEQ ID NO:9 nanowire polypeptide. In other embodiments, the mutant nucleic acids encode nanowire polypeptides that include more negatively charged amino acids than are typically present at positions 5, 39, 48, 53, 54 and 60 of the SEQ ID NO:9 nanowire polypeptide. Thus, the mutant nanowire polypeptides can, for example, have 3, 4, 5, 6, 7, 8, 9, 10, 11, 12, 13 or 14 negatively charged amino acids (e.g., aspartic acid or glutamic acid).

In some embodiments, the mutant nucleic acids encode nanowire polypeptides that include fewer positively charged amino acids than are typically present at positions 28, 30, 41 and 44 of the SEQ ID NO:9 nanowire polypeptide. In other embodiments, the mutant nucleic acids encode nanowire polypeptides that include more positively charged amino acids than are typically present at positions 28, 30, 41 and 44 of the SEQ ID NO:9 nanowire polypeptide. Thus, the mutant nanowire polypeptides can, for example, have 2, 3, 4, 5, 6, 7, 8, 9, 10, 11, 12, 13 or 14 positively charged amino acids (e.g., aspartic acid or glutamic acid).

In many embodiments, the modified nanowire polypeptides recombinantly generated from the mutant nucleic acids have substantially the same secondary and/or tertiary structure(s) as naturally occurring nanowire polypeptides (e.g., the SEQ ID NO:1-10 polypeptides).

Methods for isolating nucleic acids encoding the naturally-occurring nanowires, as well as technologies for generation of nucleic acids encoding modified nanowire polypeptides are available in the art. See, for example, CURRENT PROTOCOLS IN MOLECULAR BIOLOGY, Ausubel et al. eds. (John Wiley & Sons, Inc., 1999), or MOLECULAR CLONING: A LABORATORY MANUAL, Sambrook et al. (Cold Spring Harbor Laboratory Press, New York, 1989), or MOLECULAR CLONING: A LABORATORY MANUAL, Sambrook et al. (Cold Spring Harbor Laboratory Press, New York, 2001). Nucleic acids encoding mutant nanowire polypeptides containing various amino acid substitutions can be produced by site-specific mutagenesis and polymerase chain reaction (PCR) amplification from the nucleic acids encoding the naturally-occurring pilin. Stratagene provides a QuikChange mutagenesis kit that can be used for such mutagenesis. Complementary primers containing mutagenic nucleotides can be employed such as those described in the Examples provided herein. Mutant nucleic acids that encode such modified nanowires can be produced, for example, by polymerase chain reaction (PCR) using primers that encode the desired sequence.

In some embodiments of the invention, the nanowire polypeptide is selected from the following group: (1) a polypeptide having an amino acid sequence as shown in any of SEQ NO: 1-10; or (2) a polypeptide having an amino acid sequence with at least 40% sequence identity to that of any of SEQ ID NO: 1-10, the polypeptide having conductive function or activity compared to that of the polypeptide of (1); or (3) a functional fragment, variant, analog or derivative of the polypeptide of (1) or (2), having substantially the same biological function or activity comparing to that of the polypeptide of (1) or (2), wherein the polynucleotides include: (a) polynucleotides that code the PilA polypeptides of (1), (2) or (3) above; (b) polynucleotides that are hybridized with, under low, medium or high stringent conditions, and have at least 40% of sequence identity compared to the polynucleotides of (a); and (c) polynucleotide fragments that contain polynucleotides as described in (a) and (b).

The terms "stringent conditions" or "stringent hybridization conditions" include conditions under which a probe will hybridize to its target sequence to a detectably greater degree than other sequences (e.g., at least 2-fold over background). Stringent conditions are somewhat sequence-dependent and can vary in different circumstances. By controlling the stringency of the hybridization and/or washing conditions, target sequences can be identified which can be up to 100% complementarity to the probe (homologous probing). Alternatively, stringency conditions can be adjusted to allow some mismatching in sequences so that lower degrees of similarity are detected (heterologous probing). The probe can be approximately 20-500 nucleotides in length, but can vary greatly in length from about 18 nucleotides to equal to the entire length of the target sequence. In some embodiments, the probe is about 10-50 nucleotides in length, or about 18-25 nucleotides in length, or about 18-50 nucleotides in length, or about 18-100 nucleotides in length. In some embodiments, the probe is a full length nucleic acid with SEQ ID NO: 11 (which has 216 nucleotides), or a fragment thereof.

Typically, stringent conditions will be those where the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide or Denhardt's. Exemplary low stringency conditions include hybridization with a buffer solution of 30 to 35% formamide, 1M NaCl, 1% SDS (sodium dodecyl sulfate) at 37° C., and a wash in 1×SSC to 2×SSC (where 20×SSC is 3.0 M NaCl, 0.3 M trisodium citrate) at 50 to 55° C. Exemplary moderate stringency conditions include hybridization in 40 to 45% formamide, 1M NaCl, 1% SDS at 37° C., and a wash in 0.5×SSC to 1×SSC at 55 to 60° C. Exemplary high stringency conditions include hybridization in 50% formamide, 1M NaCl, 1% SDS at 37° C., and a wash in 0.1×SSC at 60 to 65° C. Specificity is typically the function of post-hybridization washes, the critical factors being the ionic strength and temperature of the final wash solution. For DNA-DNA hybrids, the $T_m$ can be approximated from the equation of Meinkoth and Wahl (Anal. Biochem. 138:267-84 (1984)):

$$T_m = 81.5°\ C. + 16.6(\log M) + 0.41(\%\ GC) - 0.61(\%\ \text{formamide}) - 500/L$$

where M is the molarity of monovalent cations; % GC is the percentage of guanosine and cytosine nucleotides in the DNA, % formamide is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. The $T_m$ is reduced by about 1° C. for each 1% of mismatching. Thus, the $T_m$, hybridization and/or wash conditions can be adjusted to hybridize to sequences of the desired identity. For example, if sequences with greater than or equal to 90% sequence identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3 or 4° C. lower than the thermal melting point ($T_m$). Moderately stringent conditions can utilize a hybridization and/or a wash at 6, 7, 8, 9 or 10° C. lower than the thermal melting point ($T_m$). Low stringency conditions can utilize a hybridization and/or wash at 11, 12, 13, 14, 15 or 20° C. lower than the thermal melting point ($T_m$). Using the equation, hybridization and wash compositions, and desired $T_m$, those of ordinary skill can identify and isolate nucleic acids with sequences related to SEQ ID NO:1. Those of skill in the art also understand how to vary the hybridization and/or wash solutions. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, LABORATORY TECHNIQUES IN BIOCHEMISTRY AND MOLECULAR BIOLOGY— HYBRIDIZATION WITH NUCLEIC ACID PROBES, part 1, chapter 2, "Overview of principles of hybridization and the strategy of nucleic acid probe assays," Elsevier, N.Y. (1993); and CURRENT PROTOCOLS IN MOLECULAR BIOLOGY, chapter 2, Ausubel, et al., eds, Greene Publishing and Wiley-Interscience, New York (1995). Unless otherwise stated, in the present application high stringency is defined as hybridization in 4×SSC, 5×Denhardt's (5 g Ficoll, 5 g polyvinypyrrolidone, 5 g bovine serum albumin in 500 ml of water), 0.1 mg/ml boiled salmon sperm DNA, and 25 mM Na phosphate at 65° C., and a wash in 0.1×SSC, 0.1% SDS at 65° C.

The following terms are used to describe the sequence relationships between two or more nucleic acids or nucleic acids or polypeptides: (a) "reference sequence," (b) "comparison window," (c) "sequence identity," (d) "percentage of sequence identity" and (e) "substantial identity."

As used herein, "reference sequence" is a defined sequence used as a basis for sequence comparison. The reference sequence can be a nucleic acid sequence (e.g., SEQ ID NO: 11) or an amino acid sequence (e.g., any of SEQ ID NO:1-10). A reference sequence may be a subset or the entirety of a specified sequence; for example, as a segment of a full-length cDNA or genomic DNA sequence, or the complete cDNA or genomic DNA sequence, or a domain of a polypeptide sequence.

As used herein, "comparison window" refers to a contiguous and specified segment of a nucleic acid or an amino acid sequence, wherein the nucleic acid/amino acid sequence may be compared to a reference sequence and wherein the portion of the nucleic acidamino acid sequence in the comparison window may comprise additions or deletions (i.e., gaps) compared to the reference sequence (which does not comprise additions or deletions) for optimal alignment of the two sequences. The comparison window can vary for nucleic acid and polypeptide sequences. Generally, for nucleic acids, the comparison window is at least 20 contiguous nucleotides in length, and optionally can be 30, 40, 50, 100 or more nucleotides. For amino acid sequences, the comparison window is at least about 15 amino acids, and can optionally be 20, 30, 40, 50, 100 or more amino acids. Those of skill in the art understand that to avoid a high similarity to a reference sequence due to inclusion of gaps in the nucleic acid or amino acid sequence a gap penalty is typically introduced and is subtracted from the number of matches.

Methods of alignment of nucleotide and amino acid sequences for comparison are well known in the art. The local homology algorithm (BESTFIT) of Smith and Waterman, (1981) Adv. Appl. Math 2:482, may conduct optimal alignment of sequences for comparison; by the homology alignment algorithm (GAP) of Needleman and Wunsch, (1970) J. Mol. Biol. 48:443-53; by the search for similarity method (Tfasta and Fasta) of Pearson and Lipman, (1988) Proc. Natl. Acad. Sci. USA 85:2444; by computerized implementations of these algorithms, including, but not limited to: CLUSTAL in the PC/Gene program by Intelligenetics, Mountain View, Calif., GAP, BESTFIT, BLAST, FASTA and TFASTA in the Wisconsin Genetics Software Package, Version 8 (available from Genetics Computer Group (GCG™ programs (Accelrys, Inc., San Diego, Calif.)). The CLUSTAL program is well described by Higgins and Sharp, (1988) Gene 73:237-44; Higgins and Sharp, (1989) CABIOS 5:151-3; Corpet, et al., (1988) Nucleic Acids Res. 16:10881-90; Huang, et al., (1992) Computer Applications in the Biosciences 8:155-65 and Pearson, et al., (1994) Meth. Mol. Biol. 24:307-31. The preferred program to use for optimal global alignment of multiple sequences is PileUp (Feng and Doolittle, (1987) J. Mol. Evol., 25:351-60 which is similar to the method described by Higgins and Sharp, (1989) CABIOS 5:151-53 and hereby incorporated by reference). The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, Current Protocols in Molecular Biology, Chapter 19, Ausubel, et al., eds., Greene Publishing and Wiley-lnterscience, New York (1995).

GAP uses the algorithm of Needleman and Wunsch, (1970) J. Mol. Biol. 48:443-53, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package are 8 and 2, respectively. The gap creation and gap extension penalties can be expressed as an integer selected from the group of integers consisting of from 0 to 100. Thus, for example, the gap creation and gap extension penalties can be 0, 1, 2, 3, 4, 5, 6, 7, 8, 9, 10, 15, 20, 30, 40, 50 or greater.

GAP presents one member of the family of best alignments. There may be many members of this family, but no other member has a better quality. GAP displays four figures of merit for alignments: Quality, Ratio, Identity and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see, Henikoff and Henikoff, (1989) Proc. Natl. Acad. Sci. USA 89:10915).

Unless otherwise stated, sequence identity/similarity values provided herein refer to the value obtained using the BLAST 2.0 suite of programs using default parameters (Altschul, et al., (1997) Nucleic Acids Res. 25:3389-402).

As those of ordinary skill in the art will understand, BLAST searches assume that proteins can be modeled as random sequences. However, many real proteins comprise regions of nonrandom sequences, which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen (1993) Comput. Chem. 17:149-63) and XNU (C.sub.1-ayerie and States, (1993) Comput. Chem. 17:191-201) low-complexity filters can be employed alone or in combination.

The terms "substantial identity" indicates that a polypeptide or nucleic acid comprises a sequence with between 55-100% sequence identity to a reference sequence, preferably at least 55% sequence identity, preferably 60%, preferably 70%, more preferably 80%, most preferably at least 90% or 95% sequence identity to the reference sequence over a specified comparison window. The reference sequence can, for example, be any of the SEQ ID NO:1-10 nanowire polypeptides or the SEQ ID NO: 11 nanowire nucleic acid. Optimal alignment may be ascertained or conducted using the homology alignment algorithm of Needleman and Wunsch, supra.

Expression of Nanowire Polypeptides

Nucleic acids encoding nanowire polypeptides can be used for recombinant expression of the nanowire polypeptides, for example, by operably-linking the nanowire nucleic acid to an expression control sequence within an expression vector, which can be introduced into a host cell for expression of the encoded polypeptide.

As used herein, the term "operably linked" means that a nucleic acid and an expression control sequence are positioned in such a way that the expression control sequence directs expression of the nucleic acid under appropriate culture conditions and when the appropriate molecules such as RNA transcriptional proteins are bound to the expression control sequence.

The term "expression control sequence" refers to a nucleic acid sequence sufficient to direct the transcription of another nucleic acid sequence that is operably linked to the expression control sequence to produce an RNA transcript.

An "expression vector" is a nucleic acid molecule capable of transporting and/or allowing for the expression of another nucleic acid to which it has been linked. Expression vectors contain appropriate expression control sequences that direct expression of a nucleic acid that is operably linked to the expression control sequence to produce a transcript. The product of that expression is referred to as a messenger ribose nucleic acid (mRNA) transcript. The expression vector may also include other sequences such as enhancer sequences, synthetic introns, and polyadenylation and transcriptional termination sequences to improve or optimize expression of the nucleic acid encoding the nanowire polypeptide.

The nanowire nucleic acid(s) can be optimized for expression in a selected prokaryotic (e.g., bacterial) or eukaryotic cell. As is known to one of skill in the art, a particular type of bacterial or animal species may have a different set of preferred codons than another type of species. Use of codons that are preferred by a host cell can facilitate expression of the nanowire polypeptides. Optimized sequences include sequences that are codon optimized to include codons that are employed more frequently in one organism relative to another organism, as well as modifications to add or modify Kozak sequences, to add or remove introns, and/or to remove undesirable sequences, for instance, potential transcription factor binding sites.

In one embodiment, a nucleic acid sequence encoding nanowire is optimized by replacing codons in a nanowire nucleic acid with codons that encode the same (or similar) amino acid but are preferentially employed in a particular (selected) cell. Preferred codons have a relatively high codon usage frequency in a selected cell (e.g. a bacterial, yeast or animal cell) and are translated more efficiently. Introduction of preferred codons can also result in the introduction of only selected transcription factor binding sites for transcription factors present in the selected host cell, and relatively few other undesirable structural attributes. Thus, the optimized nucleic acid product has an improved level of expression due to improved codon usage frequency, and a reduced risk of inappropriate transcriptional behavior due to a reduced number of undesirable transcription regulatory sequences.

In one embodiment, the optimized nucleic acid no longer hybridizes to the corresponding non-optimized sequence, e.g., does not hybridize to the non-optimized sequence under medium or high stringency conditions. However, in most embodiments, the optimized nucleic acid does hybridize to the corresponding non-optimized sequence under medium or high stringency conditions. In another embodiment, the nucleic acid has less than 90%. e.g., less than 80%, nucleic acid sequence identity to the corresponding non-optimized sequence and optionally encodes a polypeptide having at least 80%, e.g., at least 85%, 90%, 91%, 92%, 93%, 94%, 95%, 96%, 97%, 98% or more, amino acid sequence identity with the polypeptide encoded by the non-optimized sequence.

An isolated and optimized nucleic acid molecule of the invention may have a codon composition that differs from that of the corresponding wild type nucleic acid sequence at more than 30%, 35%, 40% or more than 45%, e.g., 50%, 55%, 60% or more of the codons. For example, when a non-bacterial host cell is used, the preferred codons are those that are employed more frequently in a selected non-bacterial host cell species than, for example, in the genome of a *Geobacter* species. In general, preferred codons do not include codons that are infrequently used in the selected organism or cell type. Preferred codons for different organisms are known to the art, e.g., see www.kazusa.or.jp./codon/. In one embodiment of the invention, the majority of the codons that differ are ones that are preferred codons in a desired host cell.

A nucleic acid molecule encoding a nanowire polypeptide can optionally be optimized for expression in a particular host cell and then operably linked to one or more transcription regulatory sequences, e.g., a promoter, one or more enhancers, a transcription termination sequence or a combination thereof, to form an expression cassette.

Nucleic acids encoding nanowire polypeptides of the invention can be incorporated into bacterial, viral, insect, yeast or mammalian expression vectors so that they are operably-linked to expression control sequences such as bacterial, viral, insect, yeast or mammalian promoters (and/or enhancers).

Nucleic acid molecules or expression cassette that encode nanowire polypeptides may be introduced to a vector, e.g., a plasmid or viral vector, which optionally includes a selectable marker gene, and the vector introduced to a cell of interest, for example, a bacterial, yeast or mammalian cell. In some embodiments, the vector may be maintained, manipulated, expanded or replicated in a prokaryotic cell such as a cell from the family Geobacteraceae or a cell from the genus

*Geobacter*. In other embodiments, the vector may be maintained, manipulated, expanded or replicated in a prokaryotic cell such as an *E. coli, Streptomyces* spp., *Bacillus* spp., *Staphylococcus* spp. and the like. In further embodiments, the vector may be maintained, manipulated, expanded or replicated in a eukaryotic cell such as a yeast or mammalian cell. In some preferred embodiments, the host cell is the bacterium *Geobacter sulfurreducens*. Expression vectors containing nucleic acids encoding nanowire polypeptides can be introduced into bacterial, insect, yeast or mammalian host cells for expression using conventional methods including, without limitation, transformation, transduction and transfection. In some embodiments, the host cell also has a pilB and/or pilT gene, which may facilitate, respectively, assembly and extension and/or retraction of the nanowire polypeptide(s). In other embodiments, the host cell has no pilT gene, or carries a deletion in the pilT gene, to inhibit retraction of the nanowire polypeptide(s) and facilitate assembly of the nanowire filament.

The expression of the encoded nanowire protein may be controlled by any promoter capable of expression in prokaryotic cells or eukaryotic cells. Examples of prokaryotic promoters that can be used include, but are not limited to, SP6, T7, T5, tac, bla, trp, gal, lac or maltose promoters. Examples of eukaryotic promoters that can be used include, but are not limited to, constitutive promoters, e.g., viral promoters such as CMV, SV40 and RSV promoters, as well as regulatable promoters, e.g., an inducible or repressible promoter such as the tet promoter, the hsp70 promoter and a synthetic promoter regulated by CRE. Vectors for bacterial expression include pGEX-5X-3, and for eukaryotic expression include pCIneo-CMV. In some embodiments, the expression vector is the pRG5 vector (Coppi et al., *Appl. Environ. Microbiol.* 67: 3180-87 (2001)); Leang et al., *BMC Genomics* 10, 331 (2009).

In many embodiments, the nanowire polypeptides are expressed in a bacterial host cell. Plasmid vectors containing bacterial replicon and control sequences are typically used for expression in a bacterial host cell. The vector ordinarily carries a replication site, as well as marking sequences that are capable of providing phenotypic selection in transformed cells. For example, *E. coli* is typically transformed using pBR322, a plasmid derived from an *E. coli* species. See, e.g., Bolivar et al., Gene 2: 95 (1977). pBR322 contains genes conferring ampicillin and tetracycline resistance and thus provides an easy means for identifying transformed cells. The pBR322 plasmid, or other microbial plasmid or phage, also generally contains, or is modified to contain, promoters that can be used by the bacterial organism for expression of the selectable marker genes.

Bacterial expression vectors for producing a nanowire polypeptide can also contain an inducible promoter that is recognized by the host bacterial organism and is operably linked to the nucleic acid encoding the polypeptide of interest. It can also contain a separate promoter, which may be inducible or of low basal expression, operably linked to the nucleic acid encoding the phage lysozyme. Inducible promoters suitable for use with bacterial hosts include the β-lactamase and lactose promoter systems (Chang et al., Nature 275: 615 (1978); Goeddel et al., Nature 281: 544 (1979)), the arabinose promoter system, including the araBAD promoter (Guzman et al., J. Bacteriol. 174: 7716-7728 (1992); Guzman et al., J. Bacteriol. 177: 4121-4130 (1995); Siegele and Hu Proc. Natl. Acad. Sci. USA, 94: 8168-8172 (1997)), the rhamnose promoter (Haldimann et al., J. Bacteriol., 180: 1277-1286 (1998)), the alkaline phosphatase promoter, a tryptophan (trp) promoter system (Goeddel, Nucleic Acids Res., 8: 4057 (1980) and EP 36,776), the $P_{LtetO-1}$ and $P_{lac}/_{ara-1}$ promoters (Lutz and Bujard, Nucleic Acids Res., 25: 1203-1210 (1997)), and hybrid promoters such as the tac promoter (deBoer et al., Proc. Natl. Acad. Sci. USA, 80: 21-25 (1983)). However, other bacterial inducible and low-basal-expression promoters are suitable, including promoter nucleotide sequences that have been published, thereby enabling a skilled worker operably to ligate them to DNA encoding the polypeptide of interest using linkers or adaptors to supply any required restriction sites. For example, a strong and highly leaky promoter, such as the trp promoter, can be employed. The phage lambda $P_L$ promoter and/or the alkaline phosphatase promoter can also be used.

Promoters for use in bacterial systems also generally contain a Shine-Dalgarno (S.D.) sequence operably linked to the DNA encoding the polypeptide of interest. The promoter can be removed from the bacterial source DNA by restriction enzyme digestion and inserted into the vector containing the desired DNA. The phoA promoter can be removed from the bacterial-source DNA by restriction enzyme digestion and inserted into the vector containing the desired DNA.

The nucleic acid encoding the nanowire polypeptide may contain a signal sequence, such as one at the N-terminus of the mature polypeptide. The signal sequence may be a component of the vector, or it may be a part of the polypeptide nucleic acid that is inserted into the vector. If a heterologous signal sequence is selected it should be one that is recognized and processed (i.e., cleaved by a signal peptidase) by the host cell.

Expression vectors contain a nucleic acid sequence that enables the vector to replicate in one or more selected host cells. Such sequences are well known for a variety of bacteria. The origin of replication from the plasmid pBR322 is suitable for most Gram-negative bacteria.

Expression vectors can also contain a selection gene, also termed a selectable marker. This gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for bacilli. One example of a selection scheme utilizes a drug to arrest growth of a host cell. Those cells that are successfully transformed with a heterologous gene produce a protein conferring drug resistance and thus survive the selection regimen.

Construction of suitable vectors containing one or more of the above-listed components employs standard ligation techniques. Isolated plasmids or DNA fragments are cleaved, tailored, and re-ligated in the form desired to generate the plasmids required. For analysis to confirm correct sequences in plasmids constructed, the ligation mixtures can be transformed into *Geobacter, E. coli* K12 strain 294 (e.g., ATCC 31,446), or other strains, and successful transformants are selected. Plasmids from the transformants can be prepared, analyzed by restriction endonuclease digestion, and/or sequenced by available procedures.

The nanowire nucleic acid molecule, expression cassette and/or vector of the can be introduced to a cell by any method including, but not limited to, calcium-mediated transformation, electroporation, microinjection, lipofection, particle bombardment and the like.

Suitable bacteria for expression of the nanowire polypeptides include host cells that also have or are modified to include a pilT gene. Such host cells include, for example, archeabacteria and bacteria, especially Gram-negative bacteria. For example, Gram-negative bacteria such as Geobacteraceae or Enterobacteriaceae can be utilized as host cells. Examples of useful bacteria include *Geobacter, Escherichia, Enterobacter, Azotobacter, Erwinia, Bacillus, Pseudomonas, Klebsiella, Proteus, Salmonella, Serratia, Shigella, Rhizobia, Vitreoscilla*, and *Paracoccus*. Suitable *E. coli* hosts include *E. coli* W3110 (ATCC 27,325), *E. coli* 294 (ATCC 31,446), *E. coli* B, and *E. coli* X1776 (ATCC 31,537). These examples are illustrative rather than limiting. Mutant cells of any of the above-mentioned bacteria may also be employed. It is, of course, necessary to select the appropriate bacteria taking into consideration replicability of the replicon in the cells of a bacterium. For example, *Geobacter, E. coli, Serratia*, or *Salmonella* species can be suitably used as the host cells when well-known plasmids such as pBR322, pBR325, pACYC177, or pKN410 are used to supply the replicon.

The host cells containing the nanowire nucleic acid(s) can be expanded in culture using available procedures and cell culture conditions. In some embodiments, pilus nanowires are produced by Geobacteraceae bacteria that have the pilB gene and the pilT gene (or, alternatively, a deletion of an endogenous pilT gene). The culture medium can be a Fresh Water (FW) medium with acetate and fumarate, which is described by Reguera et al. (NATURE 435: 1098-1101 (2005); Reguera et al., J. BACTERIOL. 189: 2125-27 (2007); U.S. Pat. No. 7,498,155, which are herein incorporated by reference in their entireties). The host cells can be cultured at different temperatures, for example, at 20-30° C. (e.g., 25° C.).

Nanowire polypeptides can also be expressed in the absence of Fe(Ill) oxides when grown under suboptimal growth conditions analogous to those that Geobacteraceae would naturally encounter in environment. Pili production may not be specifically associated with the presence of metal oxides in their culture environment, but rather may be due to the physiological state(s) associated with suboptimal growth, which occurs at lower temperatures, during growth transitions, and when Geobacteraceae have to use insoluble electron acceptors.

Expression of nanowires in the absence of Fe(III) oxides and at suboptimal growth temperatures also causes the cells to agglutinate, indicating that the nanowires may participate in electron flow between the cells. In experiments using Fe(III) oxide coated surfaces and electrodes the inventors have demonstrated that *G. sulfurreducens* forms structured biofilms and generates energy for growth by transferring electrons across the biofilm cell layers, a process for which the expression of the nanowires is needed. Pilus nanowires permit electronic communication between the biofilm cells and maintain the electronic efficiency per cell constant as the biofilm grows. The pili have a structural role in the biofilms and help maintain adequate cell spacing to provide optimum electronic communication and electron flow across the biofilm.

The nanowires can be purified by any available method. In one embodiment, the method comprises lysis of cells expressing the nanowires, followed by selective removal of contaminating cell macromolecules, and then selective separation of pure nanowires from other proteins. See Examples 5-7. In one embodiment, a single step purification method is used which may have yields in excess of 50%, such as up to 55% or up to 60% or higher, including any and all ranges there between. In one embodiment, the yield is at least about 63%. Higher yields, in excess of 63% may also be possible, such as up to about 95%, including any and all ranges there between. The protocol is flexible, in the sense that it can be adapted for use with substantially any sample of pili-expressing cells, substantially any method to remove contaminating cell macromolecules that do not affect the integrity of the nanowires, and substantially any method to selectively separate the nanowires from other contaminating proteins based on the nanowires' unique attributes.

The resulting nanowires are essentially pure, as they are stripped of contaminants, metals, ions, metalloenzymes, flavins, quinones and other redox cofactors. In one embodiment, the purified nanowires are composed of a single peptide subunit (pilin or PilA) which polymerizes via hydrophobic interactions to form the pilus, i.e., nanowire filament. These nanowires can be stored dry substantially indefinitely and can be resuspended in appropriate solvents, as needed, for downstream applications. As noted above, surprisingly, these novel purified nanowires have rectifying behavior due, in part, to the absence of cellular contamination. Particular rectifying behavior is also due to the protein composition (i.e., amino acid make-up) and structure of the nanowire.

In one embodiment, the rectifiers described herein are capable of functioning as an asymmetric conductor for voltages of various ranges, such as, for example, voltages (V) having a range of about ±0.8 V or a range of about ±1.2 V. The rectifiers may also be useful at higher voltages. However, in some embodiments when higher voltages are generated, heat and/or damage to the rectifier and/or associated materials may occur, reducing the performance of the one or more nanowires contained therein.

In one embodiment, the purified microbial nanowires function as one-way conductors for voltages in the range of ±0.8 V (see the Examples).

The method provided by the invention for purifying nanowire polypeptide allows for the purification of nanowire polypeptides that properly fold to form the pilus structure described in the Examples.

Chemically Modified Nanowire Polypeptides

In some embodiments, the nanowire polypeptides are chemically modified. Such chemically modified nanowire polypeptides can be generated from nanowire polypeptides with a natural (non-recombinantly engineered) sequence that is chemically modified. Alternatively, the chemically modified nanowire polypeptides can be a mutant nanowire polypeptide that also contains substitutions, deletions or additions of amino acids that are not normally found in naturally occurring pilus nanowires. Thus, for example, before chemical modification, the nanowire polypeptides can have any of SEQ ID NO: 1-10, or a variant thereof. The nanowire polypeptides can therefore have a genetically modified sequence made by any of the procedures described herein.

In some embodiments, the nanowire polypeptides can be chemically modified to modulate their conductive, adhesive, coupling and/or other properties. Such chemical modification can be performed by procedures available in the art using a variety of reagents. For example, reagents such as performic acid, peroxides, iodoacetamide, iodoacetic acid, bissulfosuccinimidyl suberate, i-ethyl-3-(3-dimethylaminopropyl) carbodiimide, N-ethylmaleimide, methyl methanethiosulfonate and S-(2,2,5,5-tetramethyl-2,5-dihydro-1H-pyrrol-3-yl)methyl methanesulfonothioate (MTSL) can be used to modify the conductive, adhesive, coupling and/or other properties of the nanowire polypeptides. In other embodiments, the nanowire polypeptides can be glycosylated, acylated or conjugated to an alkylene glycol (e.g., polyethylene glycol or PEG). Such modifications can be performed by procedures available in the art. See, e.g., John M. Walker, THE PROTEIN PROTOCOLS HANDBOOK (2002)(especially Part IV); Means, G. E. and Feeney, R. E. CHEMICAL MODIFICATIONS OF PROTEINS. Holden-Day, San Francisco (1971).

Uses for the Nanowires

The nanowire polypeptides described herein have rectifying behavior due to the protein composition (i.e., amino acid make-up) and structure of the nanowire. Such rectifying behavior is a characteristic of the polypeptide in pure form, for example, in absence of metals and cellular contaminants. The genetically and/or chemically modified nanowire polypeptides also have rectifying behavior when in impure form, for example, when present in vivo, in compositions and/or in articles of manufacture.

The term "rectifier" as used herein, refers to one or more nanoscale solid-state electronic diodes that act as either a conductor or an insulator, depending on the sign of the voltage. A rectifier provides asymmetric axial electronic conductance, i.e., differential forward versus reverse conductivity. A single diode and rectifier essentially refer to the same type of component. By combining more than one diode together, various properties of the rectifier can be altered.

The nanowire polypeptides can self-assemble into nanowires that can include one or more nanowire polypeptide subunits with various molecular weights (MW). The nanowire polypeptide subunits can have a variety of molecular weights ranging from, for example, at least about 3-kDa, or higher, or between about 3-kDa and about 25-kDa or between about 3-kDa and 20-kDa or between about 3-kDa and about 10-kDa or between about 4-kDa and about 9-kDa, or between about 5.5-kDa and about 7.5-kDa, including any range there between. In one embodiment, the subunit molecular weight is about 6.5-kDa or at least about 6.5-kDa. In one embodiment, such nanowires do not contain contaminants such as metals, ions, metalloenzymes, and redox cofactors such as flavins and quinones.

Rectifying devices using microbial nanowires are desirable because they can be mass-produced and purified from recombinant hosts that are genetically engineered to produce the nanowire subunit. The nanowire polypeptide subunits can then be assembled in vitro or in vivo to form pili. This will enable the mass-production of microbial rectifiers at a low cost.

The rectifying behavior also opens, for example, the possibility to construct active devices such as transistors. With regard to nano-electronics, the rectifying behavior means that protein-based diodes (one-way conductors) can be constructed from these nanowires. In conventional microelectronics, diodes are the basic building blocks for transistors and more complex active components, including the microprocessors that run our computers. Hence, in analogy, the rectifying behavior of the nanowires opens the door to the construction of protein-based nano-electronics transistors and more complex devices.

The most basic applications in nano-electronics include, for example, radio demodulation (rectification of AM radio frequency signals to make audio signals), low voltage AC-DC power conversion, current steering, power switches and overvoltage protection. More advanced applications include, but are not limited to, the logic circuitry in electronic devices such as laptop computers, cellular phones and similar devices, further including computer chips, such as those used in the transportation industry, such as in aircraft and automobiles.

In one embodiment, the purified microbial nanowires function as one-way conductors for voltages in the range of ±0.8 V (see, e.g., Example 8).

In some embodiments, the nanowire polypeptides can be configured to include branches. Thus, the nanowire polypeptides can be assembled into a main pilus that is elongated and has a selected or desirable length. A plurality of branch pili may emanate from the main nanowire pilus at one or more substantially fixed distances along the length of the main pilus. The main pilus may also comprise one or more junctions with one or more secondary main pili, where the junctions are substantially perpendicular to the length of the main pilus.

In another embodiment, the nanowire polypeptides can be configured to form part of an apparatus. For example, the apparatus may contain at least one pilus comprising nanowires polypeptides. In other embodiments, the apparatus may contain at least one junction between pili. For example, the apparatus may include a plurality of junctions. Each junction may include a branch pilus and an elongate main pilus. For example, each junction may be situated at an interface between a branch pilus and the elongate main pilus.

As illustrated in the following non-limiting Examples, the inventors have also demonstrated, for the first time, that chemical modification (e.g., which may include chemical stripping) and/or genetic engineering, can be used to manipulate the protein composition, structure and binding properties of microbial nanowires to selectively modify rectification properties. Microbial rectifiers also can be manipulated via genetic engineering to bind specific ligands for sensor design, controlled and specific deposition during device manufacturing, etc.

Thus, the following non-limiting Examples further illustrate some aspects of the invention.

Example 1

Materials and Methods

This Example describes methods that can be used to make and analyze nanowire polypeptides.

Bacterial Growth Conditions.

*Geobacter sulfurreducens* strain PCA was used for the majority of the studies of nanowire structure and function. Cells were routinely grown at 30° C. in NB medium (Coppi et al, APPL. ENVIRON. MICROBIOL. 67: 3180-87 (2001)) supplemented with 15 mM acetate and 40 mM fumarate (NBAF) before being transferred three times in a modified fresh water (FW) medium (Lovley & Phillips, APPL. ENVIRON. MICROBIOL. 54: 1472-80 (1988)) supplemented with 15 mM acetate and 40 mM fumarate (FWAF). Briefly, a concentrated (10×) basal FW medium stock containing $NaHCO_3$ (25 g/L), $NaH_2PO_4.H_2O$ (0.6 g/L), $NH_4Cl$ (2.5 g/L), and KCl (1.0 g/L) was prepared. The electron donor and acceptor were prepared as sterile concentrated stocks (0.75 M sodium acetate and 1 M sodium fumarate, respectively) and the pH of the stock solutions was adjusted to 7 prior to autoclaving. Vitamins were prepared as separate solutions as previously described by Balch et al. (MICROBIOL. REV. 43: 260-96 (1979)). Trace minerals were prepared as previously described by Lovley et al. (APPL. ENVIRON. MICROBIOL. 48:81-87 (1984)), except that $ZnSO_4$ was replaced with $ZnCl_2$ (0.13 g/L), and $Na_2WO_4.2H_2O$ (0.025 g/L) was added. FWAF medium contained FW stock (96 ml/L), 0.75 M sodium acetate (20 ml/L), 1 M sodium fumarate (40 ml/L), vitamin solution (10 ml/L), mineral solution (10 ml/L) and $ddH_2O$ to a final volume of 1 L. The medium was dispensed in pressure tubes or serum bottles, sparged with $N_2:CO_2$ (80:20) to remove dissolved oxygen and sealed with butyl rubber stoppers and aluminum tear off seals (Wheaton) prior to autoclaving. For pili induction, exponentially-growing cells from FWAF cultures grown at 30° C. were subcultured in 100 ml of fresh FWAF with 30 mM acetate and 40 mM fumarate and incubated at 25° C. until they reached early stationary phase (ca. 72 h).

Isolation and Purification of Pili.

Pili were purified to homogeneity using a modification of a protocol previously used to purify enterobacterial fimbriae (see, Collinson et al. (J. BACTERIOL. 173: 4773-81 (1991)). Pili-expressing cells were harvested by centrifugation (13,000×g) for 15 min at 25° C. and resuspended in 6 ml of 10 mM Tris HCl, pH 8.0 (Tris buffer; Invitrogen, 99.9%). The cells were lysed by sonication (5 1-min at 4° C. per 1 ml of cell suspension; Branson Sonifier 450) before adding RNase A (bovine pancreas; Roche Diagnostics) and DNase I (bovine pancreas. Sigma, 91% purity) enzymes to a 0.1 mg/ml final concentration and $MgCl_2$ (J. T. Baker, 99.4%) to a final concentration of 1 mM. The cell extracts were incubated at 37° C. for 20 min to enzymatically degrade the nucleic acids in the sample. Lysozyme (hen egg white, Roche Diagnostics) was then added to a concentration of 1 mg/ml and incubated at 37° C. for 40 min with gentle shaking (200 rpm, Innova 4340, New Brunswick). Cell membranes and proteins in the extract were solubilized with sodium dodecyl sulfate (SDS, 1% final concentration; Sigma 98.5%) after incubation at 37° C. for 30 min. The SDS-insoluble fraction was collected by centrifugation (12,100×g, 15 min, 25° C.) and washed twice with 6 ml of Tris buffer. The SDS-insoluble fraction in Tris buffer was digested again with RNase, DNase and lysozyme, as described above. Mechanical vortexing (Fisher Scientific) was used to mix the samples. Samples with large clumps and/or aggregates were subjected to 2 additional cycles of sonication for 1 min at 4° C. The insoluble fraction was collected as described above, washed twice, and resuspended in 1 ml of Tris buffer. When needed, the sample was stored at −20° C. overnight. The protein sample was suspended in 2 ml of SDS-polyacrylamide gel electrophoresis (PAGE) sample buffer (10% [v/v]glycerol; 5% [v/v]b-mercaptocthanol; 2% [w/v] SDS, and 62.5 mM Tris HCl, pH 6.8) (Laemmli, Nature 227:680-85 (1970)) and boiled for 15 min. The SDS-treated sample was loaded on top of a preparative 12% polyacrylamide gel with a 5% stacking gel, and subjected to electrophoresis at 40 mA for 5 h using Prep Cell 491 (Bio-Rad). The material that did not enter the stacking gel was recovered by aspiration with a pipette and washed three times with 1 ml $ddH_2O$ of double distilled water by centrifugation (12,100×g, 15 min, 25° C.). The protein in the SDS-insoluble fraction was extracted twice with 95% ethanol (Decon Laboratories) and lyophilized or dried in a SpeedVac system (Savant Instruments Inc) at room temperature for approximately 20 min. This ethanol step also solubilized organic contaminants such as quinone-like compounds or organic cofactors. The dried protein was resuspended in 1 ml of $ddH_2O$ and vortexed for 60 seconds to break up the large clumps. Poorly-bound protein in the insoluble material was extracted with 0.2 M glycine (pH 1.5, adjusted with HCl; Invitrogen) at 100° C. for 10 min. The insoluble fraction was recovered by centrifugation (16,000×g, 25 min, 4° C.), washed five times with $ddH_2O$, and lyophilized or dried in a SpeedVac at room temperature until completely dry. The dried sample was then stored at −20° C. for short-term use or flash frozen in liquid nitrogen for long-term use.

Analytical Methods.

Quantitative elemental analysis of the purified pili preparations was performed by Inductively Coupled Plasma-Atomic Emission Spectrometry (ICP-AES) using a Thermo Jarrell-Ash Enviro 36 Inductively Coupled Argon Plasm (Chemical Analysis Laboratory, University of Georgia, Athens). For these experiments, 1 ml aqueous samples of purified pili containing 40-70 μg/ml of protein were analyzed in reference to blank control samples (without protein). When indicated, ethylenediaminetetraacetic acid (EDTA, Invitrogen) was added to the sample at a final concentration of 0.1 mM prior to the ICP-AES analyses. Protein concentration was determined using the bichinchoninic acid (BCA) assay (Pierce®, Thermo Scientific; see Smith et al., Anal. Biochem. 150: 76-85 (1985)), with Bovine Serum Albumin (BSA) as the protein standard.

Protein Electrophoresis.

Dried pili preparations were resuspended in 15 ml of $ddH_2O$ containing 2% (w/v) Octyl-β-D-Glucopyranoside (OG) (Sigma, 98%) and incubated at room temperature for 1 h prior to SDS-PAGE. SDS-PAGE was performed according to the method of Laemmli as modified by Ames (Laemmli, Nature 227:680-85 (1970); Ames, J. Biol. Chem. 249:634-44 (1974)). The OG-treated sample was boiled in SDS-PAGE sample buffer (Laemmli, Nature 227:680-85 (1970)) and subjected to electrophoresis on 12% ReadyGels (Bio-Rad) using a Mini Protean Tetra Cell apparatus (Bio-Rad). After electrophoresis, the gels were silver stained using the Pierces Silver Stain for Mass Spectrometry kit (Thermo Scientific), following the instructions supplied by manufacturer. After silver-staining, the ca. 6.5-kDa PilA protein band was excised from the gel, destained and digested with trypsin following the procedure described by manufacturer (Pierce® Silver Stain for Mass Spectrometry, Thermo Scientific). The peptides in the tryptic digest were concentrated and purified chromatographically with Cis reversed-phase media (ZipTip®, Millipore) and separated by matrix assisted laser desorption ionization-time of flight spectrometry (MALDI-TOF, Shimadzu Axima). Peptide identification and prediction of potential contributions of post-translational modifications to the peptide mass was performed using the MS-DIGEST tool at the ProteinProspector database from the University of California, San Francisco (see website at prospector.ucsf.edu/prospector/cgi-binimsform.cgi?form=msdigest).

Western Blot (Immunoblot) Analysis.

Proteins separated by SDS-PAGE were electrophoretically transferred to a nitrocellulose membrane (HyBond ECL™, Amersham GE Healthcare) at 50 V for 15 min using a Mini Protean Tetra Cell apparatus (Bio-Rad). The rapid western blotting kit (Amresco®) was used for the electrophoretic transfer and membrane blocking, following manufacturer's recommendations. After blocking, the membrane was incubated in 10 ml rapid antibody diluent solution, (45 min, room temperature, gentle agitation) with a 1:5000 dilution of the primary antibody (rabbit α-PilA polyclonal antibodies raised against the 42 amino acids at the carboxy-terminus of the PilA protein) and a 1:2500 dilution of goat α-rabbit IgG antibodies conjugated to the $Cy^{tm}$ 5 fluorescence dye (ECL™ Plex, Amersham GE Healthcare). The membrane was washed in rapid wash solution provided by manufacturer (3 times 5 min). The membrane was then scanned with Typhoon imager operated in fluorescence mode (excitation at 633 nm, 670 BP 30 filter, and PMT setting at 600 V) to visualize the protein bands that hybridized with the primary antibodies.

Microscopy.

For Confocal Laser Scanning Microscopy (CLSM), dried preparations of purified pili were dissolved in phosphate buffer saline (PBS), deposited on the surface of a glass cover slip and allowed to adsorb for 30 min. The adsorbed pili were then washed with PBS and fixed with 100 μl of 3.7% paraformaldehyde in PBS. After washing with PBS, the samples were incubated for 30 min in PBS containing 1% BSA, before adding the anti-PilA primary antibody (1:100) and incubating at 4° C. overnight. Following three washes in PBS-1% BSA, the samples were incubated with the secondary antibody (α-rabbit conjugated to Alexa fluor 488 dye, 1:1000) for 1 h. The cover slip was then washed 3 times with PBS buffer and examined with Zeiss LSM Pascal confocal microscope equipped with a Plan-Neofluar 63× oil objective (excitation, 488 nm; emission, 505-535 nm). For transmission electron microscopy (TEM), an aqueous solution of purified pili was adsorbed on a carbon-copper grid (Mesh 300, Electron Microscopy Sciences), negatively stained with 1% (w/v) uranyl acetate in distilled water. The negatively stained samples were examined with a Jeol 100 CX electron microscope (Japan Electron Optic Laboratory) operated at 100 kV.

Scanning Probe Microscopy.

Distal (lateral) and axial (length) conductivity measurements were performed, respectively, by scanning tunneling microscopy (STM) and conductive probe-atomic force microscopy (CP-AFM). STM imaging and spectroscopy was performed as described by Veazey et al. (*Filament-like graphite artifacts by STM*, ULTRAMICROSCOPY (2010)). For CP-AFM measurements a Bio-AFM-CF instrument (Asylum) was used and a gold electrode grid nanofabricated onto a silicon substrate was used for biological deposition. For the fabrication of the gold grid, photoresist (Shipley S1813) was spin-coated onto silicon wafers having a 300 nm thermal oxide layer ($SiO_2$). After photoresist development, patterned gold electrodes were deposited by thermally evaporating 5 nm of titanium followed by 25 nm of gold onto the surface of the wafer. A solution containing ca. 40-70 µg/ml of purified pili in $ddH_2O$ were then deposited onto the electrodes, left to adsorb for 25 minutes, and then wicked dry with absorbent paper. CP-AFM was performed with Pt-coated cantilevers having spring constant 2 N/m (Veeco). Pilus nanowires lying across the gold-$SiO_2$ interface were first identified in imaging mode. For current voltage (I-V) measurements, the tip was placed on a point of the pilus lying on the $SiO_2$. Positive controls were generated by positioning the tip on the gold electrode, while negative controls were produced by positioning the tip on the $SiO_2$ substrate at 100-nm distances from the gold edge.

Example 2

Conservation of Geobacteraceae pilA Amino Acid Sequences and Structures

The amino acid sequences encoded by the pilA gene of several Geobacteraceae were examined to identify conserved amino acids in the pilA nanowire gene product. Alignment of all the pilin-like sequences in the available Geobacteraceae genomic sequences demonstrated that three tyrosines are conserved in all the Geobacteraceae pilins, suggesting it is a key residue for the nanowire function (FIG. 1). Furthermore, conserved positively charged (arginine and lysine) amino acids are positioned in the vicinity of some of the tyrosines, a common arrangement that keeps the aromatic orbitals empty and available to receive an electron, thus promoting electron hopping (FIG. 2). On the other hand, conserved negatively-charged amino acids are also positioned in the vicinity of some of the tyrosines (FIG. 2A) and may serve as proton acceptors to facilitate the electron hopping.

*Geobacter* pilins belong to the subclass type IVa, which is broadly defined by their short (ca. 150 amino acids) length and conserved N-t amino acid sequence carrying the recognition site for a dedicated pre-pilin peptidase. In addition, all type IVa pilins carry an N-terminal N-methylated phenylalanine upon processing. The *Geobacter* pilins, though much shorter than other type IVa pilins (~60-70 amino acids), contain the conserved N-terminal sequence required for processing and assembly and the N-methylated phenylalanine of type IVa pilins. However, amino acid divergence at the C-terminus places them in an independent line of descent.

The secondary structure of the *Geobacter* pilin also is unique among all known type IVa pilins (FIG. 2B). It contains the hydrophobic N-terminal α-helix that promotes pilin polymerization, a short αβ-loop, and lacks the C-terminal globular head (with a disulfide bond) that confers on the pilus its specific functions. Particular structures, in particular α-helix conformations, have been shown to contribute to peptide conductivity. Furthermore, the pilin of *P. aeruginosa* strain K (PAK pilin), which serves as a structural model for type IVa pilins, has the C-terminal globular head and polymerizes in vivo to produce nonconductive pilus filaments.

Pilin assembly via hydrophobic interactions proceeds in a helical fashion and may help position electroactive amino acids and merge or bond their atomic orbitals optimally so as to favor charge transport along and across the nanowire.

Example 3

Genetic Manipulation of Redox-Active Amino Acids in Pilin Nanowires

This Example illustrates that manipulation of redox-active amino acids in the pilin nanowires enables the generation of nanowires with altered conductive properties.

Previous work has indicated that aromatic amino acids are redox-active amino acids that serve as electronic mediators of protein electron transfer. When properly positioned in close proximity to each other they function as redox-active aromatic intermediates and create an electron hopping pathway. Preliminary evidence indicates that electron hopping is favored by amino acids that can be easily oxidized such as tyrosines and tryptophans.

Since the rates of electron hopping are linearly dependent on the distance between relay amino acids, site-directed mutagenesis was used to genetically manipulate the distance between tyrosine residues in the pilus. As a proof of concept, tyrosine $Y_{57}$ was initially replaced with an alanine ($Y_{57}A$) and later with a phenylalanine ($Y_{57}F$). The tyrosine at position 57 ($Y_{57}$) was a good candidate because it is at the C-terminal end of the pilin and exposed to the pilus exterior, so its replacement did not radically affect the pilus structure. Alanine was initially used to replace the $Y_{57}$ residue because it clearly has no redox activity. Phenylalanine was later used to replace the $Y_{57}$ residue because it is structurally similar to tyrosine yet lacks its redox activity.

The mutated pilin genes were expressed in trans in a PilA⁻ mutant background using the expression vector pRG5 (Coppi et al., *Appl. Environ. Microbiol.* 67: 3180-87 (2001)); Leang et al., *BMC Genomics* 10, 331 (2009). This complementation produced strains that expressed pili with the $Y_{57}F$ substitution.

Using the same approach, the negatively charged amino acids in the tyrosines' vicinities ($D_{53}$, $D_{54}$, and $E_{60}$) were replaced with a non-charged amino acid, alanine (A), which does not affect the structure of the pilin. Single, double and triple mutations were made. Thus, mutant nanowires with the single $E_{60}A$ replacement, double $D_{53}A$ $D_{54}A$ replacement, and triple $E_{60}A$ $D_{53}A$ $D_{54}A$ replacement were generated. A mutant strain of *G. sulfurreducens* that fails to produce pili nanowires (PilA⁻) was used as a negative control.

More specifically, mutagenesis was performed using the Stratagene QuikChange mutagenesis kit. This mutagenesis tool uses pfu Turbo as a polymerase to replicate template DNA from complementary primers containing mutagenic nucleotides. The mutagenic oligonucleotides used for site-directed mutagenesis are shown below in Table 3.

TABLE 3

Oligonucleotides for Mutagenesis

| Name SEQ ID | Oligonucleotide sequence | Nucleotide replacement position(s) |
|---|---|---|
| $Y_{57}F$ NO: 12 | 5' C GCA TTT GCT GAT GAT CAA ACC TTT CCG CCC GAA AG 3' | 200 |
| $Y_{32}F$ NO: 13 | 5' CGT GTC AAG GCG TTC AAC AGC GCG GCG 3' | 115 |
| $Y_{27}F$ NO: 14 | 5' CCG CAG TTC TCG GCG TTT CGT GTC AAG GC 3' | 100 |
| $E_{60}A$ NO: 15 | 5' GAT GAT CAA ACC TAT CCG CCC GCA AGT TAA 3' | 209 |
| $D_{53,54}A$ NO: 16 | 5' GAG TCC GCA TTT GCT GCT GCT CAA ACC TAT CCG CCC 3' | 188, 191 |
| $D_{53,54}A$ $E_{60}A$ NO: 17 | 5' GAG TCC GCA TTT GCT GCT GCT CAA ACC TAT CCG CCC GCA AGT TAA 3' | 188, 191, 209 |
| $S_{61}A$ NO: 18 | 5' GAT GAT CAA ACC TAT CCG CCC GAA GCT TAA 3' | 211, 212 |

The name of the mutated nanowire is provided in the first (left) column, where the nanowire name is the original amino acid one-letter symbol followed by the position of the amino acid (as a subscript), which is then followed by the one-letter symbol for the replacement amino acid. The middle column shows the oligonucleotide sequence with the mutagenized codon (in bold) and mutated nucleotide(s) (underlined). The positions of the replaced nucleotides in the pilA nucleotide sequence are shown in the last (right).

The amino acid sequences of the nanowire polypeptides encoded by these nucleic acids are as follows.

The $Y_{57}F$ polypeptide is shown below as SEQ ID NO: 19.

```
 1    FTLIELLIVV AIIGILAAIA IPQFSAYRVK AYNSAASSDL
41    RNLKTALESA FADDQTFPPE S
```

The $Y_{32}F$ polypeptide is shown below as SEQ ID NO:20.

```
 1    FTLIELLIVV AIIGILAAIA IPQFSAYRVK AFNSAASSDL
41    RNLKTALESA FADDQTYPPE S
```

The $Y_{27}F$ polypeptide is shown below as SEQ ID NO:21.

```
 1    FTLIELLIVV AIIGILAAIA IPQFSAFRVK AYNSAASSDL
41    RNLKTALESA FADDQTYPPE S
```

The $E_{60}A$ polypeptide is shown below as SEQ ID NO:22.

```
 1    FTLIELLIVV AIIGILAAIA IPQFSAYRVK AYNSAASSDL
41    RNLKTALESA FADDQTYPPA S
```

The $D_{53,54}A$ polypeptide is shown below as SEQ ID NO:23.

```
 1    FTLIELLIVV AIIGILAAIA IPQFSAYRVK AYNSAASSDL
41    RNLKTALESA FAAAQTYPPE S
```

The $D_{53,54}A$, $E_{60}A$ polypeptide is shown below as SEQ ID NO:24.

```
 1    FTLIELLIVV AIIGILAAIA IPQFSAYRVK AYNSAASSDL
41    RNLKTALESA FAAAQTYPPA S
```

The $S_{61}A$ polypeptide is shown below as SEQ ID NO:25.

```
 1    FTLIELLIVV AIIGILAAIA IPQFSAYRVK AYNSAASSDL
41    RNLKTALESA FADDQTYPPE A
```

The constructs were transfected into *Geobacter sulfurreducens* strain PCA. Cells were routinely grown at 30° C. in NB medium (Coppi et al., APPL. ENVIRON. MICROBIOL. 67: 3180-87 (2001)) supplemented with 15 mM acetate and 40 mM fumarate (NBAF) before been transferred three times in a modified fresh water (FW) medium (Lovley & Philips, APPL. ENVIRON. MICROBIOL. 54: 1472-80 (1988)), supplemented with 15 mM acetate and 40 mM fumarate (FWAF). Briefly, a concentrated (10×) basal FW medium stock containing $NaHCO_3$ (25 g/L), $NaH_2PO_4 \cdot H_2O$ (0.6 g/L), $NH_4Cl$ (2.5 g/L), and KCl (1.0 g/L) was prepared. The electron donor and acceptor were prepared as sterile concentrated stocks (0.75 M sodium acetate and 1 M sodium fumarate, respectively) and the pH of the stock solutions was adjusted to 7 prior to autoclaving. Vitamins were prepared as separate solutions as described by Balch et al. (MICROBIOL. REV. 43: 260-96 (1979)). Trace minerals were prepared as described by Lovley et al. (APPL. ENVIRON. MICROBIOL. 48: 81-87 (1984)), except that $ZnSO_4$ was replaced with $ZnCl_2$ (0.13 g/L), and $Na_2WO_4 \cdot 2H_2O$ (0.025 g/L) was added. FWAF medium contained FW stock (96 ml/L), 0.75 M sodium acetate (20 ml/L), 1 M sodium fumarate (40 ml/L), vitamin solution (10 ml/L), mineral solution (10 ml/L) and ddH2O to a final volume of 1 L. The medium was dispensed in pressure tubes or serum bottles, sparged with $N_2:CO_2$ (80:20) to remove dissolved oxygen and sealed with butyl rubber stoppers and aluminum tear off seals (Wheaton) prior to autoclaving. For pili induction, exponentially-growing cells from FWAF cultures grown at 30° C. were subcultured in 100 ml of fresh FWAF with 30 mM acetate and 40 mM fumarate and the cells were incubated at 25° C. until they reached early stationary phase (ca. 72 h).

The conductive properties of the mutant nanowires were measured by testing the mutant cells compared to wild type and PilA⁻ cells in microbial fuel cell assays. Two measurements were made: (i) coulombic efficiency, which measures the amount of electron donor converted into current by the cells, and (ii) the coulombic rates, which measure the coulombic efficiency per day and are proportional to the electron transfer rates along the nanowires of the biofilms formed on the anode electrode.

Figure 3A:
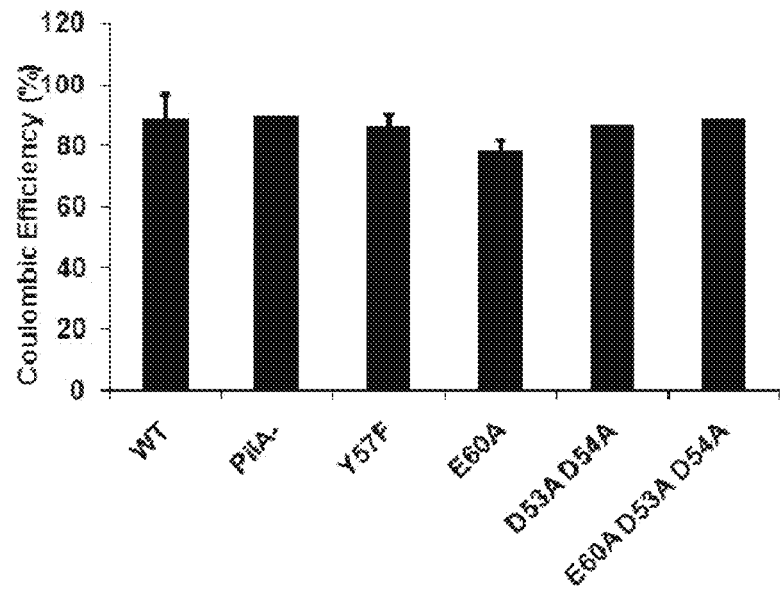
FIGS. 3A-3B show that nanowire conductivity can be manipulated via genetic engineering of the *Geobacter* pilin subunit. Pilin subunits were engineered by using a nanowire polypeptide having an $Y_{57}F$ replacement as starting material (SEQ ID NO: 19). The replacement of tyrosine at position 57 with phenylalanine removed one of the tyrosines used for electron hopping along the nanowires. Single mutant ($E_{60}A$), double mutant ($D_{53}A$, $D_{54}A$) and triple mutant ($E_{60}A$, $D_{53}A$, $D_{54}A$) polypeptides were made where negatively charged amino acids were replaced with alanine residues at position 60, position 53 and/or position 54, as described in the Examples. The negatively charged amino acids act normally as proton acceptors of the tyrosines during electron transfer.
Figure 3B:
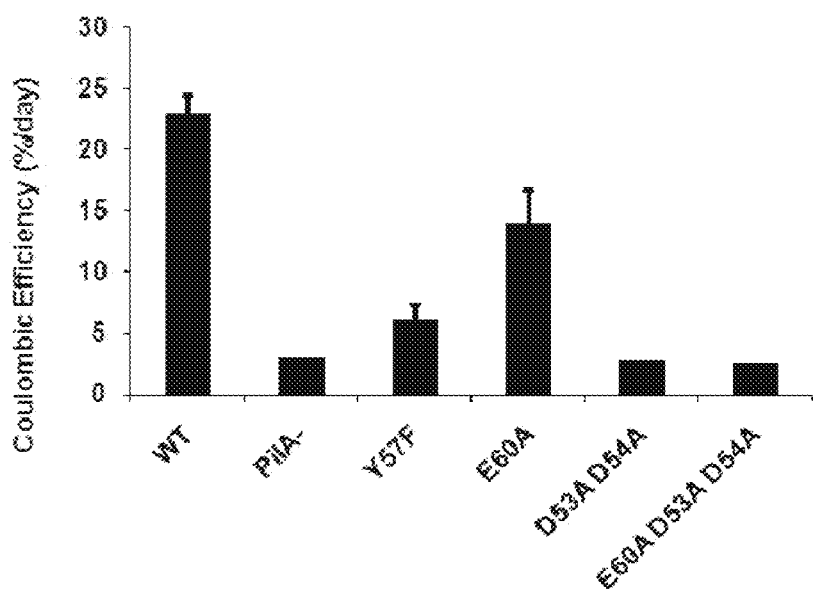

Because the nanowires are the electrical connections of the cells in the anode biofilm, defects in their conductivity translated into defects in the measured coulombic rates. As shown in FIG. 3A, the coulombic efficiency was the same in all the strains, meaning that all the cells converted the same amount of electron donor, acetate, into electricity thus ruling out any metabolic defects of the mutations. However, the amino acid replacements resulted in defects in the coulombic rates (FIG. 3B). The $Y_{57}F$ substitution produced nanowires with rates of electron transfer close to a mutant that did not produce the nanowires (PilA⁻), suggesting that the interruption of the electron pathway along the nanowire through the removal of one of the "stepping stones" (a tyrosine) produced nanowires with increased resistance to the passage of electrons. The replacement of a single negatively-charged amino acid ($E_{60}A$), which serves as a proton acceptor during electron hopping via tyrosines, resulted in a 1.7-fold decrease in the electron transfer rates. Double ($D_{53}A\ D_{54}A$) and triple ($E_{60}A\ D_{53}A\ D_{54}A$) mutants produced pili but had coulombic rates comparable to a pilus-deficient mutant.

Figure 4:
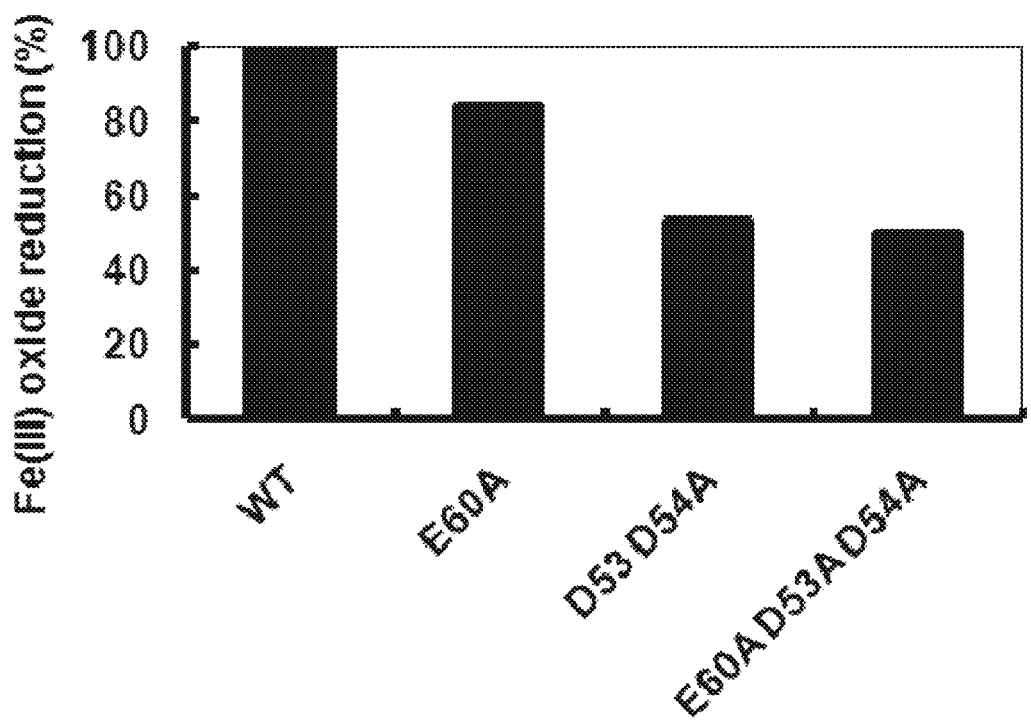
FIG. 4 illustrates electron transfer to Fe(III) oxides by cells expressing native (WT) nanowires or nanowires composed of pilins carrying single (E60A), double (D53A D54A) and triple (E60A D53A D54A) replacements of negatively charged amino acids. The negatively charged amino acids act as proton acceptors of the tyrosines during electron transfer. Their replacement with alanine resulted in nanowires with reduced ability to reduce Fe(III) oxides.

Another measure of the nanowire conductivity is its ability to reduce insoluble Fe(III) oxides into soluble Fe(II), which can be measured to indirectly determine the rates of Fe(III) oxide reduction. As shown in FIG. 4, the replacement of negatively charged amino acids also gave rise to a defect in the reduction of Fe(III) oxides.

These results demonstrate that amino acids in the pilin nanowire subunit can be selectively replaced to modulate the conductive properties of the nanowires pili.

Example 4

Genetic Manipulation of Attachment Points in Pilin Nanowire

This Example illustrates that manipulation of non-redox-active amino acids can modulate other functions of the nanowires.

For example, some amino acids in the pilin subunit are naturally post-translationally phosphorylated or modified with glycans. Pilin glycosylation is thought to modulate the binding of pili to various surfaces and other cells. Thus, the nanowire's post-translational modifications may participate in binding and optimal positioning of the electron acceptor for electronic coupling.

As illustrated below, genetic engineering of these post-translationally modified amino acids can be used to manipulate the adhesive properties of the nanowires for controlled deposition and efficient electronic coupling in integrated nanocircuits and other nanodevices. The post-translational modifications also affect the nanowire's charge and, therefore, could contribute to its conductive properties. Phosphorylation can affect the pilus charge, which could affect charge transport and the binding properties of the nanowires. Glycans encapsulating metallic nanowires reduce atomic contacts with the aqueous environment and minimize electronic fluctuations (see, Leroux et al., J. Am. Chem. Soc. 130: 13465-70 (2008)).

Post-translational modification of the nanowire subunit can be manipulated via genetic engineering to modulate the efficiency of the nanowire's conductive properties. A serine residue in C-terminal position 61 ($S_{61}$) may be glycosylated. Site-directed mutagenesis was used to replace this C-terminal serine ($S_{61}$) with an alanine, and generate cells that express a mutant nanowire $S_{61}A$.

Figure 5A:
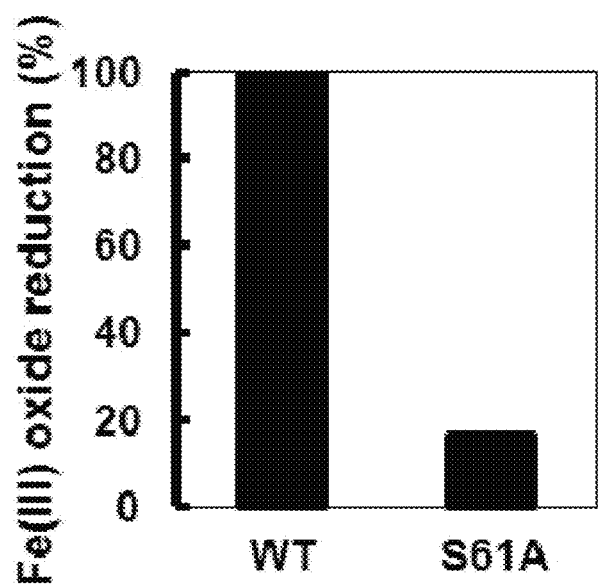
FIG. 5A-C illustrate that the adhesive properties of nanowires can be manipulated via genetic engineering. Nanowires were engineered with a S61A replacement to remove the glycosylation of serine at position 61. The replacement resulted in nanowires with reduced binding but same conductivity, as indicated by the defect in Fe(III) oxide reduction (FIG. 5A), the maintenance of the coulombic efficiency (FIG. 5B) and the electron transfer rates to electrodes (FIG. 5C) in microbial fuel cells.
Figure 5B:
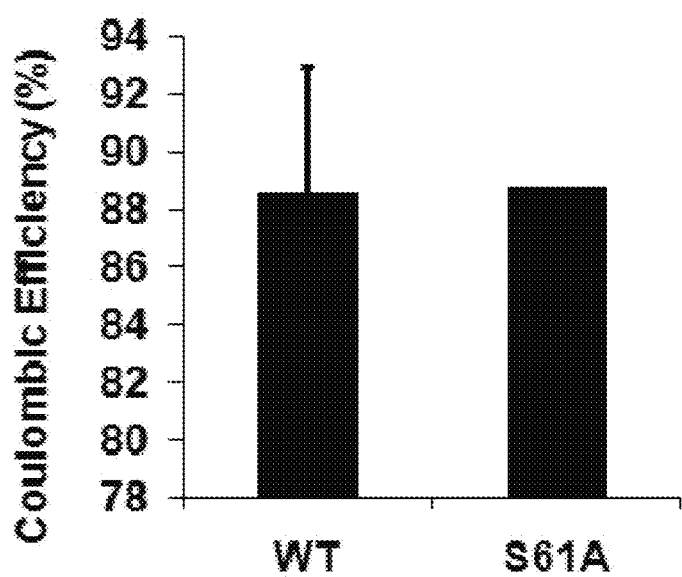
Figure 5C:
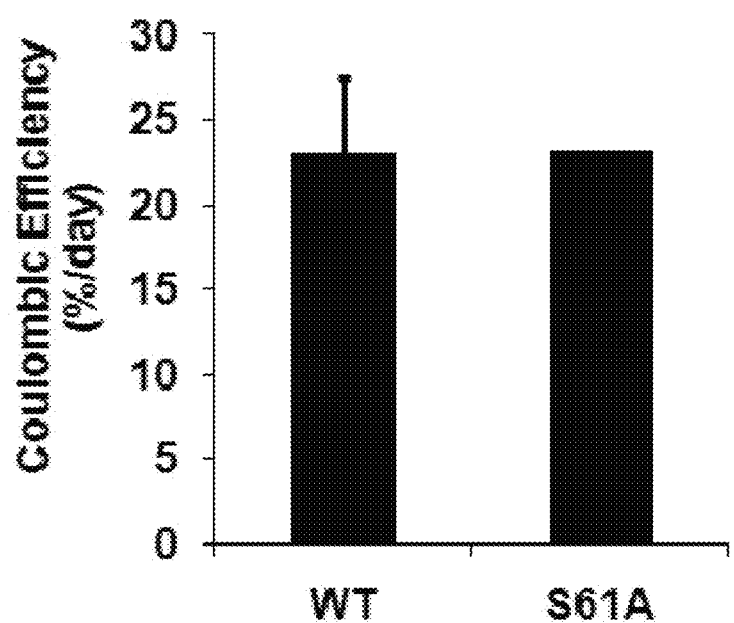

As shown in FIG. 5A, the $S_{61}A$ nanowires had a defect in Fe(III) oxide reduction that may be caused by defective binding and/or defective conductivity of the nanowires. Thus, the conductive properties of the $S_{61}A$ nanowires were tested in microbial fuel cell assays. In this case, the coulombic efficiencies and coulombic rates were the same in the wild-type and $S_{61}A$ nanowires, demonstrating that the conductive properties of the nanowires were unaltered.

Thus, the defect in Fe(III) oxide reduction but the existence of wild-type coulombic rates in the $S_{61}A$ nanowires indicates that the replacement of serine at position 61 affected the adhesive properties of the nanowires. Thus, genetic engineering can be used to manipulate properties of the nanowires other than conductivity to suit specific applications such as the controlled deposition of the nanowires on various surfaces.

Example 5

Method I for Purifying Pili to Homogeneity

In experiments performed by the inventors it was observed that the pili of G. sulfurreducens did not depolymerize using mild denaturation methods, including standard conditions with sodium dodecyl sulfate (SDS) detergent and heat treatment routinely used for denaturing SDS-electrophoresis (Laemmli, Nature 227, 680-685 (1970)). The observed biochemical resistance was due to the intrinsic resistance of the nanowire filaments to depolymerize in the presence of detergents, as well as their tendency to aggregate and form thick bundles. These thick bundles were also observed to be more resistant to depolymerization and denaturation than the individual pilus. This property suggests that the pili of G. sulfurreducens are very stable protein assemblies. As a result, selective separation of pili from other proteins, via preparative denaturing SDS electrophoresis, was chosen as a purification procedure (see, e.g., Collinson et al., J. Bacteriol. 173, 4773-4781 (1991)).

Geobacter Source

The bacterium Geobacter sulfurreducens strain PCA (Gsu) was obtained from the American Type Culture Collection (ATCC) where it is registered under accession number ATCC® 51573™. It was obtained as a substantially pure culture and maintained under conditions typically used in the art within the inventors' laboratory culture collection. All chemicals, including vitamins, were from Sigma-Aldrich and had a minimum purity of 98%.

Bacterial Growth Conditions

The Gsu PCA strain was used throughout the study. Cells were routinely grown at 30° C. in NB medium supplemented with 15 mM acetate and 40 mM fumarate (NBAF) before being transferred three times to a modified fresh water (FW) medium supplemented with 15 mM acetate and 40 mM fumarate (FWAF) (see, e.g., Coppi et al. Appl. Environ. Microbiol. 67, 3180-3187 (2001); Lovley & Phillips, Appl. Environ. Microbiol. 54, 1472-1480 (1988)). A concentrated (10×) basal FW medium stock containing $NaHCO_3$ (25 g/L), $NaH_2PO_4 \cdot H_2O$ (0.6 g/L), $NH_4C$ (2.5 g/L), and KCl (1 g/L) was prepared. The electron donor and acceptor were prepared as sterile concentrated stocks (0.75 M sodium acetate and 1 M sodium fumarate, respectively) and the pH of the stock solutions was adjusted to 7 prior to autoclaving.

Vitamins were prepared as separate solutions as previously described by Balch et al. (Microbiol. Rev. 43, 260-296 (1979)). Trace minerals were prepared as described by Lovley et al. (Appl. Environ. Microbiol. 48, 81-87 (1984)), except that $ZnSO_4$ was replaced with $ZnCl_2$ (0.13 g/L), and $Na_2WO_4 \cdot 2H_2O$ (0.025 g/L) was added. FWAF medium contained FW stock (96 mL/L), 0.75 M sodium acetate (20 ml/L), 1 M sodium fumarate (40 ml/L), vitamin solution (10 mL/L), mineral solution (10 ml/L) and $ddH_2O$ to a final volume of 1 L. The medium was dispensed in pressure tubes or serum bottles, sparged with $N_2:CO_2$ (80:20) to remove dissolved oxygen and sealed with butyl rubber stoppers and aluminum tear off seals (Wheaton) prior to autoclaving. For pili induction, exponentially-growing cells from FWAF cultures grown at 30° C. were subcultured in 100 ml of fresh FWAF with 30 mM acetate and 40 mM fumarate and incubated at 25° C. (Reguera et al. Nature 435, 1098-1101 (2005)) until they reached early stationary phase (ca. 72 h).

Pili Isolation and Purification

Pili were purified to homogeneity using a modification of the protocol by Collinson et al. (*J. Bacteriol.* 173, 4773-4781 (1991)). Pili-expressing cells were harvested by centrifugation (13,000×g) for 15 min at 25° C. and resuspended in 6 ml of 10 mM Tris HCl, pH 8.0 (Tris buffer; Invitrogen, 99.9%). The cells were lysed by sonication (five×1-min at 4° C. per 1 ml of cell suspension; Branson Sonifier 450) before adding RNase A (bovine pancreas; Roche Diagnostics) and DNase I (bovine pancreas, Sigma, 91% purity) enzymes to a 0.1 mg/ml final concentration and $MgCl_2$ (J. T. Baker, 99.4%) to a final concentration of 1 mM. The cell extracts were incubated at 37° C. for 20 min to enzymatically degrade the nucleic acids in the sample. Lysozyme (hen egg white, Roche Diagnostics) was then added to a concentration of 1 mg/ml and incubated at 37° C. for 40 min with gentle shaking (200 rpm, Innova 4340, New Brunswick). Cell membranes and proteins in the extract were solubilized with sodium dodecyl sulfate (SDS, 1% final concentration; Sigma 98.5%) after incubation at 37° C. for 30 min. The SDS-insoluble fraction was collected by centrifugation (12,100×g, 15 min, 25° C.) and washed twice with 6 ml of Tris buffer. The SDS-insoluble fraction in Tris buffer was digested again with RNase, DNase and lysozyme, as described above. Mechanical vortexing (Fisher Scientific) was used to mix the samples. Samples with large clumps and/or aggregates were subjected to 2 additional cycles of sonication for 1 min at 4° C. The insoluble fraction was collected as described above, washed twice, and resuspended in 1 ml of Tris buffer. When needed, the sample was stored at −20° C. overnight.

The protein sample was suspended in 2 ml of SDS-polyacrylamide gel electrophoresis (PAGE) sample buffer (10% [v/v]glycerol; 5% [v/v]b-mercaptoethanol; 2% [w/v] SDS, and 62.5 mM Tris HCl, pH 6.8) and boiled for 15 min. The SDS-treated sample was loaded on top of a preparative 12% polyacrylamide gel with a 5% stacking gel, and subjected to electrophoresis at 40 mA for 5 h using Prep Cell 491 (Bio-Rad). The material that did not enter the stacking gel was recovered by aspiration with a pipette and washed three times with 1 ml $ddH_2O$ of double distilled water by centrifugation (12,100×g, 15 min, 25° C.). The protein in the SDS-insoluble fraction was extracted twice with 95% ethanol (Decon Laboratories) and lyophilized or dried in a Speed Vac system (Savant Instruments Inc) at room temperature for approximately 20 min. This ethanol step also solubilized organic contaminants such as quinone-like compounds or organic cofactors. The dried protein was resuspended in 1 ml of $ddH_2O$ and vortexed for 60 seconds to break up the large clumps. Poorly-bound protein in the insoluble material was extracted with 0.2 M glycine (pH 1.5, adjusted with HCl; Invitrogen) at 100° C. for 10 min. The insoluble fraction was recovered by centrifugation (16,000×g, 25 min, 4° C.), washed five times with $ddH_2O$, and lyophilized or dried in a SpeedVac at room temperature until completely dry. The dried sample was then stored at −20° C. for short-term use or flash frozen in liquid nitrogen for long-term use.

Quantitative elemental analysis of the purified pili preparations was performed by Inductively Coupled Plasma-Atomic Emission Spectrometry (ICP-AES) using a Thermo Jarrell-Ash Enviro 36 Inductively Coupled Argon Plasm (Chemical Analysis Laboratory, University of Georgia, Athens). For these experiments, 1 ml aqueous samples of purified pili containing 40-70 micrograms of protein per milliliter were analyzed in reference to blank control samples (without protein). When indicated, ethylenediaminetetraacetic acid (EDTA, Invitrogen) was added to the sample at a final concentration of 0.1 mM prior to the ICP-AES analyses. Protein concentration was determined using the bichinchoninic acid (BCA) assay (Smith et al., (*Anal. Biochem.* 150, 76-85 (1985); Pierce®, Thermo Scientific) with Bovine Serum Albumin (BSA) as the protein standard.

Protein Electrophoresis

Dried pili preparations were resuspended in 15 ml of $ddH_2O$ containing 2% (w/v) Octyl-β-D-Glucopyranoside (OG) (Sigma, 98%) and incubated at room temperature for 1 h prior to SDS-PAGE. SDS-PAGE was performed according to the method of Laemmli (*Nature* 227, 680-685 (1970)) as modified by Ames (*J. Biol. Chem.* 249, 634-644 (1974)). The OG-treated sample was boiled in SDS-PAGE sample buffer (Laemmli, *Nature* 227, 680-685 (1970)) and subjected to electrophoresis on 12% ReadyGels (Bio-Rad) using a Mini Protean Tetra Cell apparatus (Bio-Rad). After electrophoresis, the gels were silver stained using the Pierce® Silver Stain for Mass Spectrometry kit (Thermo Scientific), following the instructions supplied by manufacturer.

After silver-staining, the ca. 7-kDa PilA protein band was excised from the gel, destained and digested with trypsin following the procedure described by manufacturer (Pierce® Silver Stain for Mass Spectrometry, Thermo Scientific). The peptides in the tryptic digest were concentrated and purified chromatographically with $C_{18}$ reversed-phase media (Zip-Tip®, Millipore) and separated by matrix assisted laser desorption ionization-time of flight spectrometry (MALDI-TOF, Shimadzu Axima). Peptide identification and prediction of potential contributions of post-translational modifications to the peptide mass was performed using the MS-DIGEST tool at the ProteinProspector database from the University of California, San Francisco, see website at prospector.ucsf.edu/prospector/cgi-bin/msform.cgi?form=msdigest.

Western Blot (Immunoblot) Analysis

Proteins separated by SDS-PAGE were electrophoretically transferred to a nitrocellulose membrane (HyBond ECL™, Amersham GE Healthcare) at 50 V for 15 min using a Mini Protean Tetra Cell apparatus (Bio-Rad). The rapid western blotting kit (Amresco®) was used for the electrophoretic transfer and membrane blocking, following manufacturer's recommendations. After blocking, the membrane was incubated in 10 ml rapid antibody diluent solution (45 min, room temperature, gentle agitation) with a 1:5,000 dilution of the primary antibody (rabbit α-PilA polyclonal antibodies raised against the 42 amino acids at the carboxy-terminus of the PilA protein) and a 1:2,500 dilution of goat α-PilA rabbit IgG antibodies conjugated to the $Cy^{tm}$ 5 fluorescence dye (ECL™ Plex, Amersham GE Healthcare). The membrane was washed in rapid wash solution provided by manufacturer (3 times, for 5 min). The membrane was then scanned with Typhoon imager operated in fluorescence mode (excitation at 633 nm, 670 BP 30 filter, and PMT setting at 600 V) to visualize the protein bands that hybridized with the primary antibodies.

Microscopy

For Confocal Laser Scanning Microscopy (CLSM), dried preparations of purified pili were dissolved in phosphate buffer saline (PBS), deposited on the surface of a glass cover slip and allowed to adsorb for 30 min. The adsorbed pili were then washed with PBS and fixed with 100 microliters of 3.7% paraformaldehyde in PBS. After washing with PBS, the samples were incubated for 30 min in PBS containing 1% BSA, before adding the anti-PilA primary antibody (1:100) and incubating at 4° C. overnight. Following three washes in PBS-1% BSA, the samples were incubated with the secondary antibody (α-PilA rabbit conjugated to Alexa fluor 488 dye, 1:1000) for 1 h. The cover slip was then washed three times with PBS buffer and examined with Zeiss LSM Pascal confocal microscope equipped with a Plan-Neofluar 63× oil objective (excitation, 488 nm; emission, 505-535 nm).

For transmission electron microscopy (TEM), an aqueous solution of purified pili was adsorbed on a carbon-copper grid (Mesh 300. Electron Microscopy Sciences), negatively stained with 1% (w/v) uranyl acetate in distilled water. The negatively stained samples were examined with a Jeol 100 CX electron microscope (Japan Electron Optic Laboratory) operated at 100 kV.

Distal (lateral) and axial (length) conductivity measurements were performed, respectively, by scanning tunneling microscopy (STM) and conductive probe-atomic force microscopy (CP-AFM). STM imaging and spectroscopy was performed as described by Veazey et al. (Electronic structure of Geobacter sulfurreducens pilus nanowires probed by Scanning Tunneling Microscopy. Phys. Rev. B (to be published in 2011)). For CP-AFM measurements a Bio-AFM-CF instrument (Asylum) was used. A gold electrode grid nanofabricated onto a silicon substrate was used for biological deposition. For the fabrication of the gold grid, photoresist (Shipley S1813) was spin-coated onto silicon wafers having a 300 nm thermal oxide layer ($SiO_2$). After photoresist development, patterned gold electrodes were deposited by thermally evaporating 5 nm of titanium followed by 25 nm of gold onto the surface of the wafer. A solution containing ca. 40-70 micrograms of purified pili protein per milliliter in dd$H_2$O were then deposited onto the electrodes, left to adsorb for 25 minutes, and then wicked dry with absorbent paper. CP-AFM was performed with Pt-coated cantilevers having spring constant 2 N/m (Veeco). Pilus nanowires lying across the gold-$SiO_2$ interface were first identified in imaging mode. For Current (I) versus voltage (V) ("I-V") measurements, the tip was placed on a point of the pilus lying on the $SiO_2$. Positive controls were generated by positioning the tip on the gold electrode, while negative controls were produced by positioning the tip on the $SiO_2$ substrate at 100-nm distances from the gold edge.

Results

Transmission electron microscopy (TEM) of negatively-stained SDS-insoluble samples confirmed the presence of bundles of fibrils morphologically similar to the pili displayed on the surface of cells of G. sulfurreducens. Furthermore, the fibrils were free of obvious cellular debris. The presence of the PilA subunit in the purified fibrils was detected immunologically by confocal laser scanning microscopy (CLSM) of purified fibrils hybridized to polyclonal antibodies raised against a recombinant truncated form of the PilA pilin subunit (anti-PilA) and fluorescently-labeled secondary antibodies. Atomic Force Microscopy (AFM) was used to image the purified pili from G. sulfurreducens that were deposited on a HOPG substrate. The resulting AFM image of the pilus fiber shows that the average width of the fibrils was in the 4-5 nm range.

Denaturing SDS-PAGE and immunodetection by Western blot using polyclonal anti-PilA antibodies was used to investigate the protein composition of the pili and asses its purity. Standard denaturation conditions with SDS detergent and heat treatment did not fully depolymerize the pili into the pilin subunit. However, treatment with octyl-glucoside partially depolymerized the pili into oligomers of various sizes and a protein band that migrated as between 3 and 10 kDa in the gel, consistent with the predicted size of the mature PilA protein (6.5 kDa without any post-translational modifications). After electrophoresis, a denaturing 4-20% SDS-polyacrylamide gel showed pili oligomers in untreated controls and pilus oligomers of various sizes as well as the ca. 7 kDa PilA band in samples pretreated with 1% or 2% octyl-glucoside. The 7 kDa band was positively detected as PilA in immunoblots using anti-PilA antibodies.

The 7-kDa protein band that was electrophoretically separated after depolymerizing purified pili with 2% octyl-glucoside was extracted from the gel, digested with trypsin and the mass of the tryptic peptides was analyzed by MALDI-TOF. Peptide mass fingerprinting of the tryptic digest by MALDI-TOF identified several PilA peptides, some carrying potential post-translational modifications, such as the N-methylation of the phenylalanine at the peptides amino-terminus that all pilins have. Details of peak assignment are presented in Table 4. These data confirmed the identity of the PilA band and demonstrate that the pili of G. sulfurreducens were selectively purified to homogeneity.

TABLE 4

Masses of Tryptic Peptides of PilA from Geobacter sulfurreducens Detected with MALDI-TOF Mass Spectrometry

| Peak | Expected mass | Observed mass | Sequence[a] | SEQ ID NO: | Modification |
|---|---|---|---|---|---|
| 1 | 2205 | 2207 | (K)TALESAFAD DQTYPPES | 26 | 2 phospho, acetyl |
| 2 | 2220 | 2221.6 | (K)TALESAFAD DQTYPPES | 27 | 2 phospho |
| 3 | 2280 | 2280.4 | (R)NLKTALESA FADDQTYPPES | 28 | methyl |
| 4 | 2295 | 2294.9 | (R)NLKTALESA FADDQTYPPES | 29 | 2 methyl |
| 5 | 2309 | 2308.5 | (R)NLKTALESA FADDQTYPPES | 30 | acetyl |
| 6 | 3326 | 3323.9 | FTLIELLIVVAII GILAAIAIPQFSA YRVKA(V) | 31 | — |
| 7 | 3341 | 3337.6 | FTLIELLIVVAII GILAAIAIPQFSA YRVKA(V) | 32 | methyl |
| 8 | 3356 | 3353.6 | FTLIELLIVVAII GILAAIAIPQFSA YRVKA(V) | 33 | 2 methyl |

[a]An amino acid in parenthesis is a trypsin cleavage position.

The lack of proteins, other than PilA, in the pili fractions excluded the possibility of c-cytochromes being associated with the pili. However, it did not exclude the possibility of metals being directly bound to the pilus shaft. Amino acid residues can be positioned in the folded protein to form structural motifs for metal coordination. Bound metals not only enable electron transfer reactions but also stabilize the protein's secondary structure (Reguera et al. Nature 435, 1098-1101 (2005); Haas & Franz, Chem. Rev. 109, 4921-4960 (2009)).

The SeqCHED server (Levy et al. Proteins 76, 365-374 (2009)) was used within the SPACE tools suite (Sobolev et al. Nucleic Acids Res. 33, W39-43 (2005)) to identify soft (Zn, Fe, Ni, Cu, Co, Mn) and promiscuous, hard (Mg, Ca) metalion binding sites in the mature PilA amino acid sequence. However, none were identified.

Despite the lack of conserved metal-binding sites in the pilin, the assembly of pilin subunits to form the pilus shaft could create structural and sequence motifs for metal coordination. To investigate this, Inductively Coupled Plasma- Atomic Emission Spectroscopy (ICP-AES) was used for elemental analysis of aqueous samples of the purified pili in reference to protein-free 'blank' controls. This technique has been traditionally used for metal analyses of metalloproteins because of its high specificity and sensitivity at the identification and quantification of trace elements based on the distinct energy that excited electrons emit at a given wavelength as they return to ground state (Ma et al. *Electrophoresis* 25, 2469-2477 (2004)). No significant differences were observed between samples and protein-free controls for most of the elements analyzed. These results are shown in Table 5 below.

TABLE 5

Elemental analyses by ICP-AES of purified pili in the absence or presence of EDTA

| Metal | Lower LOD (ppm)[a] | Lower LOD ($10^{16}$ atoms)[b] | Elements ($10^{16}$ atoms)[c] | Elements/EDTA ($10^{16}$ atoms)[d] |
|---|---|---|---|---|
| Al | 0.06 | 0.13 | 0.464 ± 0.349 | <LOD |
| Sb | 0.09 | 0.05 | | |
| As | 0.08 | 0.06 | | |
| Ba | 0.06 | 0.03 | <LOD | <LOD |
| Be | 0.09 | 0.60 | | |
| B | 0.10 | 0.56 | <LOD | <LOD |
| Cd | 0.06 | 0.03 | <LOD | <LOD |
| Ca | 0.05 | 0.08 | 0.222 ± 0.192 | <LOD |
| Cr | 0.06 | 0.07 | <LOD | <LOD |
| Co | 0.06 | 0.06 | <LOD | <LOD |
| Cu | 0.07 | 0.07 | | <LOD |
| Fe | 0.05 | 0.05 | 0.118 ± 0.1 | <LOD |
| Pb | 0.06 | 0.02 | <LOD | <LOD |
| Mg | 0.03 | 0.07 | 0.134 ± 0.116 | <LOD |
| Mn | 0.10 | 0.11 | <LOD | <LOD |
| Mo | 0.05 | 0.03 | <LOD | <LOD |
| Ni | 0.10 | 0.10 | <LOD | <LOD |
| P | 0.09 | 0.18 | 4.499 ± 3.906 | <LOD |
| K | 0.50 | 0.77 | 3.671 ± 3.120 | <LOD |
| Se | 0.09 | 0.07 | | |
| Si | 0.50 | 1.07 | <LOD | <LOD |
| Ag | 0.10 | 0.06 | | |
| Na | 0.50 | 1.31 | 38.337± | 6.867 |
| Sr | 0.05 | 0.03 | <LOD | <LOD |
| Tl | 0.05 | 0.01 | | |
| Ti | 0.10 | 0.13 | | |
| V | 0.15 | 0.18 | | |
| Zn | 0.05 | 0.05 | <LOD | <LOD |

[a] Instrumental Limits of Detection (LOD)
[b] Calculated for total volume of 1 ml.
[c] Elements detected in purified pili preparations (<LOD, lower than lowest detection limits)
[d] Elements detected in purified pili preparations after EDTA treatment (<LOD, lower than lowest detection limits)

The pili were also treated with low (0.1 mM) concentrations of EDTA to remove weakly bound elements carried over during the course of purification. Among the metal ion cofactors known to catalyze electron transfer (Fe, Cu, Mo) or redox (Fe, Cu, Mn, Co and Ni) reactions, only Fe was detected (0.19±0.14 atoms per pilin). However, as indicated by the data in Table 5, Fe levels varied widely from sample to sample, suggesting it was a trace contaminant rather than a tightly bound cofactor. Mild treatment with EDTA effectively removed it from the pili samples.

Quinones such as ubiquinones and menaquinones are lipid soluble molecules that function as the primary electron carriers of the bacterial inner membrane and serve as electronic link to membrane-bound respiratory complexes, a process that requires quinones to bind to specific structural motifs in quinone-reactive redox proteins (Fisher & Rich, *J. Mol. Biol.* 296, 1153-1162 (2000); Gunner et al. *J. Bioenerg. Biomembr.* 40, 509-519 (2008); Simon & Kern *Biochem. Soc. Trans.* 36, 1011-1016 (2008)). Because of their hydrophobic nature, quinones bind motifs located in hydrophobic regions of redox proteins (Fisher & Rich, *J. Mol. Biol.* 296, 1153-1162 (2000)). Type IV pili are predicted to have a narrow (6-11 Å) hydrophobic central channel. Because the pilus is anchored on the inner membrane of Gram-negative bacteria, its inner hydrophobic channel could potentially house quinones and create an internal pathway for electron transfer free of solvents. However, fluorescence spectroscopy of the purified nanowires revealed no emission peak in the 400-500 nm emission ranges of all the known quinones (See Cory and McKnight. Fluorescence Spectroscopy Reveals Ubiquitous Presence of Oxidized and Reduced Quinones in Dissolved Organic Matter. Environ. Sci. Technol. 2005, 39, 8142-8149). An emission peak at a 305 nm wavelength was detected, but this peak corresponds with nanowire tyrosine residues and not to quinones.

Moreover, when the nanowire structure was opened up using partial denaturation of the nanowire with 8M urea for two (2) hrs at room temperature, no internal quinones were exposed as a result. Denatured samples showed the tyrosine peak at above 300 nm and a large peak close to 350 nm, which is consistent with loss of tyrosine fluorescence quenching as the protein structure is denatured.

The results presented thus far demonstrated the proteinaceous composition of the purified pili, and rule out its association with both organic and inorganic redox-active cofactors.

The purified pili were also used to investigate the contribution of the pilus protein matrix to extracellular electron transfer in *G. sulfurreducens*. Scanning tunneling microscopy (STM) was used to probe the axial (lateral) conductivity of purified pili. STM provides a higher spatial resolution probe and permits more direct electronic characterization compared to the CP-AFM approach used in earlier work to demonstrate the conductive nature of mechanically-sheared pili preparations. No chemical fixation was used to prevent potential artifacts. Applying a voltage causes electrons to tunnel from occupied states at the sample surface into unoccupied states of the tip, or vice versa. As the amount of tunneling current is proportional to the number of available electronic states, STM can probe the local density of states of the pili and measure the contribution of individual amino acids in the protein matrix. The method has been successfully applied to study the surface topography and electronic properties of biological samples.

Figure 6A:
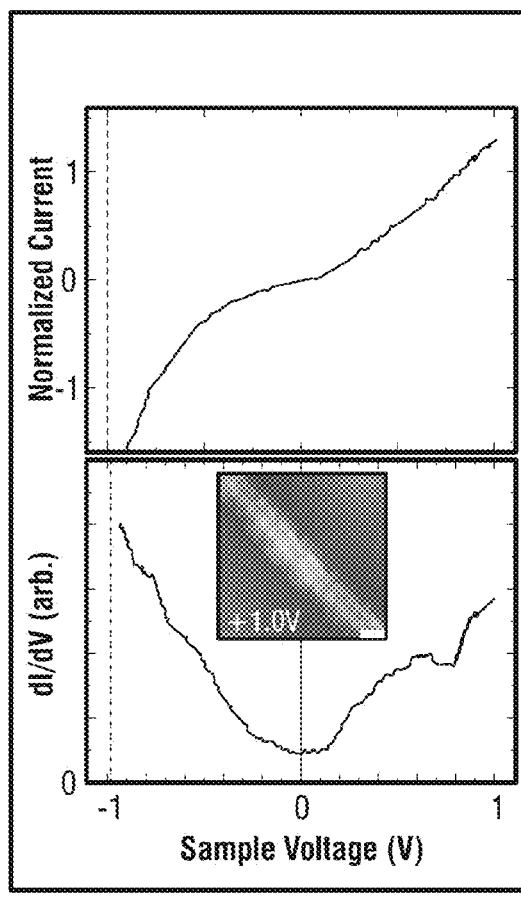
FIGS. 6A-C illustrate the conductivity of purified wild-type *Geobacter* pili.
Figure 6B:
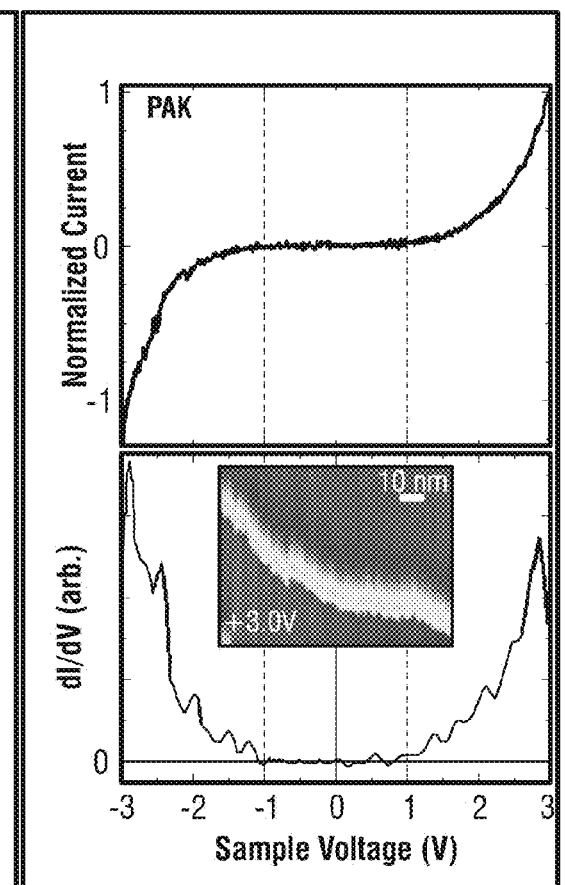

STM imaging of purified pili showed periodic conducting filaments of the expected diameter (FIGS. 6A and 6B). Bright spots were observed in the pilus. These bright spots are not taller in the topographical sense, but represent regions of the pilus that supply more tunneling current due to an increase in the local density of states. These bright locations are probably due to molecular sub-structures, consistent with the presence of conductivity 'hot spots' such as redox-active amino acids. Current (I) versus voltage (V) measurements taken at various locations of the pilus confirmed the metallic (ohmic) behavior at biological (±1 V) voltages (FIGS. 6A and 6B).

Controls with non-conductive purified pili from *Pseudomonas aeruginosa* strain K (PAK) were used to demonstrate the insulating behavior of other pili at biologically-relevant voltages. Large sample voltages, greater than 2 V, were necessary to image the PAK pili. At these voltages, tip instabilities often result due to the large electric field between the tip and the sample, which causes distortions and noise in the imaged data. This was even more pronounced for the pilus nanowires, due to the high tunneling rates produced by such highly conductive materials at high-voltages. The PAK pili thus serve as insulating controls in the ±1 V range, which represent biologically relevant voltages (often in the mV range). The PAK's distal conductivity at high voltages possibly reflects electron transfer through the peptide backbone. These results demonstrate that the protein casing of the pilus nanowires can conduct electrons laterally at ±1 V voltage ranges. In contrast, structurally similar protein filaments such as the PAK pili cannot. These results suggest that specific amino acids in the pilus nanowires function as electronic conduits to promote electron transfer reactions.

The STM studies presented above probed the distal conductivity of the pilus, thereby demonstrating that the protein matrix conducted electrons at distances in the same ranges as the pilus diameter (4-5 nm). In order to establish the upper range that the pilus protein matrix can conduct electrons, CP-AFM was employed to probe the axial (length) conductivity of pili deposited onto nanofabricated gold grids lying on an insulating silicon substrate. The conductive AFM tip was used to probe the conductivity of the pilus on the gold electrode (equivalent to the distal measurement) and these measurements were compared to the current measured when the tip was positioned at various points on the pilus filament lying on the insulating silicon substrate.

Figure 6C:
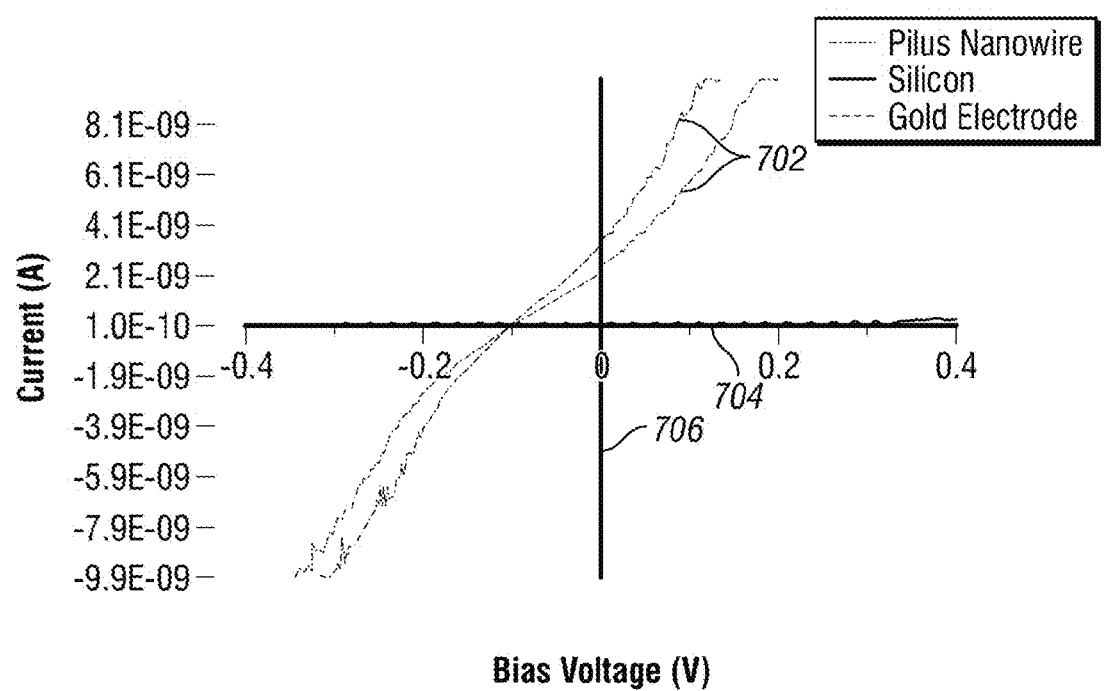

FIG. 6C demonstrates that Geobacter pilli can transfer electrons along their length. The data used for generating FIG. 6C were raw (non-normalized) data. However, curve 702 shows the current versus voltage with the AFM tip touching the purified pilus. As curve 702 shows, there is electrical conductivity along the axial length of the nanowire. The same pilus touches a gold surface electrode 200 nm away from the AFM tip. Therefore, the measurement shows the current passing from the tip, through the nanowire, and to the gold electrode. Curve 704 indicates that the AFM tip was touching the Si substrate 100 nm away from the gold edge and was not touching a nanowire. No measurable current results were observed.

For the positive control 706, the AFM tip was directly positioned on the gold electrode. As FIG. 6C shows, the conductivity of the direct tip-to-gold pathway was large.

The I-V curves clearly demonstrate, for the first time, the conducting behavior of the pilus with respect to axial conductivity, consistent with the conducting behavior previously demonstrated in distal measurements by CP-AFM (Reguera et al. *Nature* 435, 1098-1101 (2005)). Moreover, this behavior is consistent with similar mechanisms of the protein matrix mediating both distal and axial charge transport in the pili.

These results demonstrate that the protein matrix of the pili of *G. sulfurreducens* can, by itself, catalyze electron transfer reactions at distances that greatly exceed the known limits for protein-based electron transfer.

Furthermore, these results rule out any contribution from organic and inorganic cofactors known to mediate long-range electron transfer in proteins and support, instead, a mechanism exclusively mediated by the protein matrix. A solvent-free pathway through the pilus central channel mediated by quinones is not plausible because external organic molecules were extracted with ethanol from the conductive pili during purification and no emission peaks were detected by fluorescence spectroscopy to purified nanowires or partially denatured nanowires. The hydrophobic nature of the inner pilus channel also prevents solvents from filling the pilus internal cavity, so that electron transfer can proceed efficiently through an inner electrolytic channel. In support of this, elemental analyses by ICP-AES detected only trace amounts of the alkali metal sodium after removing weakly bound ions with EDTA. See Table 6 below.

TABLE 6

Atoms per pilin detected by ICP-AES analysis of pili samples

|  | atoms/pilin | Std Dev[a] |
|---|---|---|
| Al | 0.801 | 0.252 |
| Ca | 0.348 | 0.301 |
| Fe | 0.189 | 0.140 |
| K | 5.835 | 4.561 |
| Mg | 0.209 | 0.182 |
| Na | 60.080 | 52.080 |
| P | 7.050 | 6.121 |

[a]Standard deviation of three replicates

The measured concentrations varied from sample to sample without affecting the conductivity measurements of the pili preparations, suggesting they do not provide sufficient ionic strength to contribute to the pilus conductance. The pilus nanowires also lacked associated metals that are biologically relevant. From all the inorganic elements known to participate in electron transfer and redox catalysis in biological systems, only some low levels of iron were detected in samples that were not treated with EDTA. Again, there was a lot of variability from sample to sample, with samples lacking any detectable levels of Fe, yet producing consistent I-V curves by STM and CP-AFM. Samples with the highest levels of Fe had the equivalent of one atom of iron per 5 pilin subunits assembled along the pilus shaft.

With an estimated assembly of 3.6 pilin subunits per turn and a pilus pitch of 37 Å, the distance between potential iron redox centers in the pilus would exceed 51 Å. This is close to 5 times the optimum distance (<14 Å) established for electron transfer between metal-containing redox centers. Other metals such as boron or cadmium, which are commonly used to metalize insulating materials during the manufacturing of inorganic nanowires were also below the limits of detection. Electron transfer over distances beyond the 25 Å theoretical and experimental tunneling limits supports the involvement of multistep tunneling (hopping), single-step superexchange tunneling pathways and/or yet to be discovered transport mechanisms mediated by the protein matrix.

Example 6

Method II for Purifying Pili to Homogeneity

In this example, pili, purified as assemblies of a single peptide subunit, the PilA pilin, and without any associated proteins, such as c-cytochromes, or metals are shown to be conductive. Metals, ions and other known redox cofactors such as flavins and quinones were also absent.

Starting Materials

The starting materials as well as the bacterial strains and culture conditions were as described in Example 5.

Isolation and Purification of Pili

Pili were purified to homogeneity as described in Example 5 except that all the buffers used during the purification contained 1 mM ethylenediaminetetraacetic acid (EDTA) and all drying steps were carried out with a constant flow of filter-sterilized $N_2$ gas rather than in a Speed Vac (which may introduce contaminants in the pili samples).

Unless otherwise indicated, dried preparations of purified pili were resuspended in 10 mM CHES buffer containing 1 mM EDTA and incubated for a minimum of 24 h at 4° C. to deaggregate the pili bundles that formed during purification. A 2:1 (v/v) chloroform-methanol solution was then added to the pili samples to extract quinone-like contaminants following the method in F. Brito, J. A. DeMoss, M. Dubourdieu, *J.*

*Bacteriol.* 177, 3728 (July, 1995). After 2 h at 4° C., the chloroform phase was removed and discarded. The methanol was then evaporated with a constant flow of filter-sterilized $N_2$ gas and the dry pili sample was stored at −20° C. for short-term use or flash frozen in liquid nitrogen and stored at −80° C. for long-term use.

*Pseudomonas aeruginosa* strain K (PAK) pili were purified as described in W. Paranchych et al., *Can. J. Microbiol.* 25, 1175 (October, 1979), with some modifications. Briefly, PAK cultures grown in TBS to late-exponential phase were plated on TBS agar plates and grown overnight at 37° C. The cells were harvested from the plates and suspended in standard saline citrate buffer, SSC (1 g of wet weight per 10 ml SSC). Pili and flagella were sheared off the cells mechanically by stirring the cell suspension at 4° C. for 2 h and vortexing 5 times (1 min each cycle). Bacterial cells were removed by centrifugation (8000×g, 20 min). Pili and flagella were precipitated out of the supernatant fractions with NaCl (0.5 M) and polyethylene glycol 6000 (PEG 6000, 1% w/v) after overnight incubation at 4° C. The pili and flagella precipitates were harvested by centrifugation (6000×g, 25 min) and separated after incubating the samples at 4° C. in a 10% w/v $(NH_4)_2SO_4$ solution (pH 4.0) for 2 h. After centrifugation (6000×g for 15 min), the supernatant fraction containing the flagella was discarded. Three sequential steps of ammonium sulfate precipitation were used to remove any remaining flagella from the pili samples. The final pellet, containing the purified PAK pili, was resuspended in $ddH_2O$ and dialyzed for 24 h to remove any remaining $(NH_4)_2SO_4$. The dialyzed solution was used for STM experiments.

Protein concentration in the pili preparations was determined with the bichinchoninic acid (BCA) assay (S8) (Pierce®, Thermo Scientific) and using 60° C. incubations for 1 h. Bovine Serum Albumin (BSA) was used as the protein standard.

Microscopy

For Transmission Electron Microscopy (TEM), purified pili were resuspended in $ddH_2O$ (adjusted to pH 7) to visualize the pili bundles or in 10 mM CHES buffer (pH 9.5) and incubated at room temperature for 72 h to promote deaggregation. These samples were adsorbed onto a 300-mesh carbon-copper grids (Electron Microscopy Sciences), negatively stained with 1% (w/v) uranyl acetate, and allowed to dry, as described in Example 5. The samples were examined with a Jeol 100 CX electron microscope (Japan Electron Optic Laboratory) operated at 100 kV.

For Scanning Probe Microscopy, pili samples were routinely deposited on freshly cleaved highly oriented pyrolytic graphite (HOPG) and imaged with an atomic force microscope (AFM), as described in Example 5. Distal (lateral) and axial (length) conductivity measurements were performed by scanning tunneling microscopy (STM) and conductive probe-AFM (CP-AFM), respectively. For STM, dried preparations of *G. sulfurreducens* or PAK pili were resuspended in phosphate buffer saline (PBS) and deposited for 15-30 min. The excess liquid was wicked with absorbent paper and the HOPG surface was dry under a stream of $N_2$ gas. Applying a voltage with the STM causes electrons to tunnel from occupied states at the sample surface into unoccupied states of the tip, or vice versa. As the amount of tunneling current is proportional to the number of available electronic states, STM was used to probe the local density of states of the pili. This technique also provides a higher spatial resolution probe and more direct electronic characterization compared to conventional conducting probe-atomic force microscopy (CP-AFM) approaches.

For Scanning Tunneling Microscopy (STM) images were acquired at constant sample voltages, as indicated, by scanning while keeping the tunneling current constant with the use of a feedback circuit. The apparent STM width of the pilus fibers was obtained from cross sections and the broadening effect was corrected as described in Biró, L. P et al. Scanning tunneling microscopy (STM) imaging of carbon nanotubes. Carbon 36:689-696 (1998). The axial electronic structure of the pilus fiber imaged by STM was also generated to identify electronic (voltage-dependent) and topographic (present at all voltages) periodicities. I-V curves were obtained with the tip positioned on the center of the pilus filaments while suspending the feedback and ramping the bias voltage.

The tunneling conductance, dI/dV, was calculated as the numerical differentiation of the I over V values and plotted against the tip-sample bias (voltage. V) to investigate the density of states of the *G. sulfurreducens* pili as a function of energy and in reference to the PAK pili controls.

Conducting probe-atomic force microscopy (CP-AFM) was used to probe the axial conductivity of the *G. sulfurreducens* pili with a Bio-AFM-CF instrument (Asylum). The substrate used for pilus deposition and measurements was a gold electrode grid nanofabricated onto a silicon substrate. For the fabrication of the gold grid, photoresist (Shipley S1813) was spin-coated onto silicon wafers having a 300 nm thermal oxide layer $(SiO_2)$.

After photoresist development, patterned gold electrodes were deposited by thermally evaporating 5 nm of titanium followed by 25 nm of gold onto the surface of the wafer. A solution containing ca. 5 μg/ml of purified pili in $ddH_2O$ with 1 mM EDTA was then deposited onto the electrodes, left to adsorb for 10-20 min, and then wicked dry with absorbent paper. CP-AFM was performed with Pt-coated cantilevers having spring constant 2 N/m (Veeco).

Pilus nanowires lying across the gold-$SiO_2$ interface were first identified in imaging mode. For I-V measurements, the tip was placed on a point of the pilus lying on the $SiO_2$. Positive controls were generated by positioning the tip on the gold electrode, while negative controls were produced by positioning the tip on the $SiO_2$ substrate at 100-nm distances from the gold edge. The resistance of the pilus was calculated from the slope of the linear current-voltage (I-V) plot. Ohm's law (I=V/R) was used to estimate the current (in Amps) along the pilus. If a potential of 100 mV were applied across the length of this pilus, the current would be I=V/R=1e-1/2e8=5e-9=5 nano amps (=5 nA).

Protein Electrophoresis and Immunoblot Analyses

Dried preparations of purified pili were resuspended in 5 ml of $ddH_2O$ containing 10% (w/v) Octyl-b-D-Glucopyranoside (OG) (Sigma) and incubated at room temperature for 2 h. The concentration of OG was adjusted to 2% (v/v) and the solution was incubated for an additional 24 h at room temperature prior to SDS-PAGE. The OG-treated sample was boiled in SDS-PAGE sample buffer (S9) and subjected to electrophoresis on 10-20% Tris/Tricine ReadyGels (Bio-Rad) using a Mini Protean Tetra Cell apparatus (Bio-Rad). After SDS-PAGE separation, the proteins in the gel were electrophoretically transferred to a PVDF membrane (Hy-Bond LFP™, Amersham GE Healthcare) at 25 V for 150 min using a Mini Protean Tetra Cell apparatus (Bio-Rad).

The Amersham ECL Plex Western blotting kit was used for the electrophoretic transfer and membrane blocking, following manufacturer's recommendations. After blocking, the membrane was incubated for 90 min at room temperature and with gentle agitation in 10 ml of an antibody solution containing a 1:5,000 dilution of the primary antibody (rabbit anti-PilA polyclonal antibodies raised against the 42 amino acids at the carboxy-terminus of the PilA protein) and a 1:2,500 dilution of goat anti-rabbit IgG antibodies conjugated to the Cy*tm* 5 fluorescence dye (ECL™ Plex, Amersham GE Healthcare). The membrane was washed 4 times (5 min each) in wash buffer (TBS-T, pH 7.4, 0.1% Tween 20) and rinsed three times in wash buffer without Tween 20.

The protein bands that hybridized with the anti-PilA antibodies were visualized after scanning the blot with a Typhoon imager (GE Healthcare Sciences) operated in fluorescence mode (excitation at 633 nm, 670 BP 30 filter, and PMT setting at 600 V).

Elemental Analyses

The SeqCHED web server (R. Levy, M. Edelman, V. Sobolev, *Proteins* 76, 365 (Aug. 1, 2009) within the SPACE tools suite (V. Sobolev et al., *Nucleic Acids Res.* 33, W39 (Jul. 1, 2005)) of the Weizmann Institute of Science were used to identify conserved metal-ion binding sites in the translated gene sequence of the pilA gene (GSU 1496) of *G. sulfurreducens*. The amino acid sequence of the mature, processed pilin (starting at phenylalanine in position 11 (FIG. 2A), rather than the full length precursor, was used for these analyses. Information about this application and the metal-binding prediction algorithm can be found at the website ligin.weizmann.ac.il/seqched/.

Quantitative elemental analysis of the purified pili preparations was performed by Inductively Coupled Plasma-Atomic Emission Spectrometry (ICP-AES) using a Thermo Jarrell-Ash Enviro 36 Inductively Coupled Argon Plasm (Chemical Analysis Laboratory, University of Georgia, Athens). For these experiments, samples of purified pili (ca. 15 μg/ml) were resuspended in 10 mM CHES buffer (pH 9.5, 1 mM EDTA) and analyzed in reference to blank control samples (same buffer without protein). The Lowest instrumental Limits of Detection (LOD) shown in Table 7 were obtained from the CAIS website, www.uga.edu/cais/analytical_services/chemical_analysis/elements2.htm. The LOD values and measurements (in ppm) were used to calculate the amount of atoms per pilin subunit.

TABLE 7

Lowest Instrumental Limits of Detection (LOD)

| Elemental analyses of G. sulfurreducens pili by ICP-AES | LOD[a] | | Pili elements |
|---|---|---|---|
| | ppm | atoms/pilin | (atoms/pilin)[b] |
| Al | 0.06 | 2.9 ± 0.9 | <LOD |
| Sb | 0.09 | 6.9 ± 2.1 | <LOD |
| As | 0.08 | 3.3 ± 1.0 | <LOD |
| Ba | 0.06 | 28.5 ± 8.6 | <LOD |
| Be | 0.09 | 1.3 ± 0.4 | <LOD |
| B | 0.10 | 31 ± 9.3 | <LOD |
| Cd | 0.06 | 3.8 ± 1.2 | <LOD |
| Ca | 0.05 | 1.6 ± 0.5 | 1.7 ± 0.9 |
| Cr | 0.06 | 3.1 ± 0.9 | <LOD |
| Co | 0.06 | 3.6 ± 1.1 | <LOD |
| Cu | 0.07 | 3.4 ± 1.0 | <LOD |
| Fe | 0.05 | 2.8 ± 0.8 | <LOD |
| Pb | 0.06 | 39.5 ± 11.9 | <LOD |
| Mg | 0.03 | 3.8 ± 1.1 | <LOD |
| Mn | 0.10 | 5.6 ± 1.7 | <LOD |
| Mo | 0.05 | 1.6 ± 0.5 | <LOD |
| Ni | 0.10 | 67.1 ± 20.2 | <LOD |
| P | 0.09 | 5.3 ± 1.6 | <LOD |
| K | 0.50 | 9.0 ± 2.7 | <LOD |
| Se | 0.09 | 0.9 ± 0.3 | <LOD |
| Si | 0.50 | 2.3 ± 0.7 | <LOD |
| Ag | 0.10 | 3.5 ± 1.1 | <LOD |
| Na | 0.50 | 54.9 ± 16.5 | <LOD |
| Sr | 0.05 | 1.8 ± 0.5 | <LOD |
| V | 0.15 | 9.1 ± 2.7 | <LOD |
| Zn | 0.05 | 2.4 ± 0.7 | <LOD |

[a]Lowest instrumental Limits of Detection (LOD)
[b]Average value and standard deviation of three biological replicates.

UV-VIS Absorption and Fluorescence Spectroscopy

Dry purified pili samples were resuspended in ½ volume of isopropanol and, then, ½ volume of ddH$_2$O. Standards with L-tyrosine, riboflavin and menaquinone were also prepared as solutions in isopropanol and ddH$_2$O, as described for the pili samples. Absorption spectra were collected with a Cary100 UV-Vis spectrometer (Varian) set to 2 nm bandpass. Fluorescence spectra were measured with QuantaMaster spectrometer (Photon Technology International), with 270 nm excitation and 5 nm bandpass. All spectra were collected at room temperature, in quartz cuvettes with 1 cm path length (Spectrocell Inc.)

Calculation of Fe(III) Oxide Respiratory Rates

Using rates of Fe(III) oxide reduction (measured as the production of Fe(II)) and cell growth (measured as number of cells from cultures doubling every 15 h) reported in G. Reguera et al., *Nature* 435, 1098 (Jun. 23, 2005), the electron transport rates per cell were inferred. From the linearity of Fe(II) production during the reduction of Fe(III) oxides, electron transport rates of $5 \times 10^{12}$ electrons per second were calculated. After dividing this number by the culture's growth yield ($5 \times 10^7$ cells after the reduction of ca. 40 mM of Fe(III) oxides) a respiratory rate of $\sim 10^5$ electrons per cell per second was estimated.

Despite the absence of mediators, the protein matrix conducted electrons axially and at rates several orders of magnitude above those measured during the respiration of Fe(III) oxides. These distances and rates greatly exceed the known limits for charge transport reactions through protein matrices and make the pilus nanowires a new paradigm in protein electron transfer.

Results

Figure 8A:
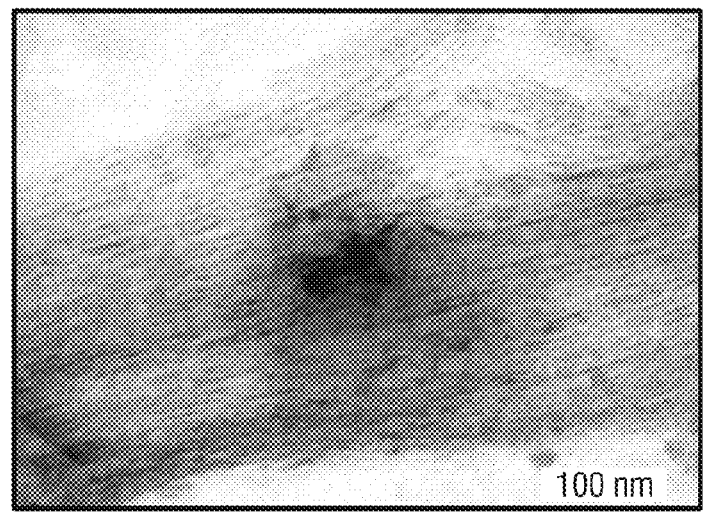
FIG. 8A-8C illustrate some of the structural features of *G. sulfurreducens* pili.
Figure 8B:
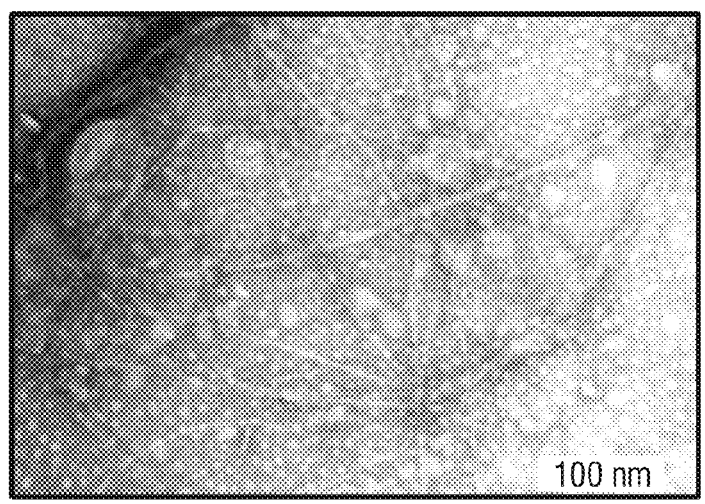
Figure 8C:
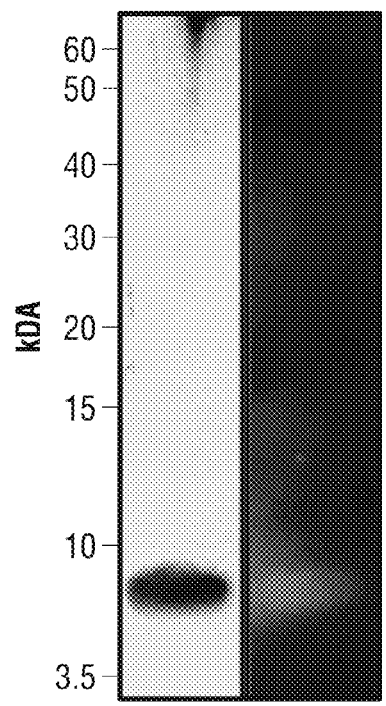

Electrostatic interactions between the pili during their purification at neutral pH resulted in thick bundles or ropes that did not solubilize in SDS and enabled their purification (FIG. 8A). These intermolecular interactions were effectively destabilized at basic pH and enabled the separation of the individual pilus fibers (FIG. 8B). The biochemical composition of the pili was analyzed by fully depolymerizing the fibers with octyl-glucoside and separated the pilus' protein components by denaturing SDS-PAGE. The depolymerization yielded a single peptide subunit with the apparent mass (ca. 6.5 kDa) expected for the mature PilA pilin and hybridized with anti-PilA antibodies (FIG. 8C). OmcS, a 50-kDa outer membrane cytochrome which has been hypothesized in C. Leang. X. Qian, T. Mester, D. R. Lovley, *Appl. Environ. MAicrobiol.* 76, 4080 (June, 2010) to adsorb to pili-like filaments in *G. sulfurreducens* and mediate conduction, was successfully removed during the purification.

Figure 7A:
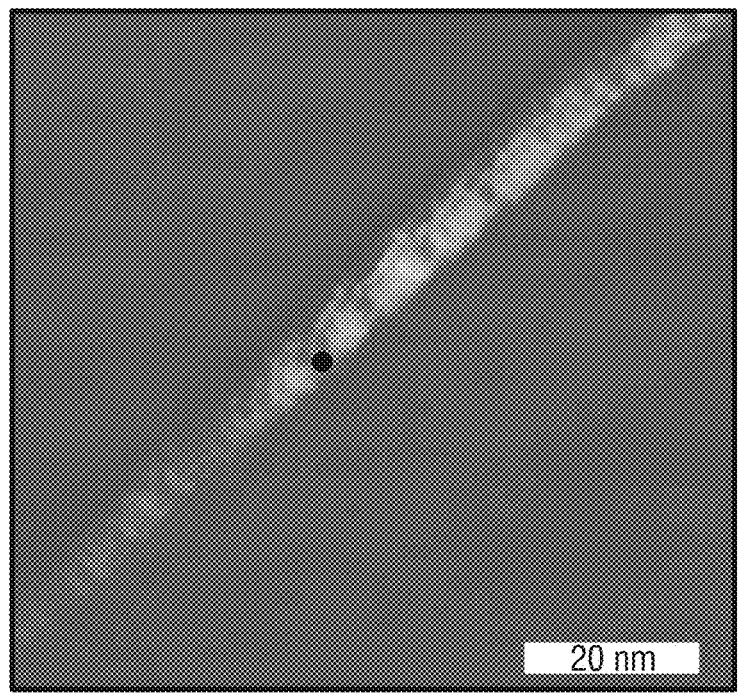
FIGS. 7A-C are images of wild-type *G. sulfurreducens* and *P. aeruginosa* strain K (PAK) pili.
Figure 7B:
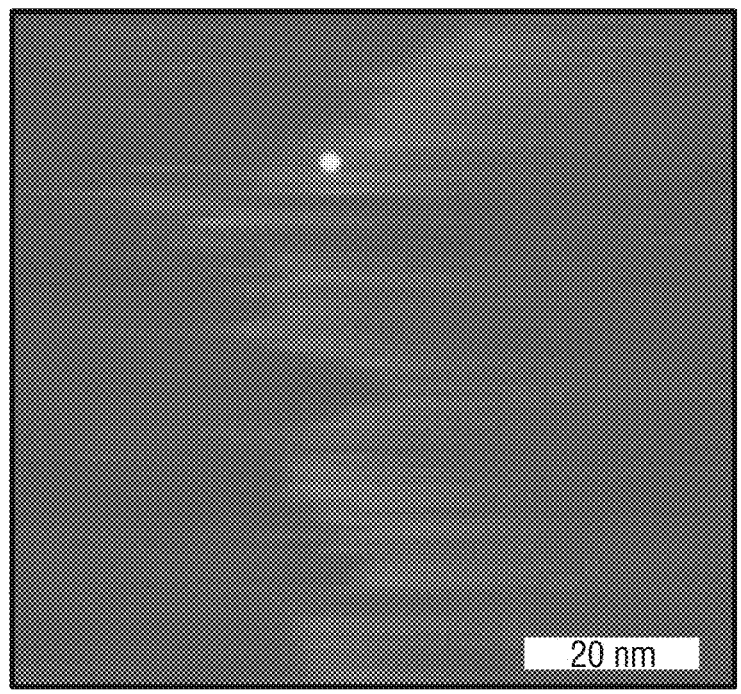
Figure 7C:
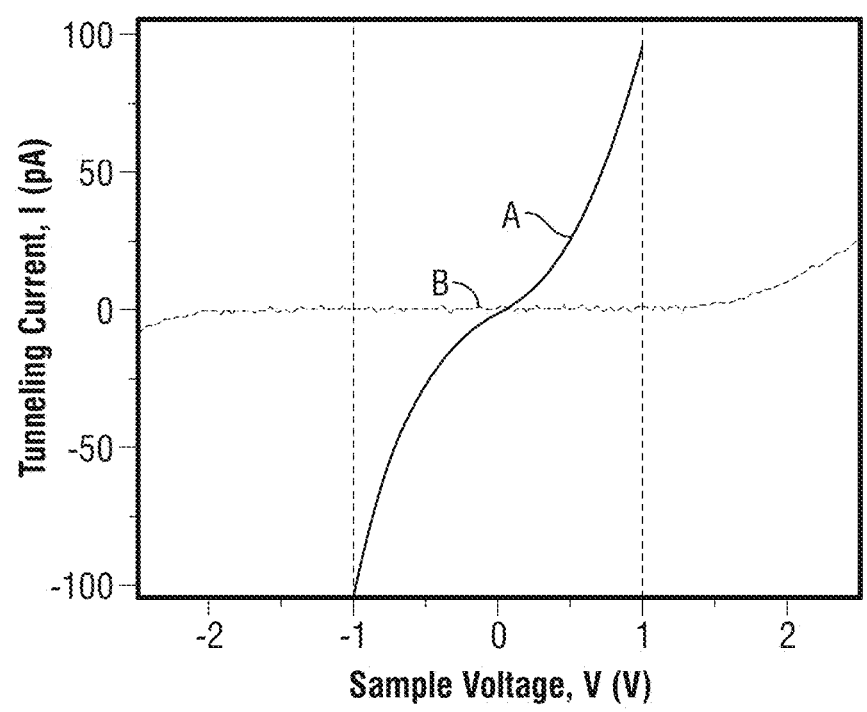

Despite the absence of proteins other than the PilA subunit, the pili were conductive by scanning tunneling microscopy (STM) (FIGS. 7A-7C). STM imaging of the purified pili showed conducting filaments with periodic molecular substructures, corresponding to regions of the pilus that supply more tunneling current due to an increase in the local density of states (FIG. 7A).

Figure 9:
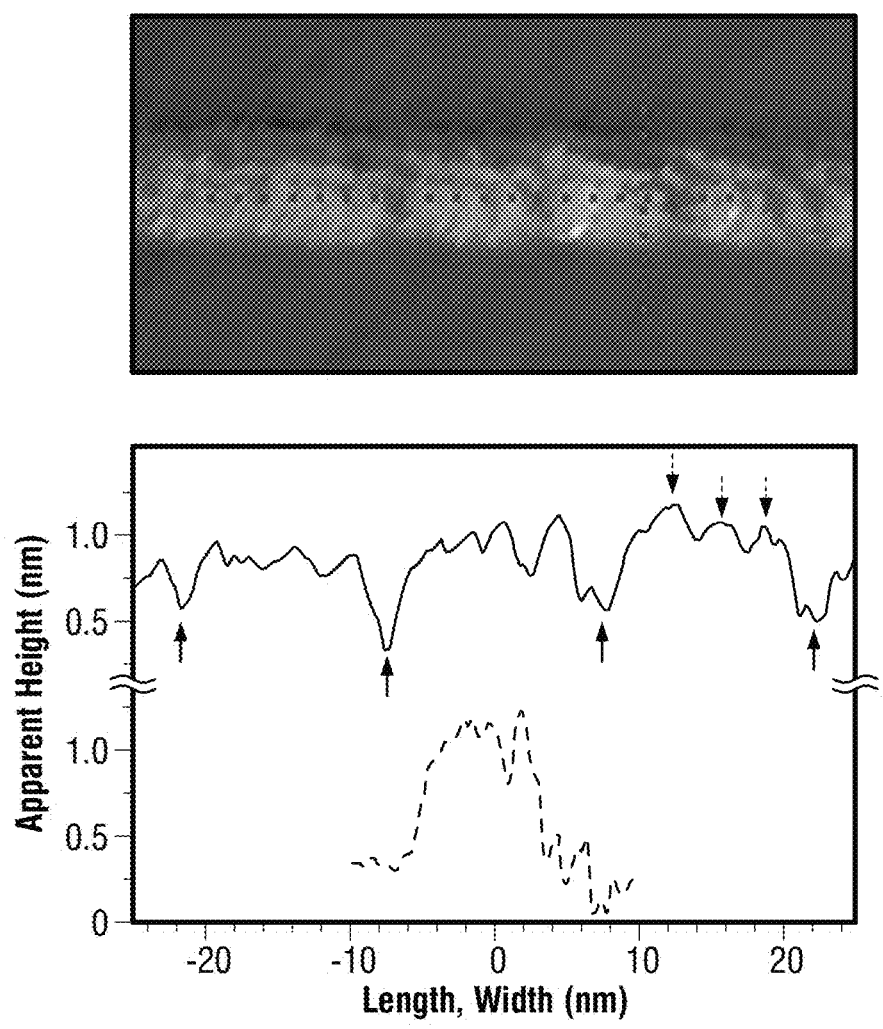
FIG. 9 is a STM topographical image (top) with height measurements (bottom) of a section of the pilus fiber acquired in constant current mode (0.5V, 100 pA).

FIG. 9 shows a STM topographical image (top) and height measurements (bottom) of a section of pilus fiber produced according to the method described in this Example and acquired in constant current mode (0.5V, 100 pA). The height graph, at the bottom, shows a large (ca. 10 nm) apparent width of the pilus fiber (lower curve), due to the distortion caused by the broadening effect of the tip as it crosses the pilus. The axial length measurements (upper curve) show voltage-dependent features every 14 nm (upward pointing arrows) and topographical peaks every 2-3 nm (downward pointing arrows). The axial periodicity included deep 14-nm repeating electronic features interspersed with 3-4 nm periodic topographic substructures (FIG. 9). The apparent STM width was ca. 10 nm (FIG. 9), yet produced ca. 5 nm widths once the distortion caused by the broadening effect of the tip while traversing the fiber was subtracted.

In contrast, pili purified from *Pseudomonas aeruginosa* strain K (PAK) were insulators in the ±1 V range and could only be imaged at large sample voltages (greater than 2 V) and low tunneling current set points (FIG. 7B). At these voltages, tip instabilities often result due to the large electric field between the tip and the sample, which causes distortions and noise in the imaged data. I-V (current vs. voltage) measurements taken at fixed locations of the pilus filaments confirmed the metallic (ohmic) behavior of the *G. sulfurreducens* pili at biological (±1 V) voltages and the insulating behavior of the PAK pili (FIG. 7C).

Figure 10A:
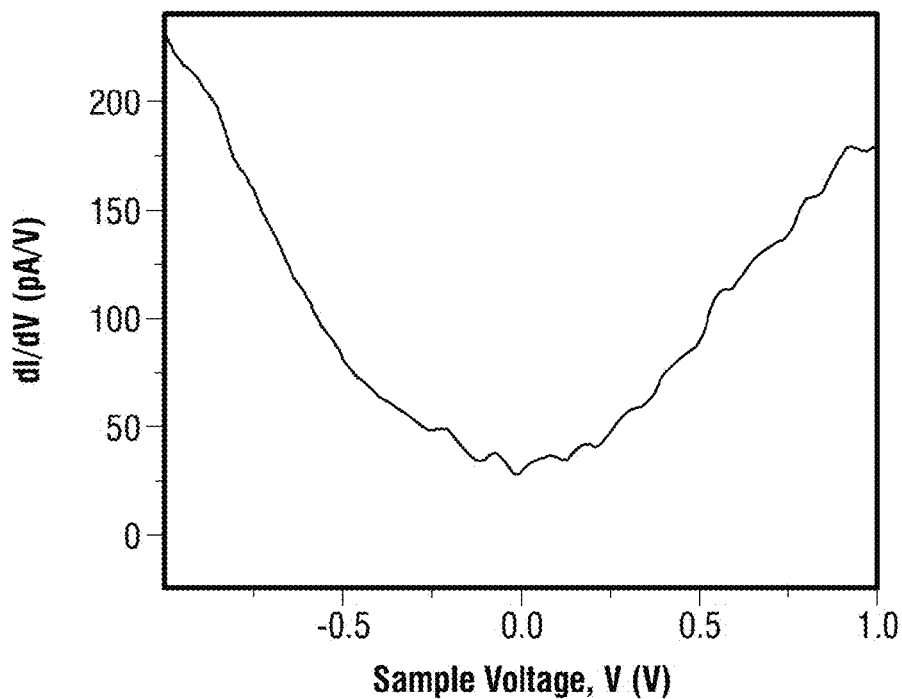
FIGS. 10A and 10B illustrate the tunneling conductance, dI/dV, of *G. sulfurreducens* pili (FIG. 10A) and the *P. aeruginosa* strain K pili controls (FIG. 10B).
Figure 10B:
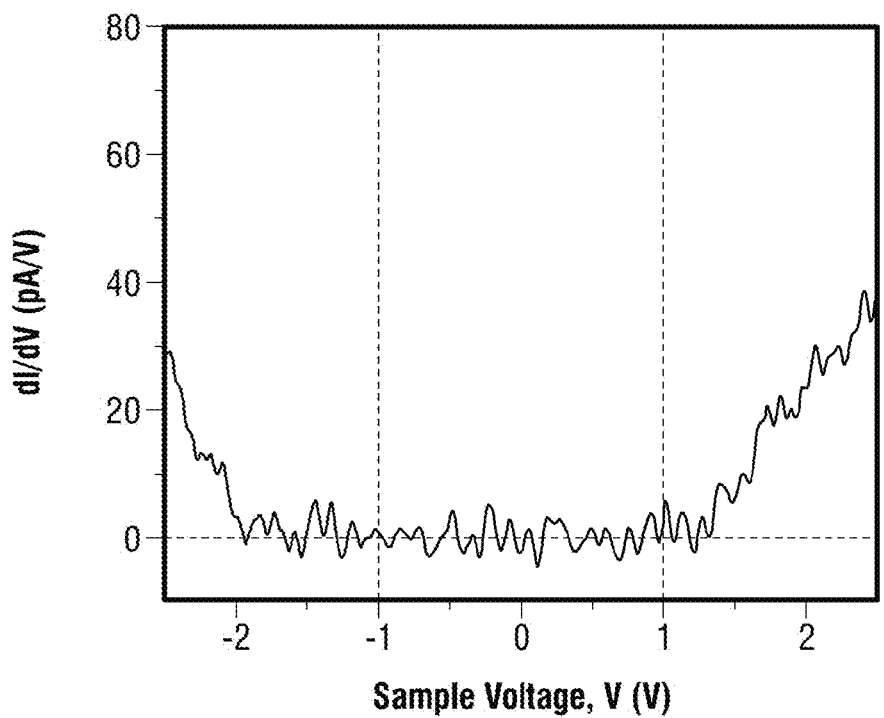

FIGS. 10A and 10B show tunneling conductance, dI/dV, of the *G. sulfurreducens* pili (FIG. 10A) and the PAK pili controls (FIG. 10B) obtained as the numerical differentiation of the I and V values shown in FIG. 7C and plotted against the tip-sample bias voltage (V). As FIG. 10A shows, the *G. sulfurreducens* pili produced a conductor-like spectrum with electronic states at low voltages, never reaching zero conductance. Furthermore, the plot of the conductance, dI/dV, versus the tip-sample bias voltage, V, revealed clear electronic states at low voltages, never reaching zero conductance in the *G. sulfurreducens* pili, which is consistent with the behavior of a true conductor. This is in contrast to the insulator-type spectrum of the PAK pili characterized by a large (±1.5-2 V) band gap at zero conductance (FIG. 10B). The STM analyses thus confirmed the unique electronic structure of the pili of *G. sulfurreducens* that enables them to function as electronic conduits.

The lack of proteins, other than the PilA pilin, in the purified pili excluded any contribution from c-cytochromes to its conductivity but did not exclude the possibility of metal mediators. Metals can bind to conserved structural protein motifs and mediate electron transfer reactions while stabilizing the protein's secondary structure. Although the predictive features of the SeqCHED server did not identify any conserved metal-ion binding sites in the PilA peptide subunit, the assembly of pilins in the pilus shaft could create structural and sequence motifs for metal coordination. Thus, we analyzed the elemental composition of the pili by inductively coupled plasma-atomic emission spectroscopy (ICP-AES).

Despite the high specificity and sensitivity of this technique at the identification and quantification of trace elements, inorganic elements known to catalyze electron transfer (Fe, Cu, Mo) and redox catalysis (V, Mn, Fe, Co, Ni, Cu and W) in biological systems were below detection limits (Table 6). Low levels of $Ca^{2+}$ were detected (1.7±0.9 atoms of $Ca^{2+}$ per pilin subunit), consistent with the known affinity of purified pili for this cation as discussed in J. C. McMichael, J. T. Ou, *J. Bacteriol.* 138, 976 (June, 1979) and its role at neutralizing the electrostatic interactions that promote pili aggregation (See L. Craig et al., *Mol. Cell* 23, 651 (2006)). This is in agreement with the biological role of $Ca^{2+}$ atoms at balancing charges in proteins as discussed in K. L. Haas, K. J. Franz, *Chem. Rev.* 109, 4921 (October, 2009).

Flavin cofactors, such as flavin mononucleotide (FMN) or flavin adenosyl dinucleotide (FAD), can also bind proteins and enable electron transfer and redox reactions. The presence of flavins in the pilus protein was investigated by UV-visible spectroscopy, based on the ability of the flavin's isoalloxazine ring to absorb light in the UV and visible spectral range. Quinones, such as ubiquinones and menaquinones, function as lipid soluble electron carriers between membrane-bound respiratory complexes, due to their ability to bind specific structural motifs in hydrophobic regions of quinone-reactive redox proteins. Type IV pili are anchored on the inner membrane of Gram-negative bacteria where they can accept quinones from the membrane-bound menaquinone pool. They also have a narrow (6-11 Å) hydrophobic central channel that could potentially house quinones and create an internal pathway for electron transfer free of solvents.

Figure 11A:
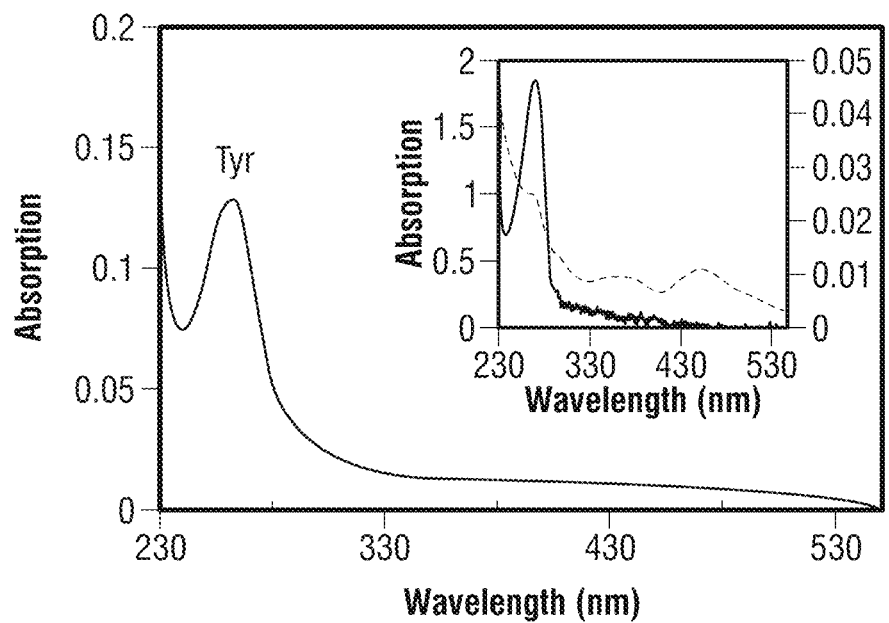
FIGS. 11A-C show spectra of *G. sulfurreducens* pili compared to various standards.

The purified pili absorbed strongly below 230 nm and at about 270 nm. FIG. 11A shows an absorption spectrum of the purified pili. The inset in FIG. 11A shows the same pili spectrum in comparison to riboflavin (dashed line), where the axes have been adjusted to scale.

Figure 11B:
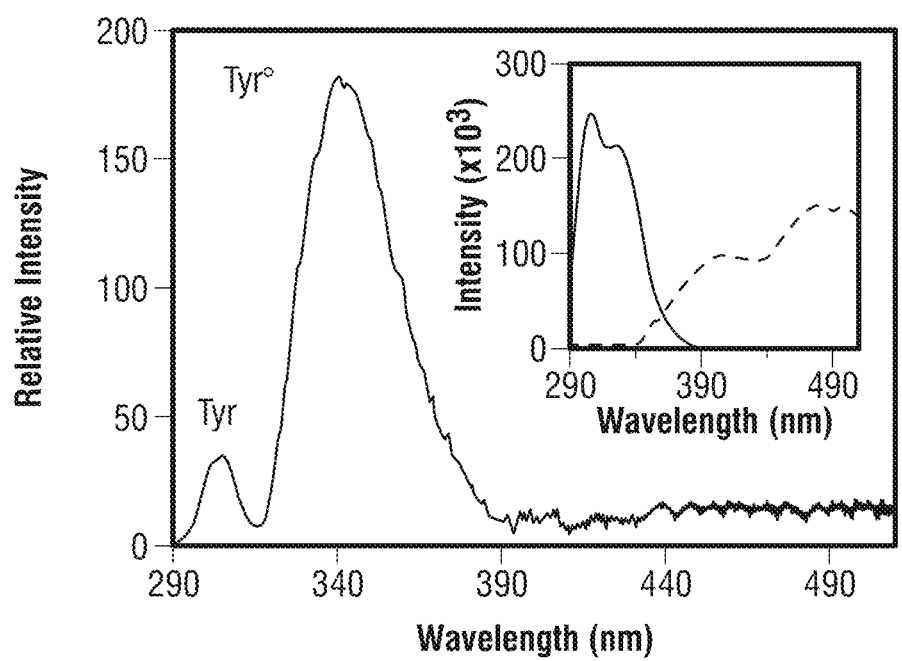

FIG. 11B shows a fluorescence spectrum of the purified pili, where the inset shows fluorescence intensity as relative fluorescence units corrected by a factor of $10^3$ with L-tyrosine (solid line) and menaquinone (dashed line) spectra. As with UV-VIS spectroscopy, the fluorescence emission from the pilin's tyrosines was used as a marker for the pilus protein in reference to an L-tyrosine standard solution. The pili spectrum produced two single peaks at ca. 300 and 340 nm, corresponding to the excitation peaks of tyrosine and its ionized form, tyrosinate, respectively. Ionization of the phenolic hydroxyl group in tyrosine is generated by a carboxylate group of a nearby aspartic or glutamic amino acid.

Note that tyrosines yield two fluorescence peaks corresponding to the tyrosine (Tyr) and tyrosinate (Tyr•) forms (FIG. 11B). These fluorescent spectra are consistent with the emission from peptide bonds and the pilin's tyrosine residues (FIG. 2A). Thus, the strong tyrosinate peak detected in the pili spectrum reflects the contribution of neighboring acidic residues (3 aspartic and 2 glutamic residues in the pilin, as shown in FIG. 2A). Such emission is generally discussed in C. R. Cantor, P. R. Schimmel, *Techniques for the study of biological structure and function*. Biophysical Chemistry vol. 2 (W. H. Freeman, San Francisco, 1980).

Figure 11C:
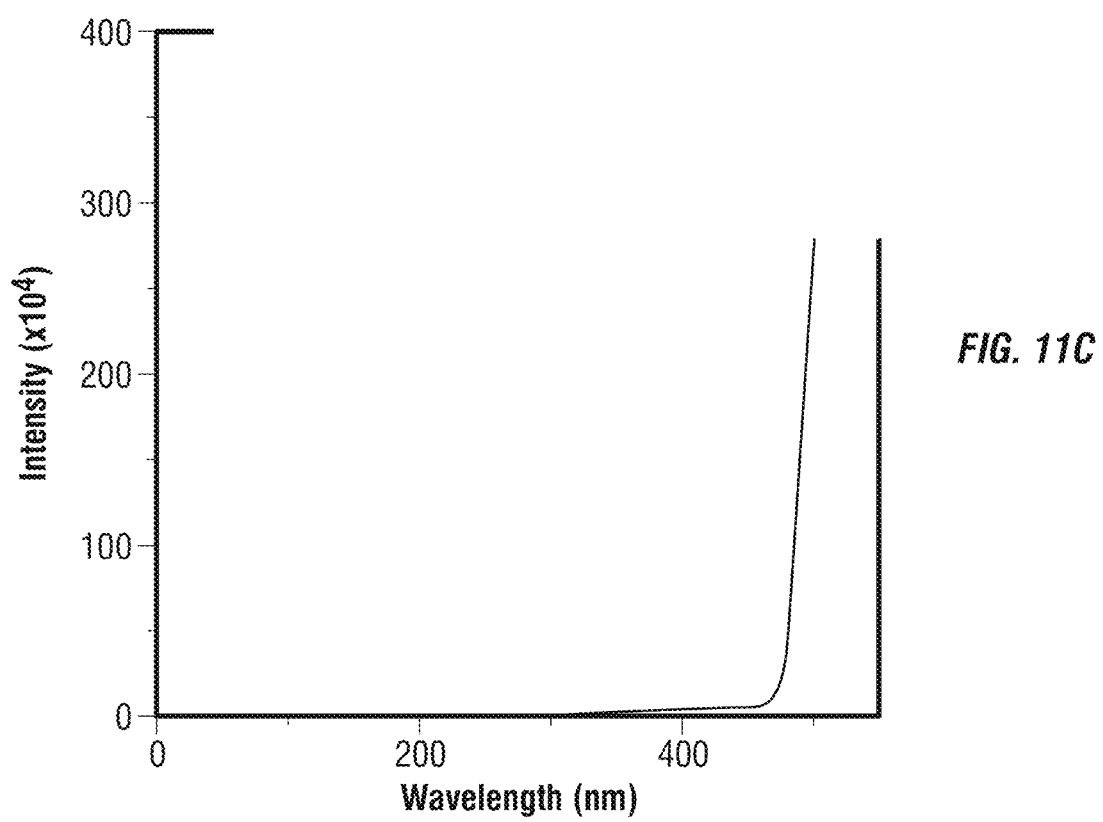

Notably, the pili spectra had no peaks in the visible region (at ~360 and ~450 nm) where flavins absorb. These results demonstrate that the pili are not flavoproteins and do not co-purify with flavoproteins. Coincidentally, flavins can also fluoresce at 440-470 nm wavelengths or higher (FIG. 11C), depending on the type of flavin cofactor and the nature of the flavin-binding site in the protein. However, the fluorescence spectrum of the *G. sulfurreducens* pili also had no peaks above 390 nm (FIG. 11B (inset)). Thus, despite their high quantum yield compared to tyrosines, flavins were not detected in the pili spectrum, providing additional, confirmatory evidence for the absence of flavins in the pili.

The finding that the *G. sulfurreducens* pili are conductive in the absence of other proteins and organic or inorganic cofactors demonstrates that the protein matrix is responsible for its conductance. Although electrons can travel through protein matrices, distance is limited to the <14 Å separation between the protein's redox centers that is required for optimal electron tunneling. The observed transport of electrons across the ca. 5-nm pilus width (FIGS. 7A-7C) indicates that the pilus protein assembly could enable charge transport at greater distances.

Figure 12A:
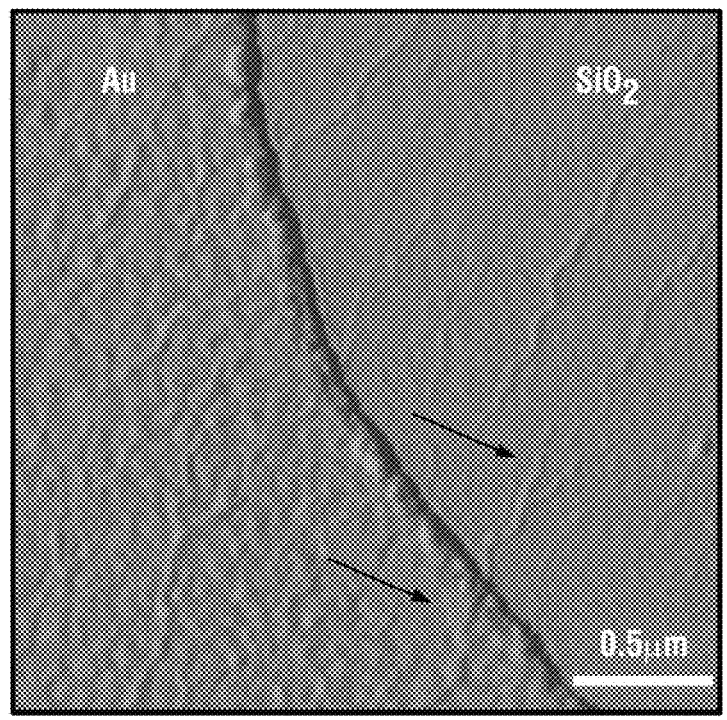
FIGS. 12A-C illustrate measurement of I-V (current-voltage) curves in purified pili.
Figure 12B:
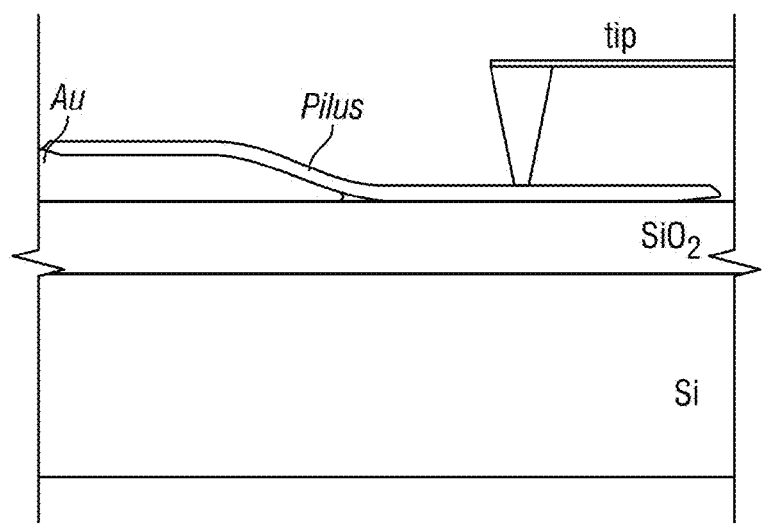
Figure 12C:
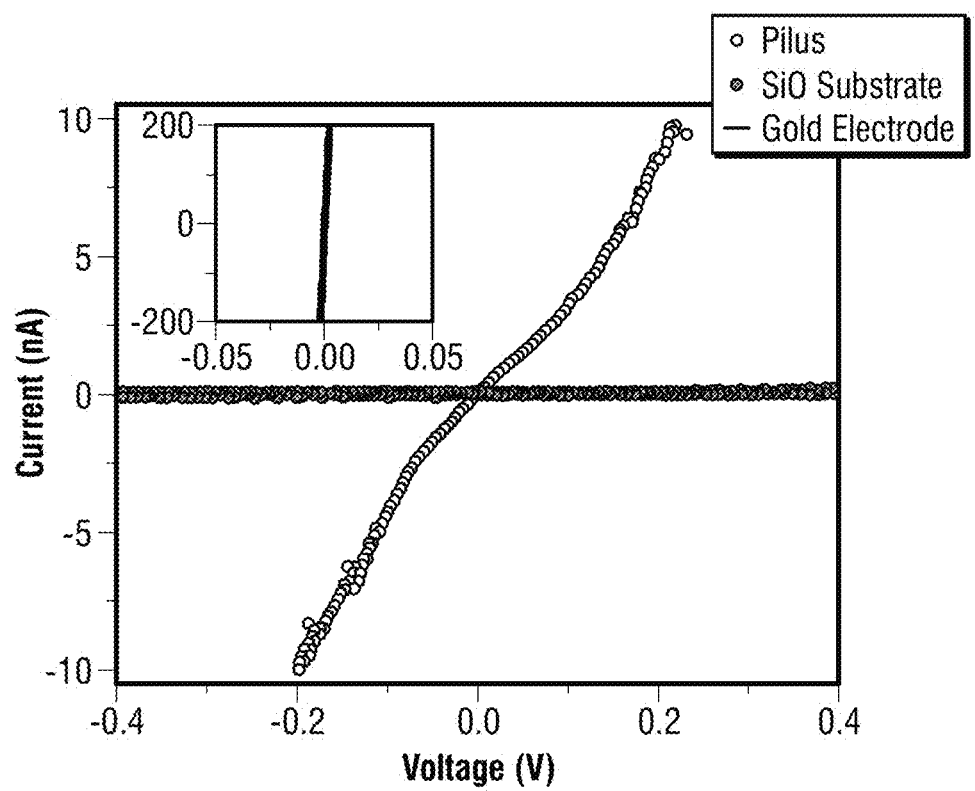

To further investigate this possibility, we used CP-AFM to measure the axial conductivity of individual pilus fibers deposited on gold electrodes nanofabricated onto an insulating $SiO_2$ substrate. FIG. 12A is an AFM image of pili deposited onto a 25-nm thick gold electrode nanofabricated onto an insulating $SiO_2$ surface with the arrows pointing to an example where a pilus clearly overlaps the edge of the gold electrode. FIG. 12B is a schematic of a two-point transport measurement between the gold electrode and a CP-AFM tip through a pilus filament. FIG. 12C show I-V (current-voltage) curves obtained with CP-AFM. The curve taken with the tip positioned on a pilus (red) was acquired at a location about 200 nm from the gold electrode. In contrast, negligible current was detected with the same tip in contact with the substrate at 100 nm from the gold edge (black). The inset shows data acquired with the same tip in contact with the gold electrode, with the same vertical and horizontal units as the large plot.

The current was linear when the tip was positioned on a pilus filament at 200-nm distances from the gold edge, while no current was detected when the tip was positioned on the silicon substrate at 100-nm distances from the gold edge. A resistance R=200 MΩ was measured along a 1 µm-long pilus and an electron transport rate of $3.1 \times 10^9$ electrons per second at a potential of 100 mV. The measured resistivity (ρ, "rho") was 0.4 Ω·cm. This number is less than half the lowest resistivity (1 Ω·cm) measured for *Shewanella* nanowires as discussed in M. Y. El-Naggar et al., *Proc. Natl. Acad. Sci. USA* 107, 18127 (Oct. 19, 2010), which rely on c-cytochromes for long-range electron transport as discussed in Y. A. Gorby et al., *Proc. Natl. Acad. Sci. USA* 103, 11358 (Jul. 25, 2006), and is even lower than moderately doped silicon nanowires (0.5 Ω·cm).

Based on the linearity of Fe(II) production and cell growth yields during the reduction of Fe(III) oxides by *G. sulfurreducens* respiratory rates of $10^5$ electrons per cell per second were calculated. These rates are several orders of magnitude lower than the rates of electron transport measured along the pilus. Thus, a single cell could discharge all the respiratory electrons onto the Fe(III) oxides with only one pilus. Yet cells from Fe(III) oxides cultures display several (>10) pili on one side of the cell, consistent with a biological strategy that maximizes the redox active surface of the cell without limiting the rate of electron transfer. Not surprisingly, adaptively evolved strains of *G. sulfurreducens* with increased rates of extracellular electron transfer also are hyperpiliated and have a reduced outer membrane c-cytochrome content.

These results demonstrate that *G. sulfurreducens* pili are protein nanowires and catalyze electron transfer reactions at rates (~$10^9$ electrons per second) that do not limit the respiratory rates of the cell during the reduction of Fe(III) oxides. Contribution from other proteins and from organic and inorganic cofactors were ruled out, thus supporting a mechanism exclusively mediated by the pilus' protein assembly. A solvent-free pathway through the pilus central channel mediated by quinones was not plausible because the conductive pili had no detectable quinones. The hydrophobic nature of the pilus' inner channel also prevents solvents from filling the pilus internal cavity, which is necessary for ionic conduction through an inner electrolytic channel. Furthermore, elemental analyses by ICP-AES did not detect any ionic species such as $Na^+$, $K^+$, $Ag^+$, $Li^+$ and $Cu^+$ that could have contributed to ionic conduction in an electrolytic core or in the solid state. Biologically-relevant metals, such as Fe, Cu, Mo, V, Mn, Co, Ni, and W, which are involved in biological electron transfer or redox processes, or metal dopants, such as B and Cd, which are commonly used to metalize insulating materials and inorganic nanowires were also below the limits of detection.

The ICP-AES technique used in this study had the sensitivity to detect several atoms of metals per pilin (Table 7). With an estimated distance of 10.5 Å between pilin heads in the pilus shaft, it would have taken at least one metal atom per assembled subunit to maintain optimal (<14 Å) tunneling distances. Yet despite the lack of metals, the pilus nanowires displayed metallic-like properties.

The ability of the pilus protein matrix to transport electrons over distances that greatly exceed the theoretical and experimental tunneling limits supports the involvement of multiple pathways such as multistep tunneling (hopping), single-step superexchange tunneling pathways and/or perhaps yet to be discovered transport mechanisms facilitated by the unique structural features of the *Geobacter* pilins and their assembly. The *Geobacter* pilin structure is divergent, as they lack the conserved C-t globular head of other bacterial pilins, such as the PAK pilins. This divergent structure may be adaptive and evolved in order to use the pili as electronic conduits. Furthermore, despite the structural conservation of the α1 domain (the conserved N-t 53-residue long of the α-helix that promotes hydrophobic interactions between the assembled pilins), amino acid conservation in the *Geobacter* pilins is restricted to the first 30-40 amino acids. These divergent amino acids could be positioned at optimal distances in the pilus shaft so as to provide pathways for electron transfer. Alternatively, these *Geobacter*-specific amino acids could affect subunit contacts during assembly, thereby affecting the pilus flexibility and mechanical properties so as to facilitate collision-exchange mechanisms and the electronic coupling of redox-active amino acids required for fast charge transport The finding that *G. sulfurreducens* pili are protein nanowires is significant for nanotechnological applications. The potential to customize the functional properties of proteins via well-established genetic engineering approaches far exceeds available methods for the functionalization of carbon nanotubes and inorganic nanowire surfaces. Furthermore, the conservation of the α1 assembly domain in the *Geobacter* pilins raises the possibility of mass-producing these nanowires by molecular self-assembly in a cell-free environment. This contrasts with fabrication methods for other types of nanowires, which involve high temperatures, toxic solvents, vacuums, and expensive equipment. Protein nanowires also circumvent major concerns regarding cytotoxicity and genotoxicity that limit commercial applications of carbon, metal, and metal-oxide based nanoparticles, making them suitable for the development of biodegradable and biocompatible nano-electronic devices and expanding the known applications of metallic nanowires.

Example 7

Yield of Nanowires Expressed by *Geobacter sulfurreducens*

To determine yields, cultures were grown at 25° C. according to the methods described in the above examples to induce the expression of nanowires. Cultures were also grown at 30° C. to produce otherwise identical cells, but without the nanowires.

The resulting cells were lysed and total cell protein was calculated for samples having a similar OD at approximately 600 nm, thus similar number of cells.

Although the expression of the nanowires changed, the total cell protein did not substantially change in these two cultures. For this reason, the 30° C. protein value was subtracted from the 25° C. value, with the resulting value used as the amount of protein corresponding to the nanowire in the starting culture. Protein assays to the purified nanowires resulting from the 25° C. culture were also performed.

The resulting yield was approximately 63%. It is likely that yields can be even higher with improved methods or with more accurate assays of pili production in the starting cultures.

Example 8

Molecular Rectifying Behavior of Purified Microbial Nanowires

Unless otherwise stated, materials and methods were as described in Example 5. Prior to analyses the dry purified pili were resuspended in ddH$_2$O with 1 mM EDTA to remove trace elements.

Figure 13:
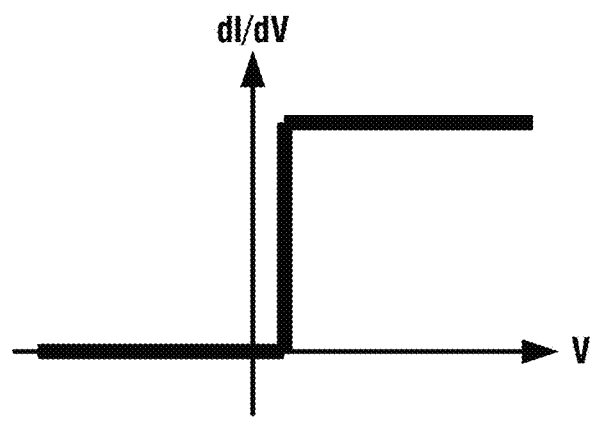
FIG. 13 shows a schematic density-of-states curve for an ideal rectifier.

The molecular rectifying behavior of purified microbial nanowires was demonstrated using scanning tunneling microscopy (STM). By probing the nanowire with a sharp tip, this electronic information can be resolved atom-by-atom. In addition to atomic scale images of the material, STM can monitor the tunneling current at a particular location as a function of the applied voltage. This information is directly related to the electronic density of states. A material with a high density of states acts as an electronic conductor. Likewise, a material with a low density of states acts like an insulator. In contrast, a rectifier, or diode, is an electronic component that acts as either a conductor or an insulator, depending on the sign of the voltage. The resulting action is that current can only flow in one direction. FIG. 13 illustrates the density of states for an ideal rectifier.

This example provides reproducible measurements showing rectifying behavior on the edges of microbial nanowires. In this example, cells of the bacterium *Geobacter sulfurreducens* were grown under nanowire-inducing conditions (incubation at 25° C.). The nanowires were purified as described in Example 5 and resuspended in ddH$_2$O in 1 mM EDTA. The purified nanowires were composed of a single peptide subunit that polymerizes via hydrophobic interactions to make the nanowire filament. The nanowires were adsorbed and air-dried onto a graphite surface prior to STM analyses. The STM tip was positioned on the nanowire to acquire electronic information.

Figure 14:
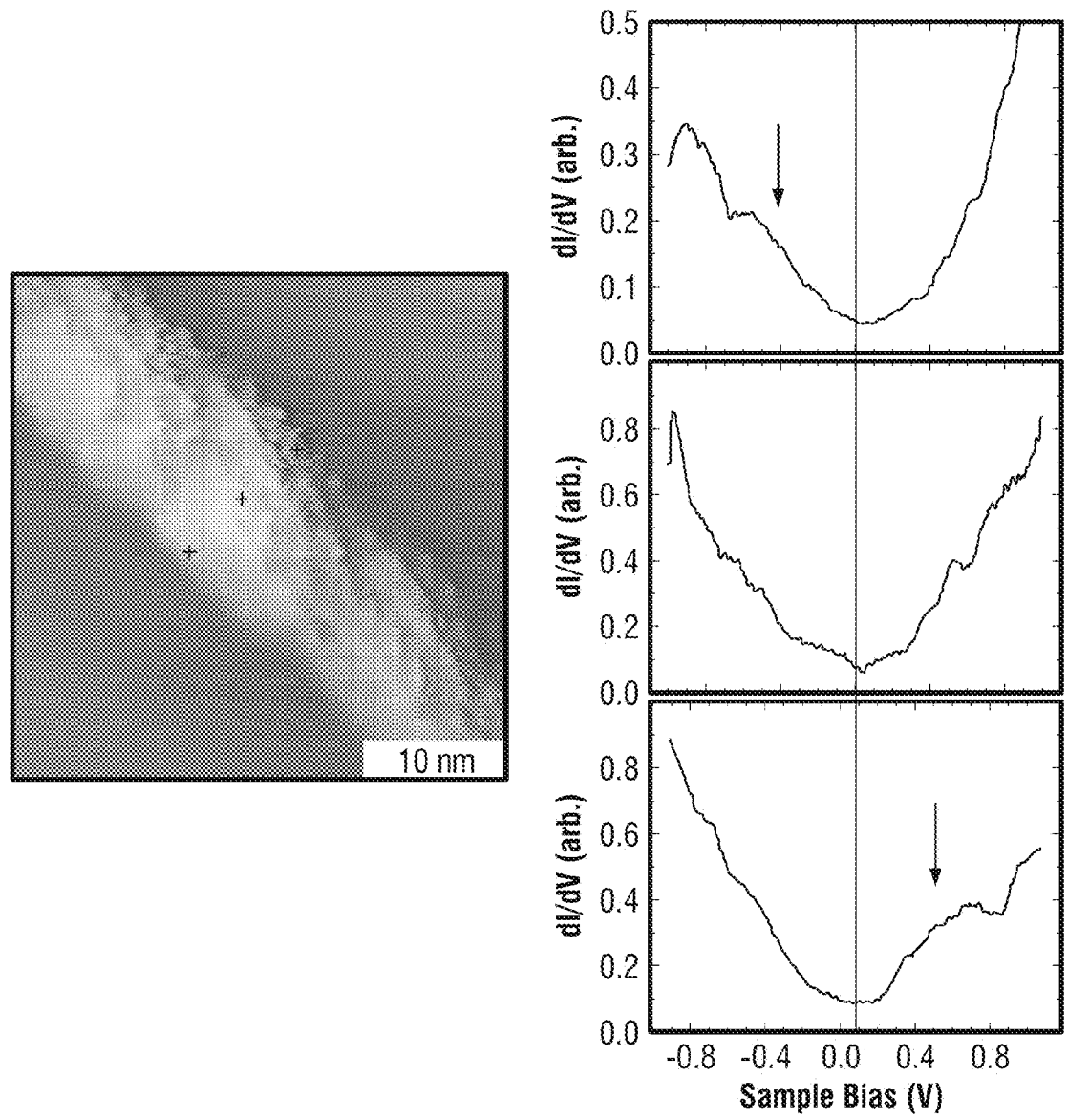
FIG. 14 is a STM topographical image (left) of a purified nanowire deposited onto a graphite surface together with three spectroscopic measurements of the electronic density of states (right) according to various embodiments.

FIG. 14 includes a STM topographical image (left) of a purified nanowire deposited onto a graphite surface together with three spectroscopic measurements of the electronic density of states (right). The top and bottom curves on the right panel were acquired at the top edge and bottom edge, respectively, at the locations indicated by the "+" symbols on the left image. The middle curve was acquired at the central "+" symbol. The blue arrows indicate enhanced density of states. The key features are highlighted by the arrows, which indicate enhanced density of states near ±0.4 V. As the enhancement depends on the sign of the voltage (i.e., the curves are asymmetric with respect to the horizontal axis), the overall behavior at low voltages, in the range of ±0.8 V, is consistent with a rectifier.

Figure 15:
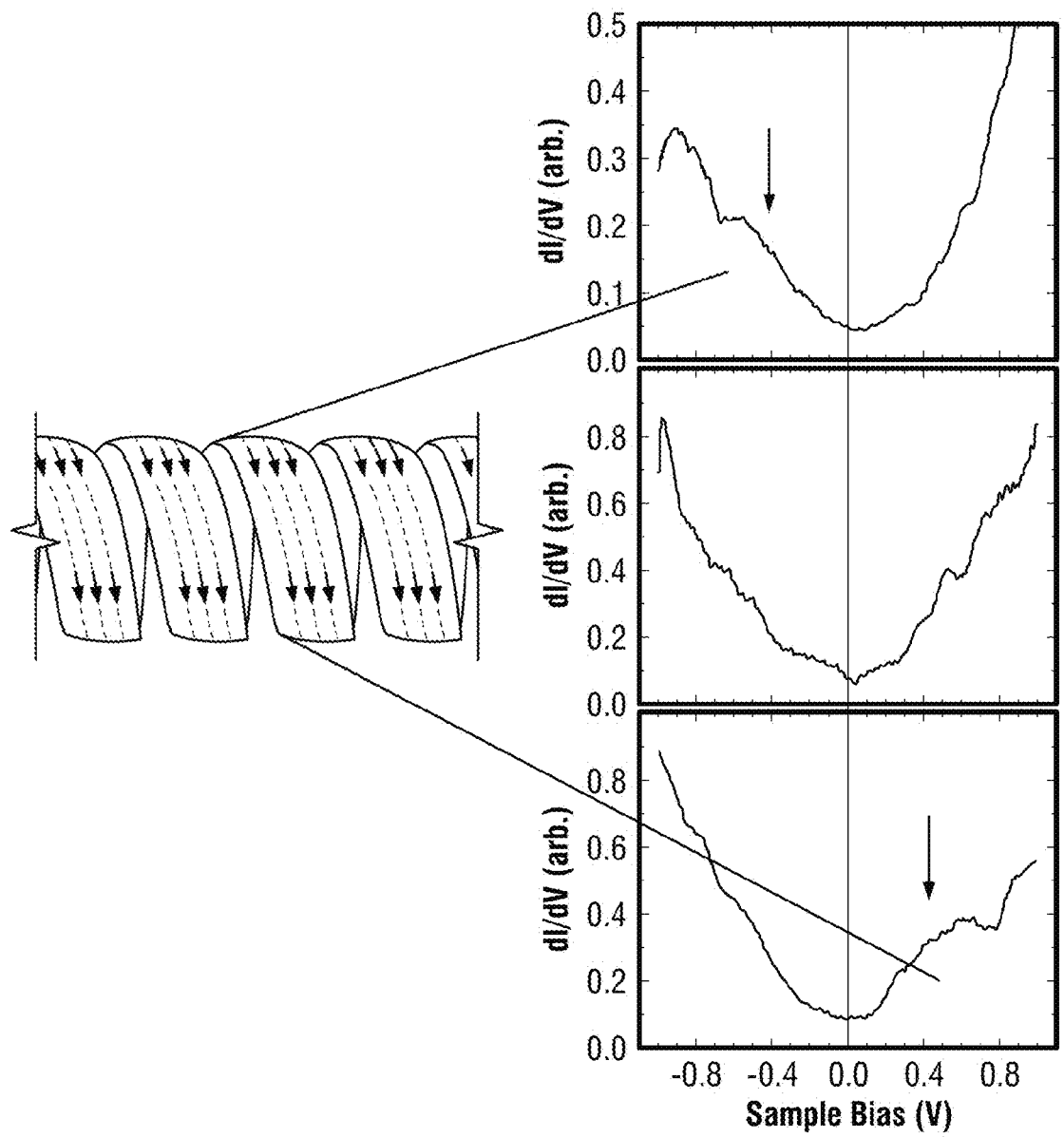
FIG. 15 shows a schematic of a likely charge path of the purified nanowire of FIG. 14 (left) correlated with the three spectroscopic measurements shown at the right side of FIG. 14.

Although the STM measurements show the density of states in the transverse direction (lateral conductivity), this behavior is consistent with rectifying behavior in the longitudinal direction (axial conductivity). This is illustrated schematically in FIG. 15. FIG. 15 (left) shows a likely charge path in the purified nanowire of FIG. 14. If the microbial nanowires were ohmic conductors, the plot would have been symmetrical. The enhanced density of states on opposite edges is consistent with rectifying behavior in the axial direction, given the likely helical path of current flow along the pilus.

The purified nanowires used in this example lack metals and are not associated with any redox protein or cofactor, as discussed above in Example 5 (and Example 6). Thus, the molecular rectifying behavior of microbial nanowires is a consequence of the biochemical nature of the nanowire (protein amino acid composition, structure, and chemical modifications). Because of this, genetic engineering can be used to modify the native rectification properties to produce customized rectifiers with electronic properties suitable for each particular application. The proteinaceous nature of these microbial rectifiers also makes them biodegradable and desirable for applications in nanomedicine. Furthermore, by using mass-production in recombinant hosts and in vitro assembly also the costs associated with nanowire and nanomedicine synthesis can be reduced. Additional testing will include two-probe and four-probe devices.

REFERENCES

1. Brittain, T. (2008) Intra-molecular electron transfer in proteins. *Protein Pept. Lett.* 15, 556-561
2. Gray, H. B., and Winkler, J. R. (2003) Electron tunneling through proteins. *Q. Rev. Biophys.* 36, 341-372
3. Laemmli, U. K. (1970) Cleavage of structural proteins during the assembly of the head of bacteriophage T4. *Nature* 227, 680-685
4. Collinson, S. K., et al. (1991) Purification and characterization of thin, aggregative fimbriae from *Salmonella enteritidis*. *J. Bacteriol.* 173, 4773-4781
5. Reguera, G., et al. (2005) Extracellular electron transfer via microbial nanowires. *Nature* 435, 1098-1101
6. Haas, K. L., and Franz, K. J. (2009) Application of metal coordination chemistry to explore and manipulate cell biology. *Chem. Rev.* 109, 4921-4960
7. Holm, R. H., et al. (1996) Structural and Functional Aspects of Metal Sites in Biology. *Chem. Rev.* 96, 2239-2314
8. Levy, R., et al. (2009) Prediction of 3D metal binding sites from translated gene sequences based on remote-homology templates. *Proteins* 76, 365-374
9. Sobolev, V., et al. (2005) SPACE: a suite of tools for protein structure prediction and analysis based on complementarity and environment. *Nucleic Acids Res.* 33, W39-43
10. Ma, R., et al. (2004) Speciation of protein-bound trace elements by gel electrophoresis and atomic spectrometry. *Electrophoresis* 25, 2469-2477
11. Fisher, N., and Rich, P. R. (2000) A motif for quinone binding sites in respiratory and photosynthetic systems. *J. Mol. Biol.* 296, 1153-1162
12. Gunner, M. R., et al. (2008) Modification of quinone electrochemistry by the proteins in the biological electron transfer chains: examples from photosynthetic reaction centers. *J. Bioenerg. Biomembr.* 40, 509-519
13. Simon, J., and Kern, M. (2008) Quinone-reactive proteins devoid of haem b form widespread membrane-bound electron transport modules in bacterial respiration. *Biochem. Soc. Trans.* 36, 1011-1016

14. Craig, L., et al. (2006) Type IV pilus structure by cryo-electron microscopy and crystallography: implications for pilus assembly and functions. *Mol. Cell* 23, 651-662
15. Pelicic, V. (2008) Type IV pili: e pluribus unum? *Mol. Microbiol.* 68, 827-837
16. Strom, M. S., and Lory, S. (1993) Structure-function and biogenesis of the type IV pili. *Annu. Rev. Microbiol.* 47, 565-596
17. Baro, A. M., et al. (1985) Determination of surface topography of biological specimens at high resolution by scanning tunnelling microscopy. *Nature* 315, 253-254
18. Wigginton, N. S., et al. (2007) Electron tunneling of outer-membrane decaheme cytochromes from *Shewanella oneidensis*. *Geoch. Cosmochim. Acta* 71, 543-555
19. Arikuma, Y., et al. (2009) Linker effects on monolayer formation and long-range electron transfer in helical peptide monolayers. *J. Phys. Chem. B* 113, 6256-6266
20. Schlag, E. W., et al. (2007) Distal charge transport in peptides. *Angew. Chem. Int. Ed. Engl.* 46, 3196-3210
21. Sek, S., et al. (2005) Asymmetry of electron transmission through monolayers of helical polyalanine adsorbed on gold surfaces. *J. Phys. Chem. B* 109, 18433-18438
22. Sek, S., et al. (2005) Electrical behavior of molecular junctions incorporating alpha-helical peptide. *J. Phys. Chem. B* 109, 23121-23124
23. Jormakka, M., et al. (2002) Molecular basis of proton motive force generation: structure of formate dehydrogenase-N. *Science* 295, 1863-1868
24. Jeuken, L. J., et al. (2002) Electron-transfer mechanisms through biological redox chains in multicenter enzymes. *J. Am. Chem. Soc.* 124, 5702-5713
25. Coppi, M. V., et al. (2001) Development of a genetic system for *Geobacter sulfurreducens*. *Appl. Environ. Microbiol.* 67, 3180-3187
26. Lovley, D. R., and Phillips, E. J. P. (1988) Novel mode of microbial energy metabolism: organic carbon oxidation coupled to dissimilatory reduction of iron or manganese. *Appl. Environ. Microbiol.* 54, 1472-1480
27. Balch, W. E., et al. (1979) Methanogens: reevaluation of a unique biological group. *Microbiol. Rev.* 43, 260-296
28. Lovley, D. R., et al. (1984) Rapidly growing rumen methanogenic organism that synthesizes coenzyme M and has a high affinity for formate. *Appl. Environ. Microbiol.* 48, 81-87
29. Smith, P. K., et al. (1985) Measurement of protein using bicinchoninic acid. *Anal. Biochem.* 150, 76-85
30. Ames, G. F. (1974) Resolution of bacterial proteins by polyacrylamide gel electrophoresis on slabs. *J. Biol. Chem.* 249, 634-644
31. Veazey, J. P., et al. (2010) Filament-like graphite artifacts by STM. *Ultramicroscopy*

All patents and publications referenced or mentioned herein are indicative of the levels of skill of those skilled in the art to which the invention pertains, and each such referenced patent or publication is hereby specifically incorporated by reference to the same extent as if it had been incorporated by reference in its entirety individually or set forth herein in its entirety. Applicants reserve the right to physically incorporate into this specification any and all materials and information from any such cited patents or publications.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and the methods and processes are not necessarily restricted to the orders of steps indicated herein or in the claims. As used herein and in the appended claims, the singular forms "a," "an," and "the" include plural reference unless the context clearly dictates otherwise. Thus, for example, a reference to "a nucleic acid" or "a polypeptide" includes a plurality of such nucleic acids or polypeptides (for example, a solution of nucleic acids or polypeptides or a series of nucleic acid or polypeptide preparations), and so forth. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims and statements of the invention.

The following statements of the invention are intended to describe and summarize various embodiments of the invention according to the foregoing description in the specification.

STATEMENTS DESCRIBING EMBODIMENTS OF THE INVENTION

1. An isolated Geobacteraceae nanowire polypeptide that is genetically or chemically modified.
2. The nanowire polypeptide of statement 1, which is genetically modified and has at least 70% amino acid sequence identity to any of SEQ ID NO:1-10.
3. The nanowire polypeptide of statement 1 or 2, which is genetically modified and does not have a sequence that is identical to an unmodified sequence selected from the group consisting of SEQ ID NO:1-10.
4. The nanowire polypeptide of any of statements 1-3, which has at least one amino acid replaced with a hydrophilic or aromatic amino acid.
5. The nanowire polypeptide of any of statements 1-4, which has at least one amino acid replaced with a tyrosine or tryptophan residue.
6. The nanowire polypeptide of any of statements 1-5, which has at least one amino acid replaced with a charged amino acid residue.
7. The nanowire polypeptide of any of statements 1-6, which has at least one amino acid replaced with an aspartic acid, glutamic acid, lysine or arginine residue.
8. The nanowire polypeptide of any of statements 1-7, wherein at least one hydrophobic or apolar amino acid is replaced with a hydrophilic or aromatic amino acid.

9. The nanowire polypeptide of any of statements 1-8, wherein the nanowire polypeptide secondary structure is substantially helical.
10. The nanowire polypeptide of any of statements 1-9, wherein at least 50% of the nanowire polypeptide's secondary structure is α-helical.
11. The nanowire polypeptide of any of statements 1-10, wherein at least 60% of the nanowire polypeptide's secondary structure is α-helical.
12. The nanowire polypeptide of any of statements 1-11, wherein at least 70% of the nanowire polypeptide's secondary structure is α-helical.
13. The nanowire polypeptide of any of statements 1-12, wherein the nanowire polypeptide assembles into a pilus.
14. The nanowire polypeptide of any of statements 1-13, wherein the pilus is electrically conductive.
15. The nanowire polypeptide of any of statements 1-14, wherein the nanowire polypeptide contains no metals.
16. The nanowire polypeptide of any of statements 1-15, wherein the genetic or chemical modification modulates the conductive, adhesive or coupling property of the nanowire polypeptide.
17. An isolated nucleic acid encoding the nanowire polypeptide of any of statements 1-16.
18. The isolated nucleic acid of statement 17, comprising nucleic acid sequence SEQ ID NO:11.
19. The isolated nucleic acid of statement 17 or 18, which is incorporated into a replication or expression vector.
20. The isolated nucleic acid of statement 17, 18 or 19, which is operably linked to an expression control sequence.
21. The isolated nucleic acid of statement 19 or 20, wherein the vector further comprises a polyadenylation or transcriptional termination sequence.
22. An isolated host cell comprising the isolated nucleic acid of any of statements 1-21.
23. The isolated host cell of statement 22, comprising a pilT gene and/or a pilB gene from a Geobacteraceae bacterium.
24. The isolated host cell of statement 22 or 23, wherein the pilT gene and/or the pilB gene is from a *Geobacter* species.
25. The isolated host cell of any of statements 22-24, wherein the cell is a prokaryotic or eukaryotic cell.
26. The isolated host cell of any of statements 22-25, wherein the cell is a prokaryotic cell.
27. The isolated host cell of statement 25 or 26, wherein the prokaryotic cell is a gram negative bacterium.
28. The isolated host cell of statement 25 or 26, wherein the prokaryotic cell is a Geobacteraceae bacterium.
29. The isolated host cell of any of statements 25-28, wherein the prokaryotic cell is *Geobacter sulfurreducens*.
30. The isolated host cell of any of statements 25-29, wherein the prokaryotic cell is *Geobacter sulfurreducens* strain PCA.
31. The isolated host cell of any of statements 25-30, wherein the host cell does not have a pilT gene.
32. The nanowire polypeptide of statement 1, which is chemically modified to modulate the conductive, adhesive or coupling properties of the nanowire polypeptide.
33. The nanowire polypeptide of statement 32, which is chemically modified using a reagent selected from the group consisting of performic acid, a peroxide, iodoacetamide, iodoacetic acid, bissulfosuccinimidyl suberate, 1-ethyl-3-(3-dimethylaminopropyl) carbodiimide, N-ehtylmaleimide, or methyl methanethiosulfonate and S-(2,2,5,5-tetramethyl-2,5-dihydro-1H-pyrrol-3-yl) methyl methanesulfonothioate (MTSL).
34. A pilus comprising the nanowire polypeptide of any of statements 1-33.
35. A nanowire pilus comprising a protein filament isolated from a bacterium, the filament comprising the nanowire polypeptide of any of statements 1-33 as peptide subunits capable of assembling into the protein filament and capable of establishing an electrical connection with an insoluble electron acceptor.
36. A rectifier comprising: one or more genetically or chemically modified nanowire polypeptides of any of statements 1-16 in a pilus capable of establishing an electrical connection with an insoluble electron acceptor.
37. The rectifier of statement 36, wherein the genetically or chemically modified nanowires have substantially the same amino acid sequence.
38. The rectifier of statement 36, wherein at least one of the genetically or chemically modified nanowires has a different amino acid sequence from other nanowires in the pilus.
39. The rectifier of any of statements 36-38 wherein the insoluble electron acceptor is selected from Fe(III) oxide minerals, an electrode, a second isolated pilus or combinations thereof.
40. The rectifier of any of statements 36-39 adapted for use in radio demodulation, low voltage AC-DC power conversion, current steering, power switches, over voltage protection, logic circuitry in electronic devices or computer chips.
41. The rectifier of any of statements 36 to 40 capable of functioning as an asymmetric conductor for voltages having a range of ±1.2 V.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. In addition, where features or aspects of the invention are described in terms of Markush groups, those skilled in the art will recognize that the invention is also thereby described in terms of any individual member or subgroup of members of the Markush group.

Other embodiments are described within the following claims.

What is claimed:

1. An isolated Geobacteraceae nanowire polypeptide which is genetically or chemically modified, wherein the polypeptide is a variant of a polypeptide of SEQ ID NO:9 or SEQ ID NO:10 and has at least 95% amino acid sequence identity to SEQ ID NO:9 or SEQ ID NO:10, the polypeptide modified by substitution, replacement or modification of amino acid(s) in the polypeptide and having modified electrical conductivity.

2. The nanowire polypeptide of claim 1, wherein the polypeptide is genetically modified and does not have a sequence that is identical to SEQ ID NO:9 or SEQ ID NO:10.

3. The nanowire polypeptide of claim 1, wherein at least one hydrophobic or apolar amino acid is replaced with a hydrophilic or aromatic amino acid.

4. The nanowire polypeptide of claim 1, which has at least one amino acid replaced with a tyrosine or tryptophan residue.

5. The nanowire polypeptide of claim 1, which has at least one amino acid replaced with an aspartic acid, a glutamic acid, a lysine or an arginine residue.

6. The nanowire polypeptide of claim 1, wherein at least 50% of the secondary structure in the nanowire polypeptide is α-helical.

7. The nanowire polypeptide of claim 1, wherein the nanowire polypeptide assembles into an electrically conductive pilus.

8. The nanowire polypeptide of claim 1, wherein the nanowire polypeptide contains no metals.

9. The nanowire polypeptide of claim 1, which is chemically modified to modulate the conductive, adhesive and/or coupling properties of the nanowire polypeptide.

10. The nanowire polypeptide of claim 1, which is chemically modified using a reagent selected from performic acid, a peroxide, iodoacetamide, iodoacetic acid, bissulfosuccinimidyl suberate, 1-ethyl-3-(3-dimethylaminopropyl) carbodiimide, N-ethylmaleimide, methyl methanethiosulfonate and S-(2,2,5,5-tetramethyl-2,5-dihydro-1H-pyrrol-3-yl)methyl methanesulfonothioate.

11. A nanowire polypeptide selected from Geobacteraceae, wherein the amino acid sequence is genetically or chemically modified, wherein the polypeptide is a variant of and has at least 95% amino acid sequence identity to a polypeptide sequence selected from SEQ ID NO:9 and SEQ ID NO:10, wherein the polypeptide is modified by substitution, replacement or modification of the amino acid(s), wherein the nanowire polypeptide has electrical conductivity activity that is less than 90% or greater than 120% of the electrical conductivity activity of polypeptides of SEQ ID NO:9 or SEQ ID NO:10.

12. A pilus comprising the nanowire polypeptide of claim 1.

13. A mutated nanowire polypeptide comprising the amino acid sequence of SEQ ID NO: 9 or 10, wherein at least one hydrophobic or apolar amino acid selected from A11, I12, I13, I15, L16, A17, A18, I19, A20, I21, P22, A26, V29, A31, A35, A36, I40, L43, A46, L47, A50, A52, P58 and P59 is substituted or replaced with a hydrophilic or aromatic amino acid to modify electrical conductivity.

14. The mutated nanowire polypeptide of claim 13, wherein the encoded polypeptide has at least one amino acid replaced with a tyrosine or a tryptophan residue.

15. The mutated nanowire polypeptide of claim 13, wherein the encoded polypeptide has at least one amino acid replaced with an aspartic acid, a glutamic acid, a lysine or an arginine residue.

16. The mutated nanowire polypeptide of claim 13, wherein the encoded polypeptide has at least 50% of the secondary structure of the polypeptide as an α-helix.

17. The mutated nanowire polypeptide of claim 13, wherein the encoded polypeptide assembles into an electrically conductive pilus.

18. The nanowire polypeptide of claim 1, wherein the polypeptide sequence is selected from SEQ ID NO:19-25.

19. The nanowire polypeptide of claim 1 wherein at least one hydrophobic or apolar amino acid selected from A11, I12, I13, I15, L16, A17, A18, I19, A20, I21, P22, A26, V29, A31, A35, A36, I40, L43, A46, L47, A50, A52, P58 and P59 is substituted or replaced with a hydrophilic or aromatic amino acid to modify electrical conductivity.

20. The nanowire polypeptide of claim 1 from *Geobacter sulfurreducens*.

21. The mutated nanowire polypeptide of claim 13, wherein the polypeptide has at least 95% amino acid sequence identity to a polypeptide sequence selected from SEQ ID NO:9 and SEQ ID NO:10.

22. The mutated nanowire polypeptide of claim 13 wherein the polypeptide sequence is selected from SEQ ID NO:19-25.

23. The nanowire polypeptide of claim 13, wherein the polypeptide is from *Geobacter sulfurreducens*.

* * * * *

SEQUENCE LISTING

<160> NUMBER OF SEQ ID NOS: 33

<210> SEQ ID NO 1
<211> LENGTH: 71
<212> TYPE: PRT

<213> ORGANISM: Geobacter sulfurreducens

<400> SEQUENCE: 1

Met Leu Gln Lys Leu Arg Asn Arg Lys Gly Phe Thr Leu Ile Glu Leu
1               5                   10                  15

Leu Ile Val Val Ala Ile Ile Gly Ile Leu Ala Ala Ile Ala Ile Pro
            20                  25                  30

Gln Phe Ser Ala Tyr Arg Val Lys Ala Tyr Asn Ser Ala Ala Ser Ser
        35                  40                  45

Asp Leu Arg Asn Leu Lys Thr Ala Leu Glu Ser Ala Phe Ala Asp Asp
    50                  55                  60

Gln Thr Tyr Pro Pro Glu Ser
65                  70

<210> SEQ ID NO 2
<211> LENGTH: 71
<212> TYPE: PRT
<213> ORGANISM: Geobacter sulfurreducens

<400> SEQUENCE: 2

Met Leu Gln Lys Leu Arg Asn Arg Lys Gly Phe Thr Leu Ile Glu Leu
1               5                   10                  15

Leu Ile Val Val Ala Ile Ile Gly Ile Leu Ala Ala Ile Ala Ile Pro
            20                  25                  30

Gln Phe Ser Ala Tyr Arg Val Lys Ala Tyr Asn Ser Ala Ala Ser Ser
        35                  40                  45

Asp Leu Arg Asn Leu Lys Thr Ala Leu Glu Ser Ala Phe Ala Asp Asp
    50                  55                  60

Gln Thr Tyr Pro Pro Glu Ser
65                  70

<210> SEQ ID NO 3
<211> LENGTH: 70
<212> TYPE: PRT
<213> ORGANISM: Geobacter lovleyi

<400> SEQUENCE: 3

Met Leu Asn Lys Ile Arg Asn Arg Lys Gly Phe Thr Leu Ile Glu Leu
1               5                   10                  15

Leu Ile Val Val Ala Ile Ile Gly Ile Leu Ala Ala Val Ala Ile Pro
            20                  25                  30

Gln Phe Thr Thr Tyr Arg Ile Lys Gly Tyr Asn Ser Asn Ala Thr Ser
        35                  40                  45

Asp Leu Arg Asn Leu Lys Thr Val Leu Glu Ser Val Phe Ala Asp Arg
    50                  55                  60

Gln Gly Tyr Pro Gly Ser
65                  70

<210> SEQ ID NO 4
<211> LENGTH: 74
<212> TYPE: PRT
<213> ORGANISM: Pelobacter propionicus

<400> SEQUENCE: 4

Met Leu Asn Lys Leu Arg Asn Arg Lys Gly Phe Thr Leu Ile Glu Leu
1               5                   10                  15

Leu Ile Val Val Ala Ile Ile Gly Ile Leu Ala Ala Ile Ala Ile Pro
            20                  25                  30

```
Gln Phe Ser Ala Tyr Arg Ala Lys Ala Tyr Asn Ser Ala Ala Asn Ser
            35                  40                  45

Asp Leu Lys Asn Ile Lys Thr Gly Met Glu Ala Phe Met Ala Asp Asn
 50                  55                  60

Gln Gln Tyr Pro Gly Asp Val Asp Tyr Arg
 65                  70

<210> SEQ ID NO 5
<211> LENGTH: 69
<212> TYPE: PRT
<213> ORGANISM: Geobacter metallireducens

<400> SEQUENCE: 5

Met Leu Gln Lys Leu Arg Asn Lys Lys Gly Phe Thr Leu Ile Glu Leu
 1               5                  10                  15

Leu Ile Val Val Ala Ile Ile Gly Ile Leu Ala Ala Ile Ala Ile Pro
                20                  25                  30

Gln Phe Ala Ala Tyr Arg Gln Lys Ala Phe Asn Ser Ala Ala Glu Ser
            35                  40                  45

Asp Leu Lys Asn Thr Lys Thr Asn Leu Glu Ser Tyr Tyr Ser Glu His
 50                  55                  60

Gln Phe Tyr Pro Asn
 65

<210> SEQ ID NO 6
<211> LENGTH: 74
<212> TYPE: PRT
<213> ORGANISM: Geobacter sp.

<400> SEQUENCE: 6

Met Leu Asn Lys Leu Arg Ser Asn Lys Gly Phe Thr Leu Ile Glu Leu
 1               5                  10                  15

Leu Ile Val Val Ala Ile Ile Gly Ile Leu Ala Ala Ile Ala Ile Pro
                20                  25                  30

Gln Phe Ser Ala Tyr Arg Ala Lys Ala Tyr Asn Ser Ala Ala Asn Ser
            35                  40                  45

Asp Leu Lys Asn Met Lys Thr Gly Met Glu Ala Tyr Met Ala Asp Arg
 50                  55                  60

Gln Ala Tyr Pro Ala Leu Leu Asp Gln Arg
 65                  70

<210> SEQ ID NO 7
<211> LENGTH: 76
<212> TYPE: PRT
<213> ORGANISM: Geobacter bemidjiensis

<400> SEQUENCE: 7

Met Leu Asn Lys Leu Arg Ser Asn Lys Gly Phe Thr Leu Ile Glu Leu
 1               5                  10                  15

Leu Ile Val Val Ala Ile Ile Gly Ile Leu Ala Ala Ile Ala Ile Pro
                20                  25                  30

Gln Phe Ser Ala Tyr Arg Glu Lys Ala Tyr Asn Ala Ala Ser Asn Ser
            35                  40                  45

Asp Leu Lys Asn Phe Lys Thr Gly Leu Glu Ala Phe Asn Ala Asp Phe
 50                  55                  60

Gln Thr Tyr Pro Ala Ala Tyr Val Ala Ser Thr Asn
 65                  70                  75
```

<210> SEQ ID NO 8
<211> LENGTH: 74
<212> TYPE: PRT
<213> ORGANISM: Geobacter sp.

<400> SEQUENCE: 8

```
Met Leu Asn Lys Ile Arg Ser Asn Lys Gly Phe Thr Leu Ile Glu Leu
1               5                   10                  15

Leu Ile Val Val Ala Ile Ile Gly Ile Leu Ala Ala Ile Ala Ile Pro
            20                  25                  30

Gln Phe Ser Ala Tyr Arg Ala Lys Ala Tyr Asn Ala Ala Ala Asn Ser
        35                  40                  45

Asp Leu Lys Asn Ile Lys Thr Gly Met Glu Ala Tyr Met Ala Asp Arg
    50                  55                  60

Gln Ala Tyr Pro Val Ser Leu Asp Glu Arg
65                  70
```

<210> SEQ ID NO 9
<211> LENGTH: 61
<212> TYPE: PRT
<213> ORGANISM: Geobacter sulfurreducens

<400> SEQUENCE: 9

```
Phe Thr Leu Ile Glu Leu Leu Ile Val Val Ala Ile Ile Gly Ile Leu
1               5                   10                  15

Ala Ala Ile Ala Ile Pro Gln Phe Ser Ala Tyr Arg Val Lys Ala Tyr
            20                  25                  30

Asn Ser Ala Ala Ser Ser Asp Leu Arg Asn Leu Lys Thr Ala Leu Glu
        35                  40                  45

Ser Ala Phe Ala Asp Asp Gln Thr Tyr Pro Pro Glu Ser
    50                  55                  60
```

<210> SEQ ID NO 10
<211> LENGTH: 71
<212> TYPE: PRT
<213> ORGANISM: Geobacter sulfurreducens

<400> SEQUENCE: 10

```
Met Leu Gln Lys Leu Arg Asn Arg Lys Gly Phe Thr Leu Ile Glu Leu
1               5                   10                  15

Leu Ile Val Val Ala Ile Ile Gly Ile Leu Ala Ala Ile Ala Ile Pro
            20                  25                  30

Gln Phe Ser Ala Tyr Arg Val Lys Ala Tyr Asn Ser Ala Ala Ser Ser
        35                  40                  45

Asp Leu Arg Asn Leu Lys Thr Ala Leu Glu Ser Ala Phe Ala Asp Asp
    50                  55                  60

Gln Thr Tyr Pro Pro Glu Ser
65                  70
```

<210> SEQ ID NO 11
<211> LENGTH: 216
<212> TYPE: DNA
<213> ORGANISM: Geobacter sulfurreducens

<400> SEQUENCE: 11

```
atgcttcaga aactcagaaa caggaaaggt ttcacccctta tcgagctgct gatcgtcgtt    60
gcgatcatcg gtattctcgc tgcaattgcg attccgcagt tctcggcgta tcgtgtcaag   120
gcgtacaaca gcgcggcgtc aagcgacttg agaaacctga agactgctct tgagtccgca   180
```
tttgctgatg atcaaaccta tccgcccgaa agttaa                    216

<210> SEQ ID NO 12
<211> LENGTH: 36
<212> TYPE: DNA
<213> ORGANISM: Artificial Sequence
<220> FEATURE:
<223> OTHER INFORMATION: A synthetic primer

<400> SEQUENCE: 12
cgcatttgct gatgatcaaa cctttccgcc cgaaag                    36

<210> SEQ ID NO 13
<211> LENGTH: 27
<212> TYPE: DNA
<213> ORGANISM: Artificial Sequence
<220> FEATURE:
<223> OTHER INFORMATION: A synthetic primer

<400> SEQUENCE: 13
cgtgtcaagg cgttcaacag cgcggcg                             27

<210> SEQ ID NO 14
<211> LENGTH: 29
<212> TYPE: DNA
<213> ORGANISM: Artificial Sequence
<220> FEATURE:
<223> OTHER INFORMATION: A synthetic primer

<400> SEQUENCE: 14
ccgcagttct cggcgtttcg tgtcaaggc                           29

<210> SEQ ID NO 15
<211> LENGTH: 30
<212> TYPE: DNA
<213> ORGANISM: Artificial Sequence
<220> FEATURE:
<223> OTHER INFORMATION: A synthetic primer

<400> SEQUENCE: 15
gatgatcaaa cctatccgcc cgcaagttaa                          30

<210> SEQ ID NO 16
<211> LENGTH: 36
<212> TYPE: DNA
<213> ORGANISM: Artificial Sequence
<220> FEATURE:
<223> OTHER INFORMATION: A synthetic primer

<400> SEQUENCE: 16
gagtccgcat ttgctgctgc tcaaacctat ccgccc                   36

<210> SEQ ID NO 17
<211> LENGTH: 45
<212> TYPE: DNA
<213> ORGANISM: Artificial Sequence
<220> FEATURE:
<223> OTHER INFORMATION: A synthetic primer

<400> SEQUENCE: 17
gagtccgcat ttgctgctgc tcaaacctat ccgcccgcaa gttaa          45

<210> SEQ ID NO 18
<211> LENGTH: 30
<212> TYPE: DNA
<213> ORGANISM: Artificial Sequence
<220> FEATURE:
<223> OTHER INFORMATION: A synthetic primer

<400> SEQUENCE: 18
gatgatcaaa cctatccgcc cgaagcttaa                                                    30

<210> SEQ ID NO 19
<211> LENGTH: 61
<212> TYPE: PRT
<213> ORGANISM: Artificial Sequence
<220> FEATURE:
<223> OTHER INFORMATION: A synthetic polypeptide

<400> SEQUENCE: 19

Phe Thr Leu Ile Glu Leu Leu Ile Val Val Ala Ile Ile Gly Ile Leu
1               5                   10                  15

Ala Ala Ile Ala Ile Pro Gln Phe Ser Ala Tyr Arg Val Lys Ala Tyr
            20                  25                  30

Asn Ser Ala Ala Ser Ser Asp Leu Arg Asn Leu Lys Thr Ala Leu Glu
        35                  40                  45

Ser Ala Phe Ala Asp Asp Gln Thr Phe Pro Pro Glu Ser
    50                  55                  60

<210> SEQ ID NO 20
<211> LENGTH: 61
<212> TYPE: PRT
<213> ORGANISM: Artificial Sequence
<220> FEATURE:
<223> OTHER INFORMATION: A synthetic polypeptide

<400> SEQUENCE: 20

Phe Thr Leu Ile Glu Leu Leu Ile Val Val Ala Ile Ile Gly Ile Leu
1               5                   10                  15

Ala Ala Ile Ala Ile Pro Gln Phe Ser Ala Tyr Arg Val Lys Ala Phe
            20                  25                  30

Asn Ser Ala Ala Ser Ser Asp Leu Arg Asn Leu Lys Thr Ala Leu Glu
        35                  40                  45

Ser Ala Phe Ala Asp Asp Gln Thr Tyr Pro Pro Glu Ser
    50                  55                  60

<210> SEQ ID NO 21
<211> LENGTH: 61
<212> TYPE: PRT
<213> ORGANISM: Artificial Sequence
<220> FEATURE:
<223> OTHER INFORMATION: A synthetic polypeptide

<400> SEQUENCE: 21

Phe Thr Leu Ile Glu Leu Leu Ile Val Val Ala Ile Ile Gly Ile Leu
1               5                   10                  15

Ala Ala Ile Ala Ile Pro Gln Phe Ser Ala Phe Arg Val Lys Ala Tyr
            20                  25                  30

Asn Ser Ala Ala Ser Ser Asp Leu Arg Asn Leu Lys Thr Ala Leu Glu
        35                  40                  45

Ser Ala Phe Ala Asp Asp Gln Thr Tyr Pro Pro Glu Ser
    50                  55                  60

<210> SEQ ID NO 22
<211> LENGTH: 61
<212> TYPE: PRT
<213> ORGANISM: Artificial Sequence
<220> FEATURE:

<223> OTHER INFORMATION: A synthetic polypeptide

<400> SEQUENCE: 22

Phe Thr Leu Ile Glu Leu Leu Ile Val Val Ala Ile Ile Gly Ile Leu
1               5                   10                  15

Ala Ala Ile Ala Ile Pro Gln Phe Ser Ala Tyr Arg Val Lys Ala Tyr
            20                  25                  30

Asn Ser Ala Ala Ser Ser Asp Leu Arg Asn Leu Lys Thr Ala Leu Glu
        35                  40                  45

Ser Ala Phe Ala Asp Asp Gln Thr Tyr Pro Pro Ala Ser
    50                  55                  60

<210> SEQ ID NO 23
<211> LENGTH: 61
<212> TYPE: PRT
<213> ORGANISM: Artificial Sequence
<220> FEATURE:
<223> OTHER INFORMATION: A synthetic polypeptide

<400> SEQUENCE: 23

Phe Thr Leu Ile Glu Leu Leu Ile Val Val Ala Ile Ile Gly Ile Leu
1               5                   10                  15

Ala Ala Ile Ala Ile Pro Gln Phe Ser Ala Tyr Arg Val Lys Ala Tyr
            20                  25                  30

Asn Ser Ala Ala Ser Ser Asp Leu Arg Asn Leu Lys Thr Ala Leu Glu
        35                  40                  45

Ser Ala Phe Ala Ala Ala Gln Thr Tyr Pro Pro Glu Ser
    50                  55                  60

<210> SEQ ID NO 24
<211> LENGTH: 61
<212> TYPE: PRT
<213> ORGANISM: Artificial Sequence
<220> FEATURE:
<223> OTHER INFORMATION: A synthetic polypeptide

<400> SEQUENCE: 24

Phe Thr Leu Ile Glu Leu Leu Ile Val Val Ala Ile Ile Gly Ile Leu
1               5                   10                  15

Ala Ala Ile Ala Ile Pro Gln Phe Ser Ala Tyr Arg Val Lys Ala Tyr
            20                  25                  30

Asn Ser Ala Ala Ser Ser Asp Leu Arg Asn Leu Lys Thr Ala Leu Glu
        35                  40                  45

Ser Ala Phe Ala Ala Ala Gln Thr Tyr Pro Pro Ala Ser
    50                  55                  60

<210> SEQ ID NO 25
<211> LENGTH: 61
<212> TYPE: PRT
<213> ORGANISM: Artificial Sequence
<220> FEATURE:
<223> OTHER INFORMATION: A synthetic polypeptide

<400> SEQUENCE: 25

Phe Thr Leu Ile Glu Leu Leu Ile Val Val Ala Ile Ile Gly Ile Leu
1               5                   10                  15

Ala Ala Ile Ala Ile Pro Gln Phe Ser Ala Tyr Arg Val Lys Ala Tyr
            20                  25                  30

Asn Ser Ala Ala Ser Ser Asp Leu Arg Asn Leu Lys Thr Ala Leu Glu
        35                  40                  45

```
Ser Ala Phe Ala Asp Asp Gln Thr Tyr Pro Pro Glu Ala
    50                  55                  60
```

<210> SEQ ID NO 26
<211> LENGTH: 18
<212> TYPE: PRT
<213> ORGANISM: Geobacter sulfurreducens

<400> SEQUENCE: 26

```
Lys Thr Ala Leu Glu Ser Ala Phe Ala Asp Asp Gln Thr Tyr Pro Pro
  1               5                  10                  15

Glu Ser
```

<210> SEQ ID NO 27
<211> LENGTH: 18
<212> TYPE: PRT
<213> ORGANISM: Geobacter sulfurreducens

<400> SEQUENCE: 27

```
Lys Thr Ala Leu Glu Ser Ala Phe Ala Asp Asp Gln Thr Tyr Pro Pro
  1               5                  10                  15

Glu Ser
```

<210> SEQ ID NO 28
<211> LENGTH: 21
<212> TYPE: PRT
<213> ORGANISM: Geobacter sulfurreducens

<400> SEQUENCE: 28

```
Arg Asn Leu Lys Thr Ala Leu Glu Ser Ala Phe Ala Asp Asp Gln Thr
  1               5                  10                  15

Tyr Pro Pro Glu Ser
            20
```

<210> SEQ ID NO 29
<211> LENGTH: 21
<212> TYPE: PRT
<213> ORGANISM: Geobacter sulfurreducens

<400> SEQUENCE: 29

```
Arg Asn Leu Lys Thr Ala Leu Glu Ser Ala Phe Ala Asp Asp Gln Thr
  1               5                  10                  15

Tyr Pro Pro Glu Ser
            20
```

<210> SEQ ID NO 30
<211> LENGTH: 21
<212> TYPE: PRT
<213> ORGANISM: Geobacter sulfurreducens

<400> SEQUENCE: 30

```
Arg Asn Leu Lys Thr Ala Leu Glu Ser Ala Phe Ala Asp Asp Gln Thr
  1               5                  10                  15

Tyr Pro Pro Glu Ser
            20
```

<210> SEQ ID NO 31
<211> LENGTH: 32
<212> TYPE: PRT
<213> ORGANISM: Geobacter sulfurreducens

<400> SEQUENCE: 31

```
Phe Thr Leu Ile Glu Leu Leu Ile Val Val Ala Ile Ile Gly Ile Leu
1               5                   10                  15

Ala Ala Ile Ala Ile Pro Gln Phe Ser Ala Tyr Arg Val Lys Ala Val
                20                  25                  30

<210> SEQ ID NO 32
<211> LENGTH: 32
<212> TYPE: PRT
<213> ORGANISM: Geobacter sulfurreducens

<400> SEQUENCE: 32

Phe Thr Leu Ile Glu Leu Leu Ile Val Val Ala Ile Ile Gly Ile Leu
1               5                   10                  15

Ala Ala Ile Ala Ile Pro Gln Phe Ser Ala Tyr Arg Val Lys Ala Val
                20                  25                  30

<210> SEQ ID NO 33
<211> LENGTH: 32
<212> TYPE: PRT
<213> ORGANISM: Geobacter sulfurreducens

<400> SEQUENCE: 33

Phe Thr Leu Ile Glu Leu Leu Ile Val Val Ala Ile Ile Gly Ile Leu
1               5                   10                  15

Ala Ala Ile Ala Ile Pro Gln Phe Ser Ala Tyr Arg Val Lys Ala Val
                20                  25                  30
```